(12) United States Patent
Denomme et al.

(10) Patent No.: US 11,278,890 B2
(45) Date of Patent: Mar. 22, 2022

(54) PLASMON RESONANCE (PR) SYSTEM, INSTRUMENT, CARTRIDGE, AND METHODS AND CONFIGURATIONS THEREOF

(71) Applicant: NATIONAL RESEARCH COUNCIL OF CANADA, Ottawa (CA)

(72) Inventors: Ryan Denomme, Kitchener (CA); Lidija Malic, Saint Leonard (CA); Daniel Brassard, Longueuil (CA); Keith Morton, St-Bruno-de-Montarville (CA); Teodor Veres, Montreal (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 17/265,162

(22) PCT Filed: Aug. 6, 2019

(86) PCT No.: PCT/IB2019/056692
§ 371 (c)(1),
(2) Date: Feb. 1, 2021

(87) PCT Pub. No.: WO2020/031089
PCT Pub. Date: Feb. 13, 2020

(65) Prior Publication Data
US 2021/0299660 A1 Sep. 30, 2021

Related U.S. Application Data

(60) Provisional application No. 62/715,111, filed on Aug. 6, 2018, provisional application No. 62/715,137, filed on Aug. 6, 2018.

(51) Int. Cl.
*B01L 3/00* (2006.01)
*G01N 21/552* (2014.01)
*G01N 33/543* (2006.01)

(52) U.S. Cl.
CPC ... *B01L 3/502715* (2013.01); *B01L 3/502792* (2013.01); *G01N 21/554* (2013.01); *G01N 33/54386* (2013.01); *B01L 2300/0663* (2013.01)

(58) Field of Classification Search
CPC ......... B01L 3/502715; B01L 3/502792; B01L 2300/0663; G01N 33/54386; G01N 21/554
See application file for complete search history.

(56) References Cited

U.S. PATENT DOCUMENTS 8,394,249 B2 3/2013 Pollack et al.
8,562,807 B2 10/2013 Srinivasan et al.
(Continued)

FOREIGN PATENT DOCUMENTS

CA 2678772 A1 8/2008
CA 2846909 A1 9/2014

*Primary Examiner* — Dennis White
(74) *Attorney, Agent, or Firm* — TechNomos, Inc.

(57) ABSTRACT

A plasmon resonance system, instrument, cartridge, and methods for analysis of analytes is disclosed. A PR system is provided that may include a DMF-LSPR cartridge that may support both digital microfluidic (DMF) capability and localized surface plasmon resonance (LSPR) capability for analysis of analytes. In some examples, the DMF portion of the DMF-LSPR cartridge may include an electrode arrangement for performing droplet operations, whereas the LSPR portion of the DMF-LSPR cartridge may include an LSPR sensor. In other examples, the LSPR portion of the DMF-LSPR cartridge may include an in-line reference channel, wherein the in-line reference channel may be a fluid channel including at least one functionalized LSPR sensor (or sample spot) and at least one non-functionalized LSPR sensor (or reference spot). Additionally, methods of using the PR system for analysis of analytes are provided.

29 Claims, 50 Drawing Sheets

(56) References Cited

U.S. PATENT DOCUMENTS

| | | |
|---:|---:|---|
| 9,216,415 B2 | 12/2015 | Shenderov et al. |
| 2016/0096174 A1 | 4/2016 | Sturmer et al. |
| 2017/0370836 A1 | 12/2017 | Gerion et al. |

Triangle profile grating 250

Hexagonal holes grating 252

Linear grating 254

Linear blazed grating 256

PLASMON RESONANCE (PR) SYSTEM, INSTRUMENT, CARTRIDGE, AND METHODS AND CONFIGURATIONS THEREOF

RELATED APPLICATIONS

This application is a 371 Application of PCT/IB2019/056692 filed on Aug. 6, 2019, entitled "PLASMON RESONANCE (PR) SYSTEM, INSTRUMENT, CARTRIDGE, AND METHODS AND CONFIGURATIONS THEREOF", which claims priority to U.S. Provisional Application No. 62/715,111, entitled "PLASMON RESONANCE (PR) SYSTEM, INSTRUMENT, CARTRIDGE, AND METHOD," filed on Aug. 6, 2011; and to U.S. Provisional Application No. 62/715,137 entitled "PLASMON RESONANCE (PR) SYSTEM, INSTRUMENT, CARTRIDGE, AND METHOD AND CONFIGURATIONS THEREOF," filed Aug. 6, 2018; the entire disclosures of which are incorporated herein by reference.

TECHNICAL FIELD

The presently disclosed subject matter relates generally to the detection of analytes, such as molecules, such as DNA, proteins, and the like, and more particularly to the analysis of analytes using a plasmon resonance (PR) system, instrument, cartridge, and methods and various configurations thereof for analysis of analytes.

BACKGROUND

In traditional assays, protein or DNA arrays to be analyzed are flooded with a solution containing labeled target biomolecules, incubated overnight, rinsed, and then "readout" using fluorescence detection methods. This is not only time-consuming but requires large sample concentrations. Direct, label-free detection techniques exist, such as surface plasmon resonance (SPR). However, these techniques exhibit lower sensitivity and throughput, thus making them unsuitable for detection of very low concentrations of the target analyte. SPR technology has certain drawbacks. For example, immunoassays using SPR technology can be an expensive niche technology, requiring complex microfluidics systems, high precision optics, and complex assay formats.

Further, in conventional SPR there are two detection channels. For example, a first channel may include a functionalized SPR sensor (i.e., ligands immobilized on the sensor surface) for sample measurement while a second channel may include a non-functionalized SPR sensor (i.e., a blank surface) for providing a reference measurement. A volume of sample fluid is flowed across the functionalized SPR sensor. Then, an additional volume of the same sample fluid is flowed across the reference SPR sensor. Then, for analyzing the analytes of interest, the reference measurement can be subtracted from the sample measurement. A drawback of this two-channel SPR configuration is that it requires a large sample volume to supply both channels.

SUMMARY

The present disclosure describes a cartridge that may include a digital portion and an analog portion. The digital portion may include a digital microfluidics (DMF) portion capable of performing certain fluid operations. The analog portion may include a sensor portion for conducting an analysis of the fluid.

As will be appreciated herein, use of the DMF portion facilitates improved analysis techniques. For instance, the DMF portion may be used to perform fluid or droplet operations in connection with sample preparation or the like. For instance, an analyte fluid may be prepared in the DMF portion through mixing of an analyte in the buffer fluid. The DMF portion may be selectively controlled so as to provide various concentrations of mixing that may be accomplished within the DMF portion. Relatively small volume fluid operations may be precisely performed using the DMF portion. This will increase the rate of analysis and provide increased control over fluid preparation or other fluid handling aspects of the analysis.

Although the DMF portion facilitates distinct advantages in relation to fluid handling, it will be desirable to provide a continuous fluid flow in certain contexts. For instance, in relation to analysis of binding kinetics, it will be desirable to provide continuous fluid flow rather than introduction of discrete fluid droplets to a sensor. Accordingly, the analog portion of the cartridge may include a fluid channel in which continuous fluid flow may be established. For instance, droplet operations in the DMF portion may be used to provide fluid to an interface or boundary between the DMF portion and analog or sensor portion. For instance, the DMF portion may be used to supply discrete droplets of fluid that may establish and maintain continuous fluid flow within the fluid channel of the sensor portion. The examples described herein thus facilitates analysis that benefits from continuous fluid flow (e.g., including binding kinetics analysis).

In some examples, a cartridge that is interfaceable with an instrument may be provided that facilitates the advantages described above. In certain aspects, the sensor utilized in the analysis of the fluid may include a plasmon resonance (PR) sensor. Accordingly, the cartridge may include a PR sensor and/or the instrument with which the cartridge is interfaceable may include PR analysis equipment. Accordingly, in some examples, the examples described herein provide a plasmon resonance (PR) system, instrument, cartridge, and/or method for analysis of analytes. In one example, the PR system may be a localized surface plasmon resonance (LSPR) system wherein the LSPR system may include a DMF-LSPR cartridge that supports both digital microfluidic (DMF) capability and LSPR capability for analysis of analytes. The DMF-LSPR cartridge may include a DMF portion and an LSPR portion. The DMF portion of the DMF-LSPR cartridge facilitates DMF capabilities generally for merging, splitting, dispensing, diluting, other fluid handling operations, and the like. Among other things, the DMF capabilities are useful for sample preparation. The LSPR portion of the DMF-LSPR cartridge may include an LSPR sensor for (1) detecting, for example, certain molecules (e.g., target analytes) and/or chemicals in the sample, and/or (2) for analysis of analytes; e.g., for measuring binding events in real time to extract ON-rate information, OFF-rate information, and/or affinity information.

A PR instrument of the PR system may include a DMF-LSPR cartridge, an optical detection system, a flow mechanism, and a controller. The optical detection system may include, for example, an illumination source and an optical measurement device in relation to the LSPR sensor that operates in transmission mode. The flow mechanism (e.g., positive or negative pressure source) effects the flow of fluid to and from the LSPR sensor in the LSPR portion of the DMF-LSPR cartridge. The controller facilitates controlling droplet manipulation in the DMF portion by activating/deactivating electrodes in the DMF portion of the DMF-LSPR cartridge. The controller may also manage the overall operations of the PR system. Additionally, examples of methods of using the PR system are provided.

In some examples, the presently disclosed PR system, instrument, cartridge, and method may be used to measure the optical spectrum of the LSPR sensor prior to any analyte binding events occurring thereon and then measure the optical spectrum of the LSPR sensor while analyte binding events are occurring thereon.

In some examples of the presently disclosed PR system, instrument, cartridge, and method, the optical measurements interrogate a region much closer to the surface of the sensor as compared with standard SPR. In one example the LSPR signal derives from the region within about 10-40 nm of the surface as compared to a standard SPR signal which probes a region of about 250-1000 nm. Accordingly, using the DMF-LSPR cartridge, the majority of the optical signal is from very close to the surface where the actual binding events occur. By contrast, in standard SPR, measurements are taken far from the surface and are subject to a large bulk effect.

In some examples of the presently disclosed PR system, instrument, cartridge, and method, the diffusion and/or flow rate of the analyte at the LSPR sensor may be faster than the binding rate, thereby ensuring that the LSPR sensor is measuring the binding rate and is not limited by a slow diffusion or flow rate.

In some examples, the presently disclosed PR system, instrument, cartridge, and method may be used to determine the $K_D$ value, the $K_{ON}$ value, and/or the $K_{OFF}$ value of the analyte sample with an immobilized ligand wherein the $K_D$ value is a quantitative measurement of analyte affinity, the $K_{ON}$ value indicates the kinetic ON-rate of the analyte sample, and the $K_{OFF}$ value indicates the kinetic OFF-rate of the analyte sample.

Further, the presently disclosed PR system is not limited to a cartridge that supports both DMF capability and LSPR capability only. In other examples, the PR system may include a cartridge that supports both DMF capability and SPR capability, along with an optical detection system that operates in reflection mode rather than transmission mode.

Accordingly, a first aspect may include a cartridge for use with an instrument. The cartridge may include a digital microfluidics (DMF) portion comprising at least one electrode to perform fluid operations on a fluid in the DMF portion. The cartridge may also include an analog fluid portion comprising at least one fluid channel. The fluid channel is fluidly coupled with the DMF portion for receipt of a fluid from the DMF portion to provide a continuous flow of the fluid in the fluid channel.

In one example, the cartridge may include a sensor located in the at least one fluid channel, preferably on an interior surface of the channel. In turn, the continuous flow of the fluid provided in the fluid channel may provide contacting engagement of the fluid with the sensor for real-time measurement of the fluid by the sensor. The sensor may be a surface plasmon resonance (SPR) sensor for real-time measurement of an optical signal of the SPR sensor in response to the continuous flow of the fluid in the fluid channel. Other sensors may be provided in the fluid channel without limitation which may or may not be optical sensors. In this regard, any appropriate sensor that involves continuous fluid flow of a fluid in a channel may be suited for use with the cartridge of the first aspect.

In some examples, the fluid may be an analyte fluid and the continuous flow may provide a flow rate of the analyte fluid at the SPR sensor sufficient such that the mass transport rate of the analyte is higher than a binding rate of the analyte at the SPR sensor. That is, the rate at which new analyte molecules are introduced to the SPR sensor in relation to the continuous fluid flow in the fluid channel may exceed the binding rate of the analyte with the sensor. This may prevent false readings from the sensor by virtue of depletion of available analyte for binding with the sensor. For example, in certain examples, the flow rate of the analyte-containing liquid may be not less than about 25 nl/min and not greater than about 10,000 µl/min.

In an example, the cartridge may include a reservoir electrode in the DMF portion to receive and maintain the fluid in the DMF portion. The reservoir electrode may be specifically configured to facilitate retention of a fluid at the reservoir electrode portion. In addition, the cartridge may include a plurality of droplet operation electrodes in the DMF portion that are operative to supply the fluid from the reservoir electrode to the fluid channel of the analog fluid portion. The droplet operation electrodes may be configured to facilitate movement of the droplet relative to the droplet operation electrodes (e.g., to facilitate droplet operations as controlled by the droplet operation electrodes). In an example, the cartridge may include a plurality of reservoir electrodes in the DMF portion each receiving a different fluid. In turn, the plurality of droplet operation electrodes may be disposed relative to the plurality of reservoir electrodes to perform mixing of the dispensed fluids prior to providing the fluid to the fluid channel of the analog fluid portion.

As may be appreciated, a boundary may be defined between the DMF portion and the analog fluid portion of the cartridge. For instance, it may be that the analog fluid portion is substantially free of electrodes in the analog fluid portion. In this regard, the cartridge may include at least one boundary electrode disposed at the boundary between the DMF portion and the analog fluid portion. The boundary electrode may be disposed relative to the fluid channel to allow a fluid droplet at the boundary electrode to enter the fluid channel. In an example, the boundary electrode may be disposed at, but does not span, the boundary between the DMF portion and the analog fluid portion. In an alternative example, the boundary electrode may overlap the boundary between the DMF portion and the analog fluid portion.

In addition, it should be appreciated that the boundary between the DMF portion and the analog fluid portion may be arranged in any appropriate manner. In this regard, while the DMF portion and the analog portion are generally shown herein as being in a common or at least partially common plane, it may be appreciated that other arrangements are contemplated. That is, the DMF portion and analog fluid portion may be arranged such that the boundary therebetween exists in any one of a number of planes without limitation. That is, for example, in one example the DMF portion and the analog fluid portion may be at least partially coplanar such that a fluid droplet supplied by way of the droplet operation electrodes may continue in a common plane when exchanged between the DMF portion and the fluid portion. However, in alternative examples, the DMF portion and the fluid portion may exist in wholly separate planes (i.e., be stacked or otherwise arranged). Accordingly, a droplet in this arrangement may be transported in a first plane in the DMF portion and thereafter move transverse to the first plane to enter a second plane in which the droplet may subsequently be transported in the analog fluid portion.

In this latter example, it may be appreciated that having the portions in different respective planes may provide manufacturing advantages in certain contexts. Moreover, the analog fluid portion may be disposed relative to the DMF portion such that gravity may assist in the transfer of fluid from the DMF portion to the analog fluid portion in this example.

The cartridge may also include an electrical contact in electrical communication with the electrode. The electrical contact may be configured for interface with a controller for control of the at least one electrode. For instance, the cartridge may also include a pluggable interface of the cartridge comprising the electrical contact. The pluggable interface may be physically and electrically engageable with the instrument to establish electrical communication between the controller and the at least one electrode. For instance, the cartridge may be engageable with an instrument by connecting the pluggable interface with a receptacle of the instrument to both physically supportably engage the cartridge, establish fluid communication with the cartridge, and/or establish electrical communication with the cartridge.

The at least one electrode of the cartridge may be controllable by the controller to perform a droplet operation on the fluid in the DMF portion (e.g., upon engagement of the cartridge with the instrument). The droplet operation may include at least one of droplet merging, droplet splitting, droplet dispensing, droplet diluting, or combinations thereof. The at least one electrode may perform the droplet operation by electrowetting.

In an example, the cartridge may include a feedback sensor. The feedback sensor may be used to detect droplet operation of the DMF portion. In turn, the feedback sensor may be operable to communicate with the controller to provide feedback regarding the droplet operation such that the controller may control the at least one electrode to prevent introduction of filler media from the DMF portion into the fluid channel of the analog fluid portion. In various examples, the feedback sensor may include at least one of a capacitive or an optical sensor. For instance, the feedback sensor may be used to measure a droplet position, velocity, and/or volume of a droplet in the DMF portion. In one example, the sensor monitors the presence of a continuous stream of droplets going into the interface of the fluid channel. The system will trigger transport of droplets to the interface in sufficient quantity to ensure that the filler fluid does not flood the channel.

As will be described herein, the sensor disposed in the fluid channel may be an SPR sensor that utilized surface plasmon resonance to provide a measurable signal. In an example, the SPR sensor may include a sensor surface comprising one of nanosized structures distributed on the sensor surface or a continuous film comprising nano-sized features. The sensor surface of the SPR sensor may be functionalized with a specific capture molecule to which a target molecule of an analyte fluid binds to change the optical signal of the SPR sensor. The capture molecule may include a ligand immobilized on the surface of the sensor that is sensitive to binding with the target molecule of the analyte fluid to change the optical properties of the surface of the sensor resulting in the change of the optical signal of the SPR sensor.

Accordingly, the change of the optical properties may include a change in the optical signal resulting from light interacting with the sensor surface. As may be appreciated, bulk effects of light passing through the fluid may result in anomalies in the measured signal. In some examples, the optical signal may be detected within about 1000 nm from the sensor surface. In another example, the optical signal may be detected within about 100 nm from the sensor surface.

In one example, the cartridge may operate in a reflectance mode. In this regard, the SPR portion may be substantially transparent to an illumination source incident on the SPR sensor on at least one side of the SPR sensor to facilitate real-time optical measurement of the SPR sensor in the reflectance mode. Alternatively, the cartridge may operate in a transmission mode. Accordingly, the SPR portion may be substantially transparent to an illumination source incident on the SPR sensor on opposite sides of the SPR sensor to facilitate real-time optical measurement of the SPR sensor in the transmission mode.

In one example, the cartridge may be a multiple-channel cartridge. Accordingly, the cartridge may include a plurality of fluid channels. In addition, the cartridge may include a plurality of droplet operations electrodes disposed relative to the plurality of fluid channels that are operative to supply a continuous fluid flow of fluid to the plurality of fluid channels. For instance, the various fluid channel may each also include a sensor. Multiple measurements may be taken (e.g., substantially simultaneously) using the different channels. The different channels may allow for redundant measurement of a single analyte, measurement of a plurality of analytes, or may include at least one reference channel.

The cartridge may include a fluid inlet at a boundary of the DMF portion and the analog fluid portion in fluid communication with the fluid channel. Furthermore, the cartridge may include a fluid outlet in fluid communication with the fluid channel and operable to engage with a flow mechanism to establish the continuous fluid flow in the fluid channel between the fluid inlet and the fluid outlet. In this regard, in an example the fluid may be an analyte fluid and the SPR sensor of the cartridge may be operable to detect analyte affinity of the analyte fluid from the continuous fluid flow in the fluid channel. For instance, the analyte affinity may be characterized by an analyte affinity value ($K_D$). The $K_D$ is determined based on an ON-rate ($K_{ON}$) measured during an association phase of the analyte fluid at the SPR sensor and an OFF-rate ($K_{OFF}$) measured during a dissociation phase of the analyte fluid at the SPR sensor.

In another example of the first aspect, a plasmon resonance (PR) system is provided. The PR system may include a cartridge as described herein. The system may also include a PR instrument with which the cartridge is engageable. The PR instrument may include a controller in operative communication with the electrical contacts for control of the at least one electrode. The PR instrument may also include an optical detection system operative to measure an optical signal of the SPR sensor. The optical detection system of the PR instrument may include an illumination source operative to direct light incident to the SPR sensor and an optical measurement device that measures the optical signal of the SPR sensor. Further still, the PR instrument may include a flow mechanism in fluid communication with the fluid channel of the cartridge to induce the continuous fluid flow through the fluid channel to contact the SPR sensor.

In this regard, a cartridge as described herein may be engaged with the PR instrument in connection with conducting an analysis. For instance, in one example, the fluid may be an analyte fluid, and the controller may be used to detect a target molecule in the analyte fluid based on the optical signal of the SPR sensor in the presence of the analyte fluid at the SPR sensor. Furthermore, the controller may be used to measure binding events of the target molecule in the analyte fluid in real time based on the optical signal of the SPR sensor in the presence of the continuous fluid flow of the fluid in the fluid channel (e.g., using the optical detection system of the PR instrument).

In this regard, the controller of the PR system may be used to determine a quantitative measurement of analyte affinity comprising an analyte affinity value ($K_D$). The $K_D$ is determined based on an ON-rate ($K_{ON}$) measured during an association phase of the analyte fluid at the SPR sensor and an OFF-rate ($K_{OFF}$) measured during a dissociation phase of the analyte fluid at the SPR sensor. The fluid comprising the continuous fluid flow in the fluid channel may include an analyte fluid during the association phase, and wherein the fluid comprising the continuous fluid flow in the fluid channel may include a buffer solution fluid during the dissociation phase.

A second aspect may include a method of operation of a cartridge in relation to an instrument. The method may include engaging a cartridge with an instrument. The cartridge may include a digital microfluidics (DMF) portion in fluid communication with an analog fluid portion and the DMF portion is controllable to supply a continuous fluid flow to a fluid channel of the analog fluid portion. The method may include supplying fluid from the DMF portion to the fluid channel of the analog fluid portion and operating a flow mechanism in fluid communication with the fluid channel to flow the fluid through the fluid channel in a continuous fluid flow.

For instance, the method may also include measuring a signal from a sensor disposed relative to the fluid channel while the continuous fluid flow of the fluid is established in the fluid channel. In an example, the sensor may include an SPR sensor and the signal may include an optical signal of the SPR sensor.

In an example of the second aspect, the method may further include providing light from a light source of the instrument incident to the SPR sensor. In turn, the measuring may include measuring the optical signal of the SPR sensor at an optical measurement device of the instrument.

Further still, the engaging step of the method may include establishing electrical communication between a controller of the instrument and a plurality of electrodes of the DMF portion (e.g., using a pluggable interface as descried above). In turn, once electrical commination is established, the method may also include controlling the electrodes of the DMF portion. Accordingly, the supplying of the fluid may be in response to the controlling of the electrodes of the DMF portion.

In one application of the method, steps may be provided for measurement of binding kinetics of an analyte fluid. In a first period the fluid may include a buffer fluid and the measuring may include recording a baseline optical signal as the buffer fluid is flowed through the fluid channel in contacting engagement with the SPR sensor. The method may further include introducing an analyte fluid into the fluid channel in a second period. The measuring may include capturing an association signal corresponding to an association phase of the analyte in the second period. During the second period, a flow rate of the analyte fluid at the SPR sensor may be sufficient such that the mass transport rate of the analyte is higher than a binding rate of the analyte at the SPR sensor as described above in relation to the first aspect. In certain examples, the flow rate is not less than about 25 nl/min and not greater than about 10,000 µl/min.

In relation to the flow of analyte fluid relative to the SPR sensor, the method may also include determining an ON-rate ($K_{ON}$) of the analyte fluid based on the association signal. The determining the $K_{ON}$ may include fitting an association curve to the association signal.

The method may also include determination of an OFF-rate ($K_{OFF}$) of the analyte fluid. Accordingly, the method may include discontinuing the supplying of the analyte fluid to the fluid channel of the SPR portion and resupplying the buffer fluid to the fluid channel of the SPR portion in a third period. The measuring may include capturing a dissociation signal corresponding to a dissociation phase of the analyte in the third period. In turn, the method may include determining the $K_{OFF}$ of the analyte fluid based on the dissociation signal. The determining the $K_{OFF}$ may include fitting a dissociation curve to the dissociation signal.

Furthermore, the method may include determining an analyte affinity ($K_D$). In this regard, the method may include calculating $K_D$ based on the $K_{ON}$ and the $K_{OFF}$. For instance, in one example, $K_D$ may be the quotient of $K_{ON}$ and $K_{OFF}$.

Furthermore, the method may include regeneration of the SPR sensor after conclusion of the analysis of the analyte. Accordingly, the method may include supplying, in a fourth period, a regeneration buffer solution from the DMF portion to the fluid channel of the SPR portion and flowing the regeneration buffer solution through the fluid channel in contacting engagement with the SPR sensor to regenerate the SPR sensor. It will be appreciated that the regeneration buffer is specific to the chemistry of the analyte being tested, and a wide variety of buffer formulations are known in the art. The regeneration buffer may be selected to be compatible with the DMF portion and at the same time suitable for regenerating the surface of the SPR sensor.

The method of the second aspect may also include steps related to activation and/or functionalization of the SPR sensor. For instance, the method may include functionalizing the SPR sensor by contacting a functionalization fluid comprising ligands that bind the ligands to a sensor surface of the SPR sensor. In turn, the method may also include activating the sensor surface by contacting an activation fluid with the sensor surface prior to the functionalizing of the SPR sensor.

As may be appreciated, use of the DMF portion may allow for advantages in relation to fluid handling (e.g., for sample preparation or the like). In an example of the method, the method may include loading at least one fluid on the cartridge. The at least one fluid may be disposed at a reservoir electrode of the DMF portion after the loading. In turn, the method may include preparing an analyte fluid in the DMF portion for supply to the fluid channel of the analog portion. The preparing may include controlling at least one electrode in the DMF portion to dilute a sample fluid comprising a target molecule with buffer solution to achieve a desired dilution of the sample fluid in an analyte fluid. The method thus facilitates measuring respective optical signals for a plurality of different dilutions of analyte fluid comprising the target molecule.

The present disclosure relates to a cartridge designed to facilitate analyses with advantages over the traditional assays described above. The cartridge may include a digital portion and an analog portion. The digital portion may include a digital microfluidics (DMF) portion capable of performing certain fluid operations. The analog (or conventional microfluidic) portion may include a sensor portion for conducting an analysis of the fluid that may include a sample sensor and a reference sensor. In turn, the reference sensor may be used for correction of a sample signal obtained by the sample sensor.

The DMF portion may facilitate improved analytical techniques. For instance, the DMF portion may be used to perform fluid or droplet operations in connection with sample preparation or the like. For instance, an analyte fluid may be prepared in the DMF portion through mixing of an analyte in a buffer fluid. The DMF portion may be selectively controlled so as to provide various concentrations of analyte. Relatively small volume fluid operations may be precisely performed using the DMF portion. Furthermore, the DMF portion enables very low dead volumes as it avoids the need for excess liquid to prime connections between sources and destinations. Also, different fluids may be provided from the DMF portion (e.g., for use in different steps in an analysis or sensor preparation or to provide different analytes) to other portions of the device for analysis. This may assist in increasing the rate at which analysis may be conducted and may provide increased control over fluid preparation or other fluid handling aspects of the analysis.

The DMF portion may be configured to allow for selective control of the supply of fluid to various portions of the analog portion. Such configurations may allow for expanded capability and improved efficiency when preparing the sample sensor and/or reference sensor. For instance, the sample sensor and reference sensor may be collectively and/or individually activated and deactivated. Moreover, functionalization of the sample sensor may be isolated to provide functionalization of only the sample sensor. Furthermore, in contexts in which more than one sample sensor is provided in a fluid channel, the respective sample sensors may be functionalized differently (e.g., to facilitate robust measuring of multiple molecules or other characteristics of a given sample).

However, while the DMF portion may facilitate distinct advantages in relation to fluid handling, it may still be desirable to provide a continuous fluid flow in certain contexts. For instance, in relation to analysis of binding kinetics, it may be desirable to provide continuous fluid flow rather than the introduction of discrete fluid droplets to a sensor. Accordingly, the analog portion of the cartridge may include a fluid channel in which continuous fluid flow may be established. For instance, droplet operations in the DMF portion may be operative to provide fluid to an interface or boundary between the DMF portion and analog portion. For instance, the DMF portion may be operative to supply discrete droplets fluid that may establish and maintain continuous fluid flow within the fluid channel of the analog portion. In this regard, analysis that benefits from continuous fluid flow (e.g., including binding kinetics analysis) may be performed.

In some examples, a plasmon resonance (PR) system, instrument, cartridge, and method and various configurations thereof for analysis of analytes may be provided. In one example, the PR system may be a localized surface plasmon resonance (LSPR) system, wherein the LSPR system may include a DMF-LSPR cartridge that supports both digital microfluidic (DMF) capability and LSPR capability for analysis of analytes. For example, the DMF-LSPR cartridge may include a digital portion (e.g., a DMF portion) and an analog portion (e.g., a LSPR portion). The DMF portion of the DMF-LSPR cartridge may be used for DMF capabilities, e.g., for merging, splitting, dispensing, diluting, and the like. One application of these DMF capabilities may be sample preparation. Further, the DMF portion of the DMF-LSPR cartridge may be fluidly coupled to and may supply a fluid channel of the LSPR portion.

In some examples, the LSPR portion of the DMF-LSPR cartridge may include one or more LSPR sensors that are functionalized for (1) detecting, for example, certain molecules (e.g., target analytes) and/or chemicals in the sample, and (2) analysis of analytes; e.g., for measuring binding events in real time to extract ON-rate information, OFF-rate information, and/or affinity information. The functionalized LSPR sensors may be referred to herein as "sample spots" or "sample sensors" with respect to optical detection operations. Additionally, the fluid channel of the LSPR portion of the DMF-LSPR cartridge may include at least one LSPR sensor that is not functionalized (or functionalized with a non-target molecule or a "dummy" molecule). The non-functionalized LSPR sensor can be referred to herein as a "reference spot" or "reference sensor" with respect to optical detection operations. Because the "reference spot" (i.e., the non-functionalized LSPR sensor) may be provided in the same fluid channel as the "sample spots" (i.e., the functionalized LSPR sensors), the fluid channel of the LSPR portion of the DMF-LSPR cartridge may be referred to herein as an "in-line reference channel," meaning a fluid channel that may include at least one "reference spot" in line with at least one "sample spot." Fluid may be more efficiently used in connection with the cartridge as the same sample fluid provided in the fluid channel may contact the sample sensor and the reference sensor rather than having to provide a discrete amount of fluid in separate fluid channels.

In some examples, the in-line reference channel of the LSPR portion of the DMF-LSPR cartridge may include multiple outlets connected to respective flow mechanisms (e.g., positive or negative pressure sources) for directing the fluid flow to/from specific "sample spots" and/or the "reference spot."

Certain examples may relate to a PR instrument for use with the PR system that may include the DMF-LSPR cartridge, an optical detection system, one or more flow mechanisms, and a controller. The optical detection system may include, for example, an illumination source and one or more optical measurement devices in relation to the LSPR sensors. In some examples, the optical detection system may operate in transmission mode. The one or more flow mechanisms (e.g., positive or negative pressure sources) may be provided for assisting the flow of fluid to and from the LSPR sensors (i.e., the "sample spots" and "reference spot") in the LSPR portion of the DMF-LSPR cartridge. The controller may be provided for controlling the droplet manipulation by activating/deactivating electrodes in the DMF portion of the DMF-LSPR cartridge. The controller may also manage the overall operations of the PR system. Additionally, examples methods of using the PR system and the in-line reference channels are provided.

In some examples, the presently disclosed PR system, instrument, cartridge, and method may be used to measure the optical spectrum of both the functionalized LSPR sensors (the "sample spot" sensors) and the non-functionalized LSPR sensor (the "reference spot" sensor) while analyte binding events are occurring thereon in real time. The signal from the "reference spot" sensor may be used to normalize the signal from each of the "sample spot" sensors. For example, the "reference spot" signal may be used to subtract out from the "sample spot" sensors any non-specific binding of the analyte to the sensor, any instrument drift, any bulk refractive index shifts, other noise effects measured by the reference sensor, and so on. Once normalized, the sensor data from each of the "sample spots" may be processed to determine the degree of binding of the target analyte. For example, the processing of the sensor data may be used to determine the $K_D$ value, the $K_{ON}$ value, and/or the $K_{OFF}$ value of the analyte sample with an immobilized ligand, wherein the $K_D$ value is a quantitative measurement of analyte affinity, the $K_{ON}$ value indicates the kinetic ON-rate of the analyte sample, and the $K_{OFF}$ value indicates the kinetic OFF-rate of the analyte sample.

In one example, the droplet operations electrode at the boundary of the DMF portion and the LSPR portion of the DMF-LSPR cartridge may supply one fluid channel or one in-line reference channel only. In another example, the droplet operations electrode at the boundary of the DMF portion and the LSPR portion of the DMF-LSPR cartridge may supply multiple fluid channels or multiple in-line reference channels. In yet another example, at the droplet operations electrode at the boundary of the DMF portion and the LSPR portion of the DMF-LSPR cartridge, the inlet of the fluid channel and/or the in-line reference channel may be tapered or funnel-shaped. In this and other examples the inlet of the fluid channel and/or the in-line reference channel may taper from a wider opening on the DMF side of the transition to a narrow opening on the continuous flow side of the transition. The width of the narrow opening may in some cases coincide with a channel size of the continuous flow region. The width of the wide opening may in some cases substantially coincide with the width of a DMF droplet transport electrode, or with a channel size of the DMF region.

In some examples, the DMF-LSPR cartridge may include multiple DMF portions that supply a single LSPR portion. For example, the multiple DMF portions may supply one in-line reference channel of the one LSPR portion. In this example, multiple LSPR sensors (any combination of "sample spots" and "reference spots") may be arranged along the in-line reference channel of the one LSPR portion, wherein each of the DMF portions supplies a certain one of the LSPR sensors.

Further, the presently disclosed PR system is not limited to a cartridge that supports both DMF capability and LSPR capability only. In other examples, the PR system may include a cartridge that supports both DMF capability and SPR capability, along with an optical detection system, e.g., a system that operates in reflection mode rather than transmission mode.

One aspect of the present disclosure includes a cartridge for use with an instrument. The cartridge may include a digital portion that may be a digital microfluidics (DMF) portion comprising at least one electrode to perform fluid operations on a fluid in the DMF portion. The cartridge may also include an analog fluid portion comprising at least one fluid channel. The fluid channel is fluidly coupled with the DMF portion for receipt of a fluid from the DMF portion to provide a continuous flow of the fluid in the fluid channel. The cartridge may include a sample sensor located in the fluid channel that is operative to generate a measurement signal in response to fluid in the fluid channel and a reference sensor in the at least one fluid channel is operative to generate a reference signal in response to the fluid in the fluid channel.

A number of feature refinements and additional features are applicable to various aspects described herein. These feature refinements and additional features may be used individually or in any combination. As such, of the features discussed herein may be, but are not required to be, used with other features or combinations of features.

For instance, in some examples the sample sensor may be an SPR sensor. As such, the sample sensor may include a sample SPR sensor surface. The reference sensor may also be an SPR sensor such that the reference sensor may include a reference SPR sensor surface. The sample SPR sensor surface may be functionalized for a target molecule, whereas the reference SPR sensor surface may not be functionalized for the target molecule.

In one example, the cartridge may include a fluid inlet adjacent to a boundary between the DMF portion and the analog fluid portion. The fluid inlet may be in fluid communication with the fluid channel. The cartridge may also include a fluid outlet in fluid communication with the fluid channel and opposite the fluid inlet. The sample sensor and the reference sensor may be disposed between the fluid inlet and the fluid outlet. In one application, the fluid inlet may be tapered (e.g., to improve transition of a fluid from the DMF portion to the fluid channel). The fluid outlet may be adapted for interface with a flow mechanism to induce fluid flow in the fluid channel between the fluid inlet and the fluid outlet.

The cartridge may include a bypass outlet in fluid communication with the fluid channel. The bypass outlet may be disposed between the fluid inlet and the fluid outlet. For example, the bypass outlet may be between the sample sensor and the reference sensor. In turn, the bypass outlet may facilitate alternative fluid flow in the fluid channel such that, for example, fluid flow may be established with respect to the sensor and not the reference sensor. That is, the bypass outlet may allow fluid to bypass the sample sensor by flowing the fluid through the bypass outlet. As will be described in greater detail below, the bypass outlet may be selectively utilized to direct fluid as desired within the analog fluid portion.

In an example, the cartridge may include a plurality of sample sensors located in the fluid channel. For example, the plurality of sample sensors may be disposed between the fluid inlet and the bypass outlet. In this example, a bypass outlet may be disposed between each of the plurality of sample sensors for diverting fluid flow in the fluid channel from any given one of the sample sensors distal to each respective one of the bypass outlets. The respective bypass outlets may thus allow for control of the fluid flow to selectively direct fluid into contact with or around one or more of the sample sensors and/or the reference sensor. The respective bypass outlets may allow for control of the fluid flow by permitting selective flow to into a sensor region or to bypass the sensor region.

The bypass outlet may be adapted for interfacing with a bypass flow mechanism to induce flow in the fluid channel between the fluid inlet and the bypass outlet. The flow mechanism and the bypass flow mechanism may be independently controllable (e.g., to selectively provide fluid flow relative to the sample sensors and/or the reference sensor). In another example, the flow mechanism and the bypass flow mechanism may be in selective fluidic communication with a common flow mechanism. In turn, a bypass valve may be disposed between the bypass outlet and the fluid mechanism to selectively fluidly connect the bypass outlet to the flow mechanism. An outlet valve may also be disposed between the fluid outlet and the fluid mechanism to selectively fluidly connect the fluid outlet to the flow mechanism.

As described above, use of the DMF portion may allow for flexibility in relation to supply of a fluid to the analog portion. In this regard, the DMF portion may include a plurality of independent fluid handling paths. Each independent fluid handling path may be operative to supply a fluid droplet from a reservoir electrode via one or more droplet operation electrodes. As may be appreciated, a plurality of reservoir electrodes may be provided. In turn, different fluids may be provided independently to various portions of the analog portion by way of the independent fluid handling paths.

For example, a first fluid handling path may be operative to supply fluid from the DMF portion to a fluid inlet of the fluid channel in the analog portion. Additionally, a second fluid handling path may be operative to capture fluid from a fluid outlet of the fluid channel. Fluid captured at the fluid outlet may be further processed, collected, or recirculated. For instance, fluid exiting the fluid outlet may be recycled back to the DMF portion for further processing and/or reintroduction into a fluid channel from the DMF portion. As such, fluid may be transported from the digital portion to the analog portion and back to the digital portion as desired.

In another example, a first fluid handling path may be operative to supply fluid to a fluid inlet of the fluid channel in the analog portion and a second fluid handling path may be operative to supply fluid to the sample sensor. Fluids may be selectively provided to the entire fluid channel or may be supplied directly to the fluid channel adjacent to the sample sensor. Or, fluids may be selectively provided to the entire fluid channel or may be supplied directly to the fluid channel away from the sample sensor. Furthermore, in some cases a third fluid handling path may be operative to supply fluid to the reference sensor. Accordingly, the direct supply of fluid to either the sample sensor or reference sensor may allow for independent supply of fluid (e.g., for activation, functionalization, or the like). In this example, the first fluid handling path that supplies fluid to the fluid inlet may also be used to introduce a fluid that is to be supplied to both the sample sensor and the reference sensor. Additional fluid handling paths may be provided for further independent supply of fluid to various portions of the analog portion. For instance, a fourth fluid handling path may be operative to supply fluid to a second sample sensor (e.g., for independent activation, functionalization, and/or deactivation of the second sample sensor).

In another example, the cartridge may include a plurality of fluid channels, each having located therein a sample sensor and a reference sensor. The plurality of fluid channels may each be fluidly coupled with the DMF portion for receipt of a respective fluid from the DMF portion to provide a continuous flow of the fluid in each of the plurality of fluid channels for contacting engagement of the respective fluids with corresponding ones of the sample sensors and the reference sensors for real-time optical measurement of a signal of the sample sensors and the reference sensors. Multiple measurements may be taken (e.g., substantially simultaneously) using the different channels. The different channels may allow for redundant measurement of a single analyte, measurement of a plurality of analytes, or may include at least one reference channel.

As the sample sensor and/or the reference sensor may include an SPR sensor, the sample sensor and the reference sensor may each include one of nanometer-sized structures distributed on a sensor surface or a sensor surface comprising a continuous film comprising nanometer-sized features. For instance, the sensor surface of the sample sensor may be functionalized with a specific capture molecule (e.g., a protein, antibody or nucleic acid) to which a target molecule of an analyte fluid binds to alter an optical signal of the sample sensor. In contrast, the sensor surface of the reference sensor may not be functionalized with the specific capture molecule. For instance, the reference sensor may include a SPR sensor surface functionalized for a non-target molecule other than the target molecule or may include an SPR sensor surface that was activated, but never functionalized with a ligand.

In an example, the capture molecule may include a ligand immobilized on the surface of the sensor that is sensitive to binding with the target molecule of the analyte fluid to change the optical properties of the surface of the sensor resulting in the change of the optical signal of the sensor. In one example, the optical signal may be detected within about 1000 nm from the sensor surface. Alternatively, the optical signal may be detected within about 100 nm from the sensor surface.

In an example, the fluid may be an analyte fluid and the continuous flow may provide a flow rate of the analyte fluid at the SPR sensor sufficient such that a diffusion rate of the analyte fluid is higher than a binding rate of the analyte fluid at the SPR sensor. That is, the rate at which new analyte molecules are introduced to the SPR sensor in relation to the continuous fluid flow in the fluid channel may exceed the binding rate of the analyte with the sensor. This may prevent false readings from the sensor by virtue of depletion of available analyte for binding with the sensor. For example, in some cases, the flow rate may be not less than about 0.05 µl/min and not greater than about 10,000 µl/min.

In an example, the cartridge may include a reservoir electrode in the DMF portion for receipt and storage of the fluid in the DMF portion. The reservoir electrode may be specifically configured to facilitate retention of a fluid at the reservoir electrode portion. The cartridge may also include a plurality of droplet operation electrodes in the DMF portion that are operative to supply the fluid from the at least one reservoir electrode to the fluid channel of the analog fluid portion. The droplet operation electrodes may be configured to facilitate movement of the droplet relative to the droplet operation electrodes (e.g., to facilitate droplet operations as controlled by the droplet operation electrodes). In an example, the cartridge may include a plurality of reservoir electrodes in the DMF portion each receiving a different fluid. In turn, the plurality of droplet operation electrodes may be disposed relative to the plurality of reservoir electrodes to perform mixing of the different fluids prior to providing the fluid to the fluid channel of the analog fluid portion.

The reservoir electrode may be arranged with respect to a fluid reservoir for supplying fluid to the reservoir electrode. In this regard, the fluid reservoir may provide a larger supply volume of fluid than may otherwise be retained by the reservoir electrode. For instance, the fluid reservoir may include a fluid capacity of not less than about 1 µl of fluid and not greater than about 2 ml of fluid. In one example, a fluid passageway may extend between the fluid reservoir and the reservoir electrode. In turn, the reservoir electrode may be operative to maintain a fluid pressure of fluid in the fluid reservoir at the fluid reservoir for controllable release of fluid from the fluid reservoir by the reservoir electrode.

As may be appreciated, a boundary may be defined between the DMF portion and the analog fluid portion of the cartridge. For instance, it may be that the analog fluid portion is substantially free of electrodes in the analog fluid portion. In this regard, the cartridge may include at least one boundary electrode disposed at a boundary between the DMF portion and the analog fluid portion. The boundary electrode may be disposed relative to the fluid channel to allow a fluid droplet at the boundary electrode to enter the fluid channel. For instance, the boundary electrode may be disposed at, but not span, the boundary between the DMF portion and the analog fluid portion. Alternatively, the boundary electrode may overlap the boundary between the DMF portion and the analog portion.

In addition, it should be appreciated that the boundary between the DMF portion and the analog fluid portion may be arranged in any appropriate manner. In this regard, while the DMF portion and the analog portion are generally shown herein as being in a common or at least partially common plane, it may be appreciated that other arrangements are contemplated. That is, the DMF portion and analog fluid portion may be arranged such that the boundary therebetween exists in any one of a number of planes without limitation. That is, for example, in one example the DMF portion and the analog fluid portion may be at least partially coplanar such that a fluid droplet supplied by way of the droplet operation electrodes may continue in a common plane when exchanged between the DMF portion and the fluid portion. However, in alternative examples, the DMF portion and the fluid portion may exist in partially or wholly separate planes (e.g., be stacked or otherwise arranged). Accordingly, a droplet in this arrangement may be transported in a first plane in the DMF portion and thereafter move transverse to the first plane to enter a second plane in which the droplet may subsequently be transported in the analog fluid portion. In this latter example, it may be appreciated that having the portions in different respective planes may provide manufacturing advantages. In some cases, the analog fluid portion may be disposed relative to the DMF portion such that gravity may assist in transfer of fluid from the DMF portion to the analog fluid portion in this example.

The cartridge may also include an electrical contact in electrical communication with the electrode. The electrical contact may be configured for interfacing with a controller for control of the at least one electrode. For instance, the cartridge may also include a pluggable interface of the cartridge comprising the electrical contact. The pluggable interface may be physically and electrically engageable with the instrument to establish electrical communication between the controller and the at least one electrode. For instance, the cartridge may be engageable with an instrument by connecting the pluggable interface with a receptacle of the instrument to both physically support and the cartridge, establish fluid communication with the cartridge, and/or establish electrical communication with the cartridge.

The at least one electrode of the cartridge may be controllable by the controller to perform a droplet operation on the fluid in the DMF portion (e.g., upon engagement of the cartridge with the instrument). The droplet operation may include at least one of droplet merging, droplet splitting, droplet dispensing, droplet diluting, or combinations thereof. The at least one electrode may perform the droplet operation by electrowetting.

In an example, the cartridge may include a feedback sensor. The feedback sensor may be operative to detect droplet operations within the DMF portion. In turn, the feedback sensor may be used to communicate with the controller to provide feedback regarding the droplet operations such that the controller may control the at least one electrode to prevent introduction of filler media from the DMF portion into the fluid channel of the analog fluid portion. In various examples, the feedback sensor may include at least one of a capacitive or an optical sensor. For instance, the feedback sensor may be operative to measure a droplet position, velocity, and/or volume of a droplet in the DMF portion. Examples of DMF capacitance sensing are described in U.S. Patent Pub. No. 20160096174, published on Apr. 7, 2016, the disclosure of which is incorporated herein by reference for its teaching on capacitance detection.

In one example, the cartridge may operate in a reflectance mode. In this regard, the SPR portion may be substantially transparent to an illumination source incident on the SPR sensor on at least one side of the SPR sensor to facilitate real-time optical measurement of the SPR sensor in the reflectance mode. Alternatively, the cartridge may operate in a transmission mode. Accordingly, the SPR portion may be substantially transparent to an illumination source incident on the SPR sensor on opposite sides of the SPR sensor to facilitate real-time optical measurement of the SPR sensor in the transmission mode.

Use of the reference sensor may allow for correction of the measurement signal of the sample sensor. For instance, the reference signal may be used in relation to the measurement signal to generate a corrected measurement signal from the SPR sensor. In one approach, the fluid may be an analyte fluid, and the SPR sensor may be used to detect analyte affinity of an analyte fluid from the continuous flow of the analyte fluid in the fluid channel at least in part based on the reference signal of the reference sensor. In an example, the analyte affinity may be characterized by an analyte affinity value ($K_D$). The $K_D$ may be determined based on an ON-rate ($K_{ON}$) measured during an association phase of the analyte fluid at the SPR sensor and an OFF-rate ($K_{OFF}$) measured during a dissociation phase of the analyte fluid at the SPR sensor.

In another example, a plasmon resonance (PR) system may be provided. The PR system may include a cartridge as described herein. The system may also include a PR instrument with which the cartridge is engageable. The PR instrument may include a controller in operative communication with the electrical contacts for control of the at least one electrode. The PR instrument may also include an optical detection system. The optical detection system of the PR instrument may include an illumination source. In some cases, a single illumination source may be operative to direct light incident to the sample sensor and the reference sensor. In other cases, separate illumination sources may be provided for the sample sensor and the reference sensor, respectively. In other cases, multiple illumination sources may be provided for the sample sensor and/or multiple illumination sources may be provided for the reference sensor.

The system may also include an optical measurement device including an optical sensor. Again, a single optical measurement device may measure the sample signal of the sample sensor and the reference signal of the reference sensor or separate optical measurement devices may be provided for measuring the sample signal of the sample sensor and the reference signal of the reference sensor, respectively. In this regard, the optical detection system may include a sample optical measurement device that measures the sample optical signal of the sample sensor and a reference optical measurement device that measures the reference optical signal of the reference signal. Further still, the PR instrument may include a flow mechanism in fluid communication with the fluid channel of the cartridge to induce the continuous fluid flow through the fluid channel.

In an example, the fluid may be an analyte fluid, and the controller may be operative to conduct operations selected to detect a target molecule in the analyte fluid based on the sample signal of the sample sensor in the presence of the fluid at the sample sensor as corrected by the reference signal of the reference signal in the presence of the fluid at the reference sensor. For instance, the sample signal may include an optical signal of the sample sensor and the reference signal may include an optical signal of the reference sensor. Accordingly, the controller may subtract the reference signal from the sample signal to determine a corrected measurement signal.

In another example, the controller may be operative to measure kinetic binding events of a target molecule in the analyte fluid in real time based on the measurement signal of the SPR sensor in the presence of the continuous fluid flow of the fluid in the fluid channel as corrected by the reference optical signal of the reference signal in the presence of the fluid at the reference sensor. For instance, the controller may be operative to determine a quantitative measurement of analyte affinity comprising an analyte affinity value ($K_D$). The $K_D$ may be determined based on an ON-rate ($K_{ON}$) measured during an association phase of the analyte fluid at the SPR sensor and an OFF-rate ($K_{OFF}$) measured during a dissociation phase of the analyte fluid at the SPR sensor.

Another aspect may include a method of operation of a cartridge in relation to an instrument. The method may include engaging a cartridge with an instrument. The cartridge may include a DMF portion in fluid communication with an analog fluid portion and the DMF portion is controllable to supply a continuous fluid flow to a fluid channel of the analog fluid portion. The method may also include supplying fluid from the DMF portion to the fluid channel of the analog fluid portion and operating a flow mechanism in fluid communication with the fluid channel to flow the fluid through the fluid channel in a continuous fluid flow. The method may include measuring a measurement signal from a sample sensor located in the fluid channel to generate a measurement signal in response to fluid in the fluid channel and measuring a reference signal from a reference sensor located in the fluid channel to generate a reference signal in response to fluid in the fluid channel.

For instance, the sample sensor may include a sample SPR sensor surface that is functionalized for a target molecule. In turn, the sample signal may be an optical signal of the sample SPR sensor surface. The reference sensor may include a reference SPR sensor surface that is not functionalized for the target molecule. The reference signal may be an optical signal of the reference SPR sensor surface.

The method may also include providing light from a light source of the instrument incident to the sample sensor and the reference sensor. As described above, a first light source may be provided to provide light incident to the sample sensor and a second light source may be provided to provide light incident to the reference sensor. In another approach, a single light source may be provided to provide light to the sample sensor and the reference sensor. The measuring the measurement signal may be performed by a first optical measurement device and the measuring the reference signal may be performed by a second optical measurement device. Alternatively, the measuring the measurement signal and the measuring the reference signal may be performed by a common optical measurement device.

In relation to the engaging step of the second aspect, the engaging may also include establishing electrical communication between a controller of the instrument and a plurality of electrodes of the DMF portion. Furthermore, the method may include controlling the electrodes of the DMF portion. The supplying of the fluid may be in response to the controlling of the electrodes of the DMF portion.

For example, in a first period the fluid may be a buffer fluid and the measuring may include recording a baseline optical signal as the buffer fluid is flowed through the fluid channel in contacting engagement with the sample sensor. The baseline signal may be based on the measurement signal and the reference signal in the first period. The baseline signal may be the measurement signal less the reference signal when the buffer fluid is flowed through the fluid channel.

In addition, the method may include introducing an analyte fluid into the fluid channel in a second period. In this regard, the measuring may include capturing an association signal corresponding to an association phase of the analyte in the second period based on the measurement signal and the reference signal in the second period. The association signal may include the measurement signal less the reference signal when the analyte fluid is flowed through the fluid channel in the second period. As described above, a flow rate of the analyte fluid at the sample sensor may be sufficient such that a diffusion rate of the analyte is higher than a binding rate of the analyte at the sample sensor. For instance, the flow rate may be not less than about 0.05 µl/min and not greater than about 10,000 µl/min. In relation to the analysis of an analyte fluid, the method may include determining an ON-rate ($K_{ON}$) of the analyte fluid based on the association signal. The determining the $K_{ON}$ may include fitting an association curve to the association signal.

Additionally, a dissociation phase of the analyte fluid may be provided. In this regard, the method may include discontinuing the supplying of the analyte fluid to the fluid channel of the analog fluid portion and resupplying the buffer fluid to the fluid channel of the analog fluid portion in a third period. As such, the measuring may include capturing a dissociation signal corresponding to a dissociation phase of the analyte in the third period based on the measurement signal and the reference signal in the third period. The dissociation signal may include the measurement signal less the reference signal when the buffer fluid is flowed through the fluid channel in the third period. Moreover, the method may include determining an OFF-rate ($K_{OFF}$) of the analyte fluid based on the dissociation signal. The determining the $K_{OFF}$ may include fitting a dissociation curve to the dissociation signal.

In view of the capture of the $K_{ON}$ and $K_{OFF}$, the method may include determining an analyte affinity value ($K_D$). The method may include calculating $K_D$ based on the $K_{ON}$ and the $K_{OFF}$ (e.g., $K_D$ may be the quotient of $K_{ON}$ and $K_{OFF}$).

The method may also include regeneration of the sample sensor. In this regard, the method may include supplying, in a fourth period, a regeneration buffer solution from the DMF portion to the fluid channel of the analog portion and flowing the regeneration buffer solution through the fluid channel in contacting engagement with the sample sensor to regenerate the sample sensor.

Further still, the method may include various approaches to activation, functionalization, and/or deactivation of the sample sensor and/or reference sensor. For instance, various ones of the activation, functionalization, and/or deactivation steps may be carried out on one or more sensors and/or may be performed individually relative to different ones of the sensors. For example, in one approach, the method may include activating the sample sensor and the reference sensor by flowing an activation fluid through the fluid channel at the sample senor and the reference sensor. The method may also include functionalizing only the sample sensor by flowing a functionalization fluid through the fluid channel at the sample sensor and bypassing the functionalization fluid from the fluid channel through a bypass outlet prior to the reference sensor. Furthermore, the method may include deactivating the sample sensor and the reference sensor by flowing a deactivation fluid through the fluid channel at the sample senor and the reference sensor. The activating step may include activating a plurality of sample sensors in the fluid channel. Also, the functionalizing step may include functionalizing a plurality of sample sensors in the fluid channel. Likewise, the deactivating step may include deactivating the plurality of sample sensors. Additionally, the functionalizing step may include individually functionalizing a plurality of sample sensors with different respective capture molecules.

In another approach, the method may include activating, functionalizing, and deactivating the sample sensors separately from activation and deactivation of the reference sample. In this regard, the method may include activating the sample sensor by flowing an activation fluid through the fluid channel at the sample senor and bypassing the activation fluid from the fluid channel through a bypass outlet prior to the reference sensor. For example, a mixture of N-ethyl-N'-(dimethylaminopropyl) carbodiimide (EDC) and N-hydroxysuccinimide (NHS) may be used to activate carboxyl groups on the sensor surface. Furthermore, the method may include functionalizing the sample sensor by flowing a functionalization fluid through the fluid channel at the sample sensor and bypassing the functionalization fluid from the fluid channel through a bypass outlet prior to the reference sensor. Also, the method may include deactivating the sample sensor by flowing a deactivation fluid through the fluid channel at the sample senor and bypassing the deactivation fluid from the fluid channel through a bypass outlet prior to the reference sensor. For example, ethanolamine can be used to deactivate surface groups that were not functionalized to eliminate binding sites for analytes not specific to the functionalized sensor. In this approach, the method may also include activating another sample sensor (i.e., a plurality of sample sensors) by flowing an activation fluid through the fluid channel at the sample senor and bypassing the activation fluid from the fluid channel through a bypass outlet prior to the reference sensor. The method may include functionalizing the another sample sensor (i.e., a plurality of sample sensors) by flowing a functionalization fluid through the fluid channel at the sample sensor and bypassing the functionalization fluid from the fluid channel through a bypass outlet prior to the reference sensor. Also, the method may include deactivating the another sample sensor (i.e., a plurality of sample sensors) by flowing a deactivation fluid through the fluid channel at the sample senor and bypassing the deactivation fluid from the fluid channel through a bypass outlet prior to the reference sensor. The sample sensors may be activated in a single activation step, functionalized in a single functionalization step, and deactivated in a single deactivation step. Alternatively, the sample sensors may be functionalized in separate functionalization steps in which the respective sample sensors are functionalized with different capture molecules. In this approach, the method may include, after the activating, functionalization, and deactivating of one or more sample sensors, activating the reference sensor by flowing an activation fluid through the fluid channel at the reference senor and deactivating the reference sensor by flowing a deactivation fluid through the fluid channel at the reference senor.

BRIEF DESCRIPTION OF THE DRAWINGS

The features and advantages of the presently described subject matter will be more clearly understood from the following description taken in conjunction with the accompanying drawings, which are not necessarily drawn to scale, and wherein.

DETAILED DESCRIPTION OF EXEMPLARY EXAMPLES

Figure 1:
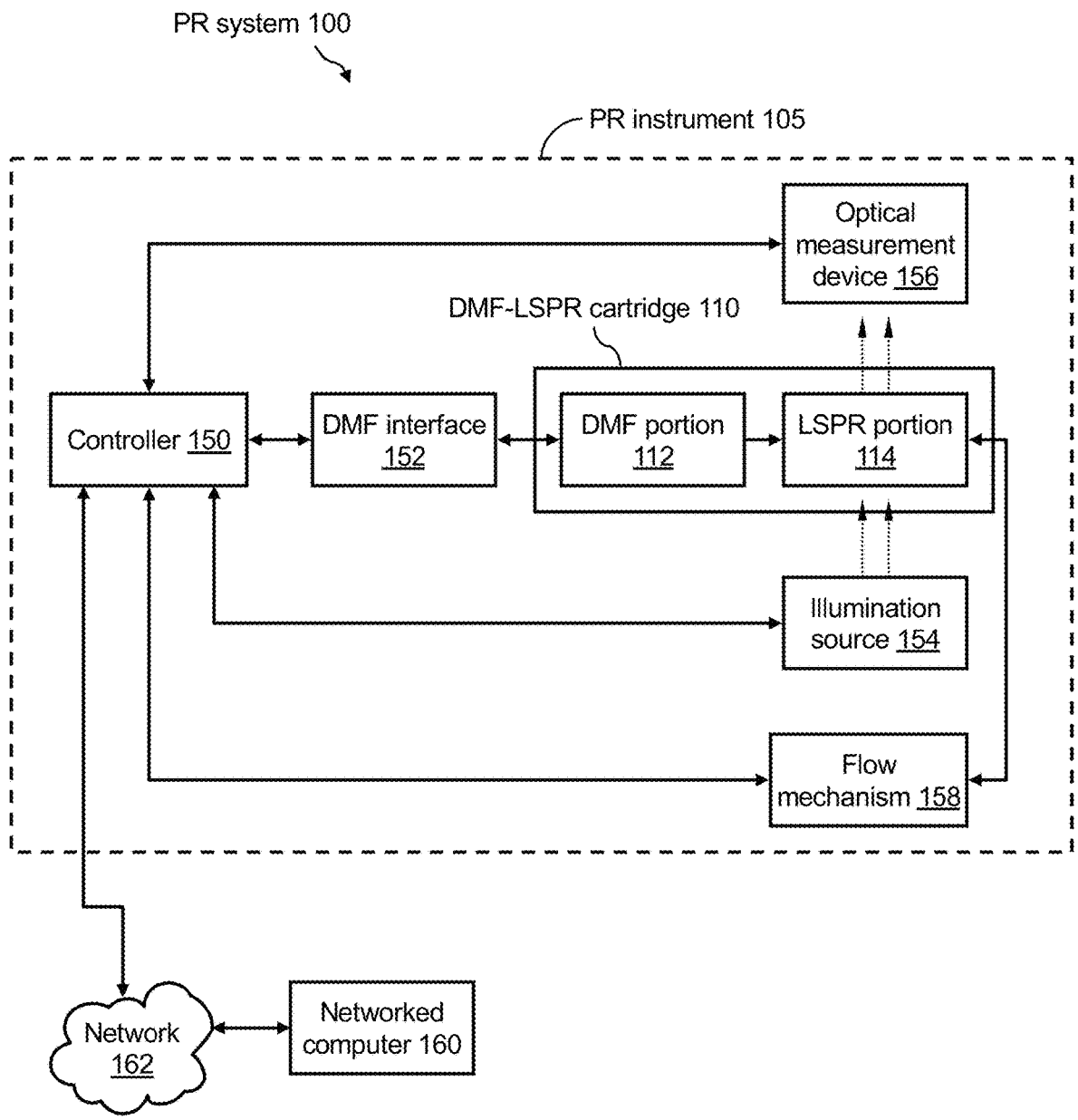
FIG. 1 is a block diagram of an example of the presently disclosed PR system that may include a DMF-LSPR cartridge for analysis of analytes.

While the present disclosure is susceptible to various modifications and alternative forms, specific examples thereof have been shown by way of example in the drawings and are herein described in detail. It should be understood, however, that it is not intended to limit the disclosure to the particular form disclosed, but rather, the disclosure is to support all modifications, equivalents, and alternatives falling within the scope as defined by the claims.

FIG. 1 is a block diagram of an example of the presently disclosed PR system 100 that may include a cartridge that supports both DMF and LSPR for analysis of analytes. Accordingly, PR system 100 may be an LSPR system wherein PR system 100 may include a DMF-LSPR cartridge 110 that supports both DMF capability and LSPR capability for analysis of analytes. In PR system 100 for analysis of analytes, analysis may include, for example, detection, identification, quantification, or measuring analytes and/or the interactions of analytes with other substances, such as binding kinetics. Exemplary analytes may include, but are not limited to, small molecules, proteins, peptides, atoms, ions, and the like. For example, PR system 100 may be used to measure the binding kinetics of a ligand to a macromolecule, such as a receptor.

For example, DMF-LSPR cartridge 110 may include a DMF portion 112 and an LSPR portion 114. DMF portion 112 of DMF-LSPR cartridge 110 facilitates DMF capabilities generally for merging, splitting, dispensing, diluting, other fluid handling operations, and the like. One application of these DMF capabilities may be sample preparation. However, the DMF capabilities may be used for other processes, such as waste removal or flushing between runs.

LSPR portion 114 may include the detection portion of DMF-LSPR cartridge 110 that may include an LSPR sensor 136 (see FIG. 2) that is used for (1) detecting, for example, certain molecules (e.g., target analytes) and/or chemicals in the sample, and (2) for analysis of analytes; e.g., for measuring binding events in real time to extract ON-rate information, OFF-rate information, and/or affinity information. DMF portion 112 and LSPR portion 114 may be fluidly coupled. DMF-LSPR cartridge 110 of PR system 100 may be provided, for example, as a disposable and/or reusable cartridge. More details of examples of a DMF-LSPR cartridge 110 are shown and described hereinbelow with reference to FIG. 2 through FIG. 9.

PR system 100 may further include a controller 150, a DMF interface 152, an illumination source 154, an optical measurement device 156, and a flow mechanism 158. Controller 150 may be electrically coupled to the various hardware components of PR system 100, such as to DMF-LSPR cartridge 110, illumination source 154, optical measurement device 156, and flow mechanism 158. In particular, controller 150 may be electrically coupled to DMF-LSPR cartridge 110 via DMF interface 152 wherein DMF interface 152 may be, for example, a pluggable interface for connecting mechanically and electrically to DMF-LSPR cartridge 110. Together, DMF-LSPR cartridge 110, controller 150, DMF interface 152, illumination source 154, optical measurement device 156, and flow mechanism 158 may include a PR instrument 105.

Controller 150 may, for example, be a general-purpose computer, special purpose computer, personal computer, microprocessor, or other programmable data processing apparatus. The controller 150 may include or be in operative communication with a memory. Controller 150 may provide processing capabilities, such as storing, interpreting, and/or executing software instructions (e.g., non-transitory machine-readable data comprising such software instructions stored in the memory), as well as controlling the overall operations of PR system 100. Controller 150 may be configured and programmed to control data and/or power aspects of these devices. For example, with respect to DMF portion 112 of DMF-LSPR cartridge 110, controller 150 may control droplet manipulation by activating/deactivating electrodes. Generally, controller 150 may also be used for any functions of PR system 100. For example, controller 150 may be used to authenticate the DMF-LSPR cartridge 110 in a fashion similar to how printer manufacturers check the authenticity of an ink cartridge, controller 150 may be used to verify that the DMF-LSPR cartridge 110 is not expired, controller 150 may be used to confirm the cleanliness of the DMF-LSPR cartridge 110 by running a certain protocol for that purpose, and so on.

Additionally, in some examples, DMF-LSPR cartridge 110 may include capacitive feedback sensing. A signal generated using a capacitive sensor that may be monitored to detect droplet position, velocity, and volume. In one example, using controller 150, sample/analyte droplets may be redirected at the entrance of the detection channel (e.g., a fluid channel 130, see FIG. 2) of LSPR portion 114 to prevent air from entering the detection chamber. Further, in other examples, instead of capacitive feedback sensing, DMF-LSPR cartridge 110 may include a camera to provide optical measurement of the droplet position, velocity and volume, which can trigger controller 150 to re-route the droplets at appropriate positions.

Optionally, PR instrument 105 may be connected to a network. For example, controller 150 may be in communication with a networked computer 160 via a network 162. Networked computer 160 may be, for example, any centralized server or cloud server. Network 162 may be, for example, a local area network (LAN) or wide area network (WAN) for connecting to the internet.

In PR system 100, illumination source 154 and optical measurement device 156 may be arranged with respect to LSPR sensor 136 (see FIG. 2) of LSPR portion 114 of DMF-LSPR cartridge 110. Illumination source 154 may be, for example, a light source for the visible range (400-800 nm), such as, but not limited to, a white light-emitting diode (LED), a halogen bulb, an arc lamp, an incandescent lamp, lasers, and the like. Illumination source 154 is not limited to a white light source. Illumination source 154 may be any color light that is useful in PR system 100. Optical measurement device 156 may be used to obtain LSPR light intensity readings. Optical measurement device 156 may be, for example, a charge coupled device, a photodetector, a spectrometer, a photodiode array, or any combinations thereof. Further, PR system 100 is not limited to one illumination source 154 and one optical measurement device 156 only. For instance, PR system 100 may include multiple illumination sources 154 and/or multiple optical measurement devices 156 in order to support multiple-channel DMF-LSPR cartridges 110, such as shown in the example depicted in FIG. 9.

In PR system 100, flow mechanism 158 may be fluidly coupled to LSPR portion 114 of DMF-LSPR cartridge 110. Flow mechanism 158 may be any mechanism for producing and/or assisting flow within a fluid channel (see FIG. 4) of LSPR portion 114. Flow mechanism 158 may be, for example, a positive or negative pressure source (e.g., a syringe pump), a microfluidic pump, an electro-osmotic pump, a passive pumping mechanism (e.g., capillary action, gravity flow), and the like.

Figure 2:
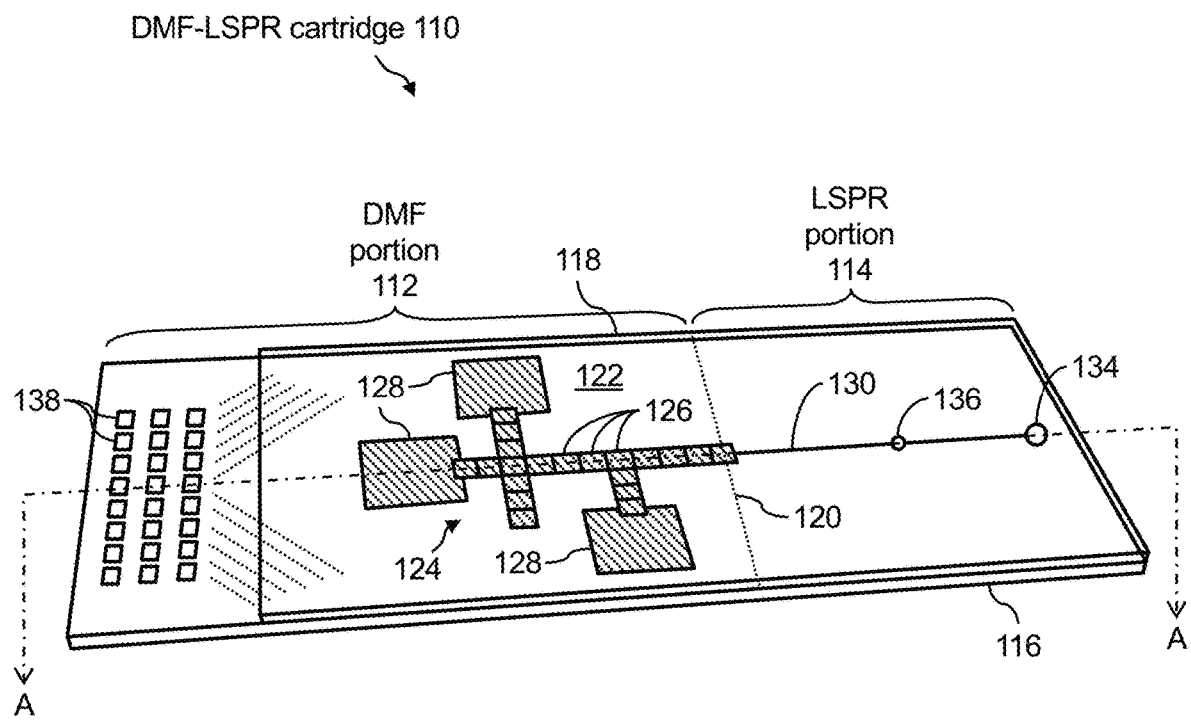
FIG. 2 is a perspective view of a single-channel DMF-LSPR cartridge, which is one example of a DMF-LSPR cartridge of a presently disclosed PR system.
Figure 3:
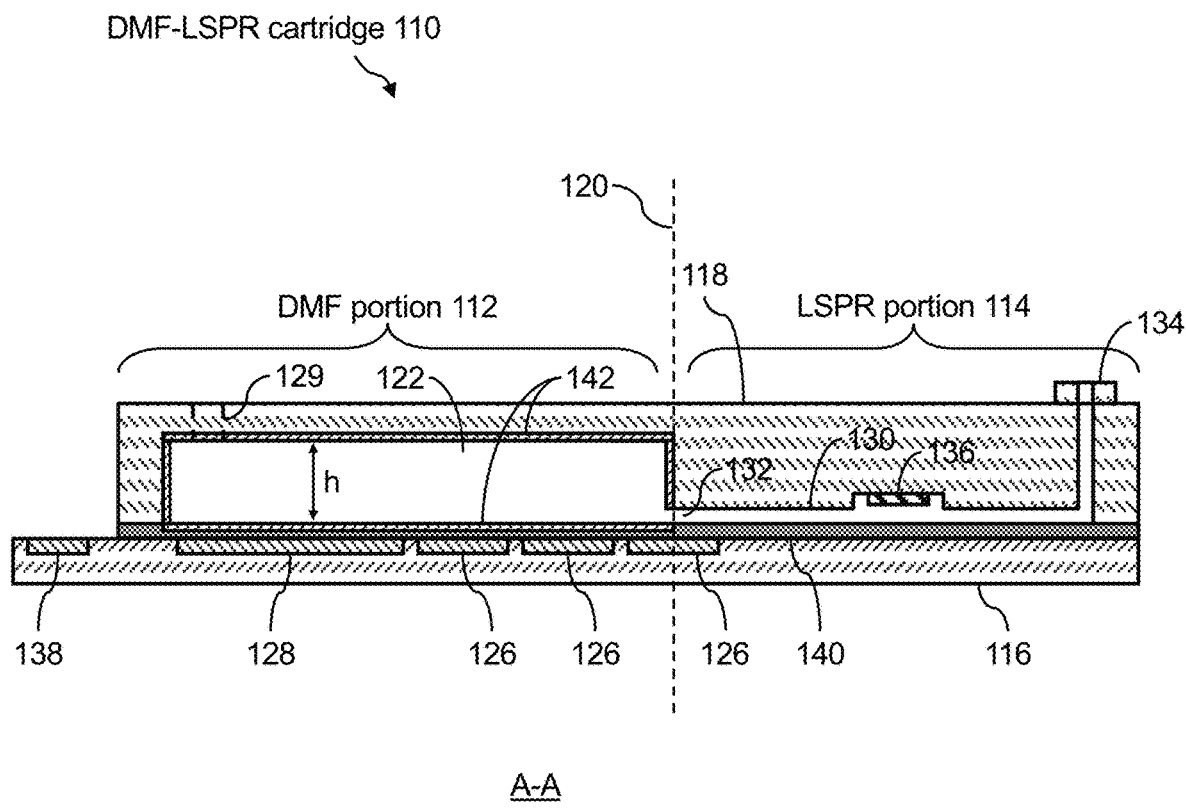
FIG. 3 is a simplified cross-sectional view of the single-channel DMF-LSPR cartridge shown in FIG. 2.

FIG. 2 is a perspective view of an example of a single-channel DMF-LSPR cartridge 110. Further, FIG. 3 is a simplified cross-sectional view of the single-channel DMF-LSPR cartridge 110 taken along line A-A of FIG. 2. In PR system 100, "single-channel" means one LSPR sensor only in the DMF-LSPR cartridge 110.

Single-channel DMF-LSPR cartridge 110 may include a bottom substrate 116 and a top substrate 118. In one example, bottom substrate 116 may be a material that is substantially transparent to white light, such as glass, plastic, or a class of polymers known as thermoplastic elastomers (TPE). In another example, bottom substrate 116 may be a printed circuit board (PCB) that is substantially transparent or one that may include holes or openings that allow light transmission. Further, a set of electrical contacts 138 may be provided on one end of bottom substrate 116. The electrical contacts 138 may be operatively interfaced with droplet operations electrodes 126 and reservoir electrodes 128 to facilitate control of the operation thereof (e.g., by way of traces or other electrically conductive material provided between the electrical contacts 138 and the droplet operations electrodes 126 and reservoir electrodes 128). In this regard, electrical contacts 138 may be used, for example, to connect to DMF interface 152, and then to controller 150. Like bottom substrate 116, top substrate 118 may be formed of a material that is substantially transparent to white light, such as glass, plastic, or TPE. Further, the inner surface of top substrate 118 may be coated with indium tin oxide (ITO).

The terms "top," "bottom," "over," "under," "in," and "on" are used throughout the description with reference to the relative positions of components of the DMF-LSPR cartridge, such as relative positions of top and bottom substrates of the DMF-LSPR cartridge. It will be appreciated that the DMF-LSPR cartridge is functional regardless of its orientation in space.

One area of bottom substrate 116 and top substrate 118 may be designated the DMF portion 112 and another area may be designated the LSPR portion 114. An interface 120 indicates the boundary between DMF portion 112 and LSPR portion 114. While the interface 120 is depicted as extending in a single plane relative to the DMF-LSPR cartridge 110 between the DMF portion 112 and the LSPR portion 114, it may be appreciated that the interface 120 may otherwise extend between the DMF portion 112 and the LSPR portion 114 (e.g., such that the DMF portion 112 may extend on multiple sides of the LSPR portion 114 or in multiple planes between the DMF portion 112 and the LSPR portion 114). In DMF portion 112 of single-channel DMF-LSPR cartridge 110, a reaction (or assay) chamber 122 may be provided between bottom substrate 116 and top substrate 118. Reaction (or assay) chamber 122 may be a space between bottom substrate 116 and top substrate 118 for processing any fluids of interest via droplet operations; fluids, such as, but not limited to, liquid reagents, buffer solution, sample fluid, and the like. Accordingly, an electrode arrangement 124 may be provided atop bottom substrate 116 in the reaction (or assay) chamber 122. Electrode arrangement 124 may include, for example, any arrangement of droplet operations electrodes 126 (e.g., electrowetting electrodes) and reservoir electrodes 128. Electrode arrangement 124 may include any lines of droplet operations electrodes 126 in relation to any number of reservoir electrodes 128. Further, certain lines of droplet operations electrodes 126 may terminate at interface 120 of single-channel DMF-LSPR cartridge 110. Accordingly, any end droplet operations electrode 126 at and/or spanning interface 120 is hereafter referred to as a boundary droplet operations electrode 126. Further, interface 120 may be considered the digital-to-analog boundary of DMF portion 112 and LSPR portion 114 of DMF-LSPR cartridge 110.

Electrode arrangement 124 is used for performing droplet operations via electrowetting. Examples of suitable electrode configurations are described in Pollack et al., U.S. Pat. No. 8,394,249, granted on Mar. 12, 2013; Shenderov and Pollack U.S. Pat. No. 9,216,415, granted on Dec. 22, 2015; and Srinivasan et al., U.S. Pat. No. 8,562,807, granted on Oct. 22, 2013, the disclosures of which are incorporated herein by reference.

"Droplet operation" may include any manipulation of a droplet on a digital fluidics device or cartridge. A droplet operation may, for example, include: loading a droplet into the digital fluidics device; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. Further, for controlling the temperature of processes occurring in reaction (or assay) chamber 122 and/or at LSPR sensor 136, a temperature control element (not shown), such as a Peltier heat pump, may be used in combination with DMF-LSPR cartridge 110.

Further, while FIG. 2 describes the DMF portion 112 of DMF-LSPR cartridge 110 as manipulating droplets via electrowetting methods (e.g., using droplet operations electrodes 126), this is exemplary only. In other examples, droplets may be manipulated in DMF portion 112 of DMF-LSPR cartridge 110 via other methods, such as, but not limited to, optical methods, magnetic methods, thermocapillary methods, surface acoustic wave methods, and the like, and any combinations thereof.

In single-channel DMF-LSPR cartridge 110, the one boundary droplet operations electrode 126 of DMF portion 112 may supply a fluid channel 130 of LSPR portion 114. Accordingly, an inlet 132 of fluid channel 130 may extend to the boundary droplet operations electrode 126. From inlet 132, fluid channel 130 may extend some length along LSPR portion 114 to an outlet 134. The LSPR sensor 136 may be provided along fluid channel 130 in any location between inlet 132 and outlet 134. While FIG. 3 (and subsequent drawings) show LSPR sensor 136 about midway between inlet 132 and outlet 134 of fluid channel 130, in certain examples it may be preferable that LSPR sensor 136 be arranged in close proximity to inlet 132 of fluid channel 130.

The LSPR sensor 136 may be provided along fluid channel 130 may be provided in an expanded region of fluid channel 130. In some examples the expanded region is a circular or ovular disk-shaped region, but it will be appreciated that a variety of shapes is possible. Generally, the dimensions of fluid channel 130 may be microchannel sized in order to keep volume consumption low. Additionally, the width of fluid channel 130 should be less than the width of boundary droplet operations electrode 126. In one example, fluid channel 130 may be from about 50 µm to about 1000 µm wide (side-to-side) and from about 25 µm to about 200 µm high (or deep, top to bottom). In another example, fluid channel 130 may be about 100 µm wide and about 50 µm high (or deep), while the expanded region of the LSPR sensor 136 (see FIG. 3) has a cross-section of about 300 µm and the LSPR sensor 136 is situated on a top or bottom surface of the expanded region and has a cross-section of about 200 µm. The LSPR sensor 136 may be shaped to fit in the expanded region, e.g., in the case of a circular or ovular disk-shaped region, the surface of the LSPR sensor 136 may be ovular or circular. It will be appreciated that other shapes are possible. Additionally, in other examples, it may be beneficial to taper the height h (see FIG. 3) of reaction (or assay) chamber 122 to a preferred height (or depth) of fluid channel 130.

Referring now specifically to FIG. 3, a dielectric layer 140 may be provided atop bottom substrate 116 and electrode arrangement 124. Further, the surfaces of reaction (or assay) chamber 122 may be coated with a hydrophobic layer 142. Reaction (or assay) chamber 122 may have a height h, which may vary in different examples. It will be appreciated that height h may vary depending on electrode size and droplet size. Height h may be any height that permits droplet operations to be affected in chamber 122. In one example, the height h may be about 300 µm. The area of reaction (or assay) chamber 122 may vary depending on the design of electrode arrangement 124. Further, in one example, each of the droplet operations electrodes 126 may be substantially square, such as about 2 mm on a side. Similarly, in one example, each of the reservoir electrodes 128 may be substantially square, such as from about 6 mm to about 10 mm on a side. However, the shape and size of droplet operations electrodes 126 and reservoir electrodes 128 can vary in different examples. Further, associated with each reservoir electrode 128 may be a reservoir inlet 129 through top substrate 118 wherein a reservoir inlet 129 may be used for loading the reservoir with fluid.

The general dimensions of fluid channel 130 may be microchannel sized in order to keep volume consumption low. Additionally, the width of fluid channel 130 should be less than the width of boundary droplet operations electrode 126. In one example, fluid channel 130 may be from about 50 µm to about 1000 µm wide and from about 25 µm to about 200 µm high (or deep). In another example, fluid channel 130 may be about 100 µm wide and about 50 µm high (or deep). Additionally, in other examples, it may be beneficial to taper the height h of reaction (or assay) chamber 122 to a preferred height (or depth) of fluid channel 130.

Figure 4:
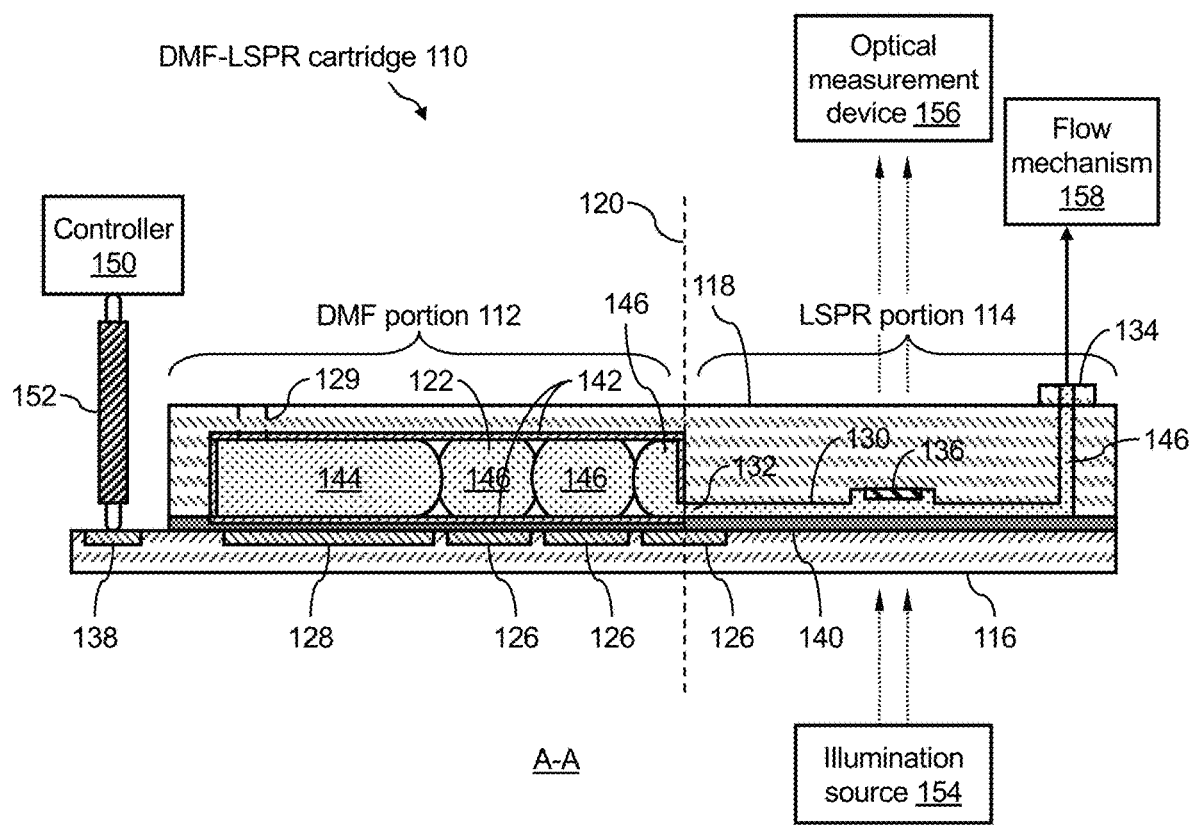
FIG. 4 shows the portion of the single-channel DMF-LSPR cartridge shown in FIG. 3 in relation to certain components of the presently disclosed PR system.

FIG. 4 illustrates the portion of single-channel DMF-LSPR cartridge 110 shown in FIG. 3 in relation to certain components of PR system 100 shown in FIG. 1 and when processing liquids therein. Controller 150 may be electrically connected to electrical contacts 138 via DMF interface 152, which may be, for example, but not limited to, connection pins. Again, controller 150 may control droplet manipulation by activating/deactivating droplet operations electrodes 126 and/or reservoir electrodes 128 (e.g., by providing electrical signals to the electrical contacts 138 which are in operative communication with the droplet operations electrodes 126 and/or reservoir electrodes 128). Further, flow mechanism 158 may be fluidly coupled to outlet 134 of fluid channel 130 of LSPR portion 114 of single-channel DMF-LSPR cartridge 110. In one example, flow mechanism 158 may be capable of providing a volumetric flow rate in fluid channel 130 of from about 1 µl/min to about 1000 µl/min.

Further, illumination source 154 and optical measurement device 156 (e.g., a spectrometer) may be arranged with respect to LSPR sensor 136 of LSPR portion 114. Illumination source 154 may be arranged on one side of single-channel DMF-LSPR cartridge 110 and optical measurement device 156 may be arranged on the other side of single-channel DMF-LSPR cartridge 110. In this configuration, white light from illumination source 154 may be directed at and pass through LSPR sensor 136. Then, optical measurement device 156 may capture the optical signal emitted from LSPR sensor 136.

In operation, a quantity of fluid 144 (e.g., liquid reagents, buffer solution, sample fluid) may be provided atop a certain reservoir electrode 128. Then, droplets 146 may be dispensed via droplet operations from the reservoir electrode 128 to a line of droplet operations electrodes 126. The fluid 144 and/or droplets 146 may contain, for example, target analytes for binding to LSPR sensor 136. Accordingly, illumination source 154 and optical measurement device 156 may provide a simple optical detection system for determining the degree of binding at LSPR sensor 136.

In reaction (or assay) chamber 122, the space surrounding fluid 144 and droplets 146 may be filled with, for example, air or filler fluid (e.g., a low-viscosity oil, such as silicone oil or hexadecane filler fluid). Further, droplets 146 may, for example, be aqueous or non-aqueous, or may be mixtures or emulsions including aqueous and non-aqueous components, or may be oil-covered droplets (i.e., droplet oil-shell configuration). In the example shown in FIG. 4, fluid 144 and droplets 146 may be surrounded by air or another gas or gas mixture. Droplets 146 may be transported via droplet operations along the droplet operations electrodes 126. Droplets 146 may be transported at a rate that generally allows continuous replenishing of the solution at inlet 132 of fluid channel 130 and thus preventing air to enter fluid channel 130. When fluid 146 reaches boundary droplet operations electrode 126, the pulling force of flow mechanism 158 may act to pull the fluid 146 through inlet 132 and into fluid channel 130 of LSPR portion 114. Now fluid 146 may flow into fluid channel 130, across LSPR sensor 136, and to outlet 134 of fluid channel 130. While fluid 146 is at LSPR sensor 136, a detection operation may occur via illumination source 154 and optical measurement device 156. Optical measurement device 156 may continuously sample LSPR sensor 136 as fluid 146 flows across LSPR sensor 136.

While FIG. 2, FIG. 3, and FIG. 4 show that electrode arrangement 124 includes a boundary droplet operations electrode 126 that spans interface 120, this is exemplary only. In other examples of DMF-LSPR cartridge 110, the edge of the end droplet operations electrode 126 may substantially abut interface 120 without spanning or crossing over interface 120.

In PR system 100, the digital microfluidics capability of DMF portion 112 of DMF-LSPR cartridge 110 facilitates certain advantages as compared with standard SPR systems. Examples of these advantages include, but are not limited to, (1) flexibility to iterate through thousands of different experimental conditions; (2) extremely small sample volumes (about 1/100th of current technology); (3) complete automation of entire assay, (4) minimal maintenance as no pumps, valves, or tubes needed; (4) little or no clogging, leaking, or contamination possible; (5) very compatible with SPR requirements; (6) ideal for multiplexing hundreds of samples; (7) low cost of hardware; and (8) very fast switching, which is key for good SPR data.

In DMF-LSPR cartridge 110, in order for the LSPR sensor 136 to measure the binding rate and not the mass transport rate of an analyte in fluid 146 in fluid channel 130, the velocity of fluid 146 moving through fluid channel 130 may be sufficiently high such that the mass transport rate is higher than the binding rate. The velocity of fluid 146 may be sufficiently high to create momentum of the molecules (e.g., the analytes) to the surface of LSPR sensor 136. Again, using flow mechanism 158, the volumetric flow rate in fluid channel 130 may be maintained at a rate ranging from about 1 µl/min to about 1000 µl/min. Further, because the binding rate may vary depending on the application, the flow velocity may be adjusted by various means. For example, the flow velocity may be increased by using a lower pressure (via flow mechanism 158) to move fluid 146 at a higher velocity, or by making the channel cross section smaller. Further, other mechanisms may be used to assist flow, such as, but not limited to, vibration force applied locally at the LSPR sensor or vibration force applied to the entirety of DMF-LSPR cartridge 110. Fluid channel 130 may take any path or line through LSPR portion 114 and may have any desired cross-sectional area and length. Accordingly, in the presently disclosed DMF-LSPR cartridge 110 the diffusion or flow rate may be faster than the binding rate and thereby facilitating the LSPR sensor 136 to measure the binding rate and not the diffusion or flow rate. More details of examples of the binding rate are shown and described hereinbelow with reference to FIG. 10 through FIG. 14.

In LSPR portion 114 of single-channel DMF-LSPR cartridge 110, the arrangement of illumination source 154, LSPR sensor 136, and optical measurement device 156 may provide an optical detection system that operates in transmission mode.

As described herein, "localized surface plasmon resonance (LSPR)" may include using nanoparticle-based or nanostructure-based transducers to monitor binding events in real time without additional labels. For example, nanoparticle-based transducers may include metal nanoparticles from about 1 nm to about 1000 nm in various dimensions. For example, nanostructure-based transducers may include gold film that may include nano-sized features (e.g., nano-sized bumps, posts, ridges, lines, and the like.) Some nanoparticle-based or nanostructure-based diagnostic assays are "label-free."

LSPR is a phenomenon associated with noble metal nanoparticles that creates sharp spectral absorbance and scattering peaks and produces strong electromagnetic near-field enhancements. These spectral peaks can be monitored using absorbance spectroscopy. The spectral peak changes with refractive index changes in the immediate vicinity of the nanoparticle surface. When chemical targets are bound near the surface of a metal nanoparticle, a shift in the spectral peak occurs due to changes in the local refractive index. This can be used to determine the concentration of a specific target in a complex medium.

LSPR sensors may operate through the immobilization of metal nanoparticles onto a solid support that can include, for example, a flat surface or a microstructured surface. The nanoparticles are functionalized with specific capture molecules, which may be an antibody. The sample fluid of interest is flowed over the top of the metal nanoparticles, the target chemicals of interest bind to their respective capture molecules, and the overall spectral peak of the sensor shifts according to the concentration of the chemical target on the capture molecules. LSPR sensors with nanoparticles on planar surfaces operate by flowing the sample longitudinally over the surface. In order to measure this shift, reflectance or transmission absorbance spectroscopy may be employed. More details of examples of LSPR sensors are shown and described hereinbelow with reference to FIG. 5 through FIG. 7G.

Figure 5:
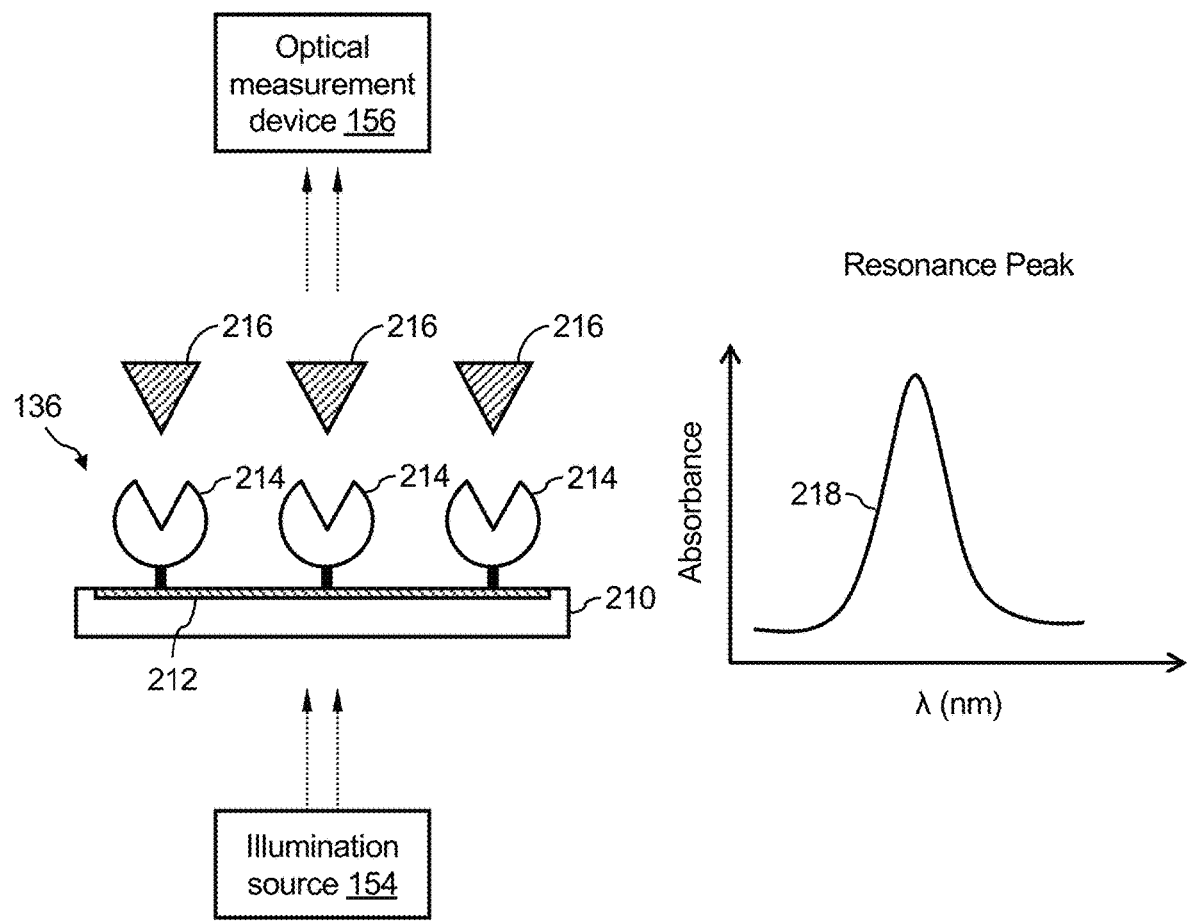
FIG. 5 and FIG. 6 show schematic views of an example of an LSPR sensor of the presently disclosed DMF-LSPR cartridge for analysis of analytes.
Figure 6:
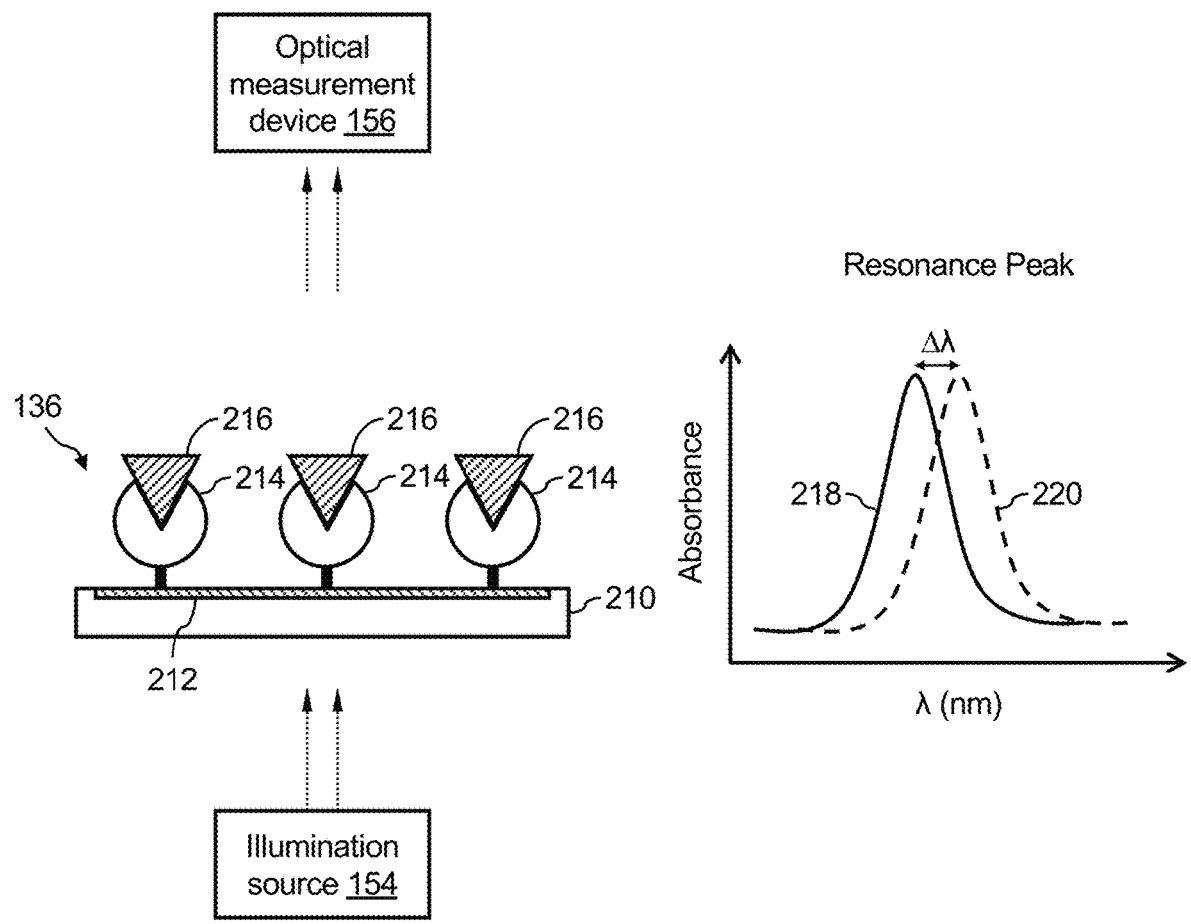

FIG. 5 and FIG. 6 show schematic views of an example of LSPR sensor 136 of the presently disclosed DMF-LSPR cartridge 110 for analysis of analytes. Generally, LSPR may include label-free interaction analysis in real-time. However, LSPR may also be used with labels to enhance the signal. The basic structure of the assay may include a sensor chip (e.g., LSPR sensor 136) that may include a glass or plastic substrate with a surface that produces LSPR, such as a collection of discrete nanostructures distributed on a surface, or a continuous film that has nano-sized features formed therein, as shown, for example, in FIG. 7A through FIG. 7G. Then, one of two binding partners may be immobilized on the surface of the sensor. In LSPR, the "ligand" may refer to the binding partner that is immobilized on the surface of the sensor. The "analyte" may refer to what flows in solution over the ligand on the surface of the sensor. When the analyte binds to the ligand, it changes the optical properties of the surface of the sensor, which is measurable in real time.

Depending on the contemplated application, a LSPR sensor 136 may include a substantially transparent or an opaque substrate 210. These substrates may include a glass, plastic, or TPE substrate. Substrate 210 may be substantially transparent when used in a transmission mode configuration. By contrast, substrate 210 may be opaque when used in a reflection mode configuration. An LSPR sensor layer 212 may be provided atop substrate 210. LSPR sensor layer 212 may be, for example, a gold film that may include certain nanostructures that create an LSPR effect, such as those shown in in FIG. 7A through FIG. 7G. LSPR sensor layer 212 may be functionalized with one or more capture molecules 214. In one example, capture molecules 214 are ligands that are immobilized on the surface of LSPR sensor layer 212. In this example, the ligands may include one of two binding partners, the other binding partner being a target analyte 216 wherein the target analyte 216 may flow in solution over the capture molecules 214 as shown in FIG. 5. By contrast, FIG. 6 shows the target analytes 216 binding to capture molecules 214. This binding may be referred to as a binding event.

Referring now again to FIG. 5, a plot 218 is provided that indicates the optical absorbance peak of LSPR sensor layer 212 prior to a binding event occurring. That is, plot 218 shows the peak position or intensity prior to target analytes 216 binding to capture molecules 214 in LSPR sensor 136. Referring now to FIG. 6, the change in peak position or intensity that is induced by binding of the target analytes 216 to the capture molecules 214 may be monitored in real time. For example, monitoring or analysis of the optical absorbance peak may include comparing the peak position prior to binding (i.e., plot 218) with the peak position after binding (i.e., a plot 220). Generally, in LSPR sensor 136, as analytes bind to the surface, the resonance peak of the light will shift to a higher wavelength, which is measurable in real time.

Figure 7A:
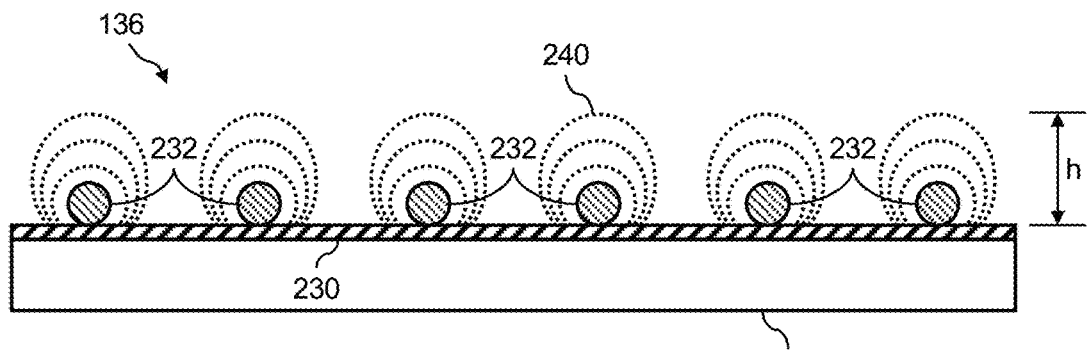
FIG. 7A, FIG. 7B, and FIG. 7C show side views of other examples of an LSPR sensor of the presently disclosed DMF-LSPR cartridge for analysis of analytes.
Figure 7B:
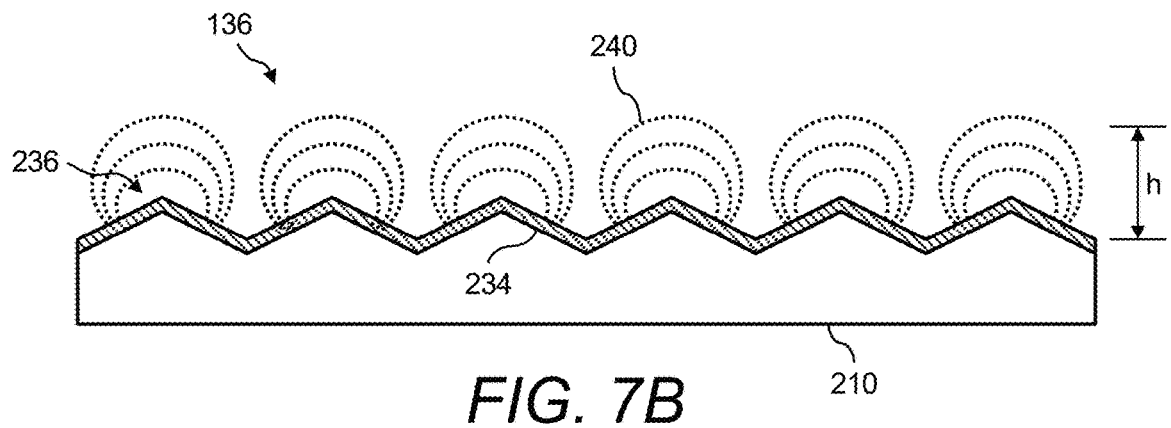
Figure 7C:
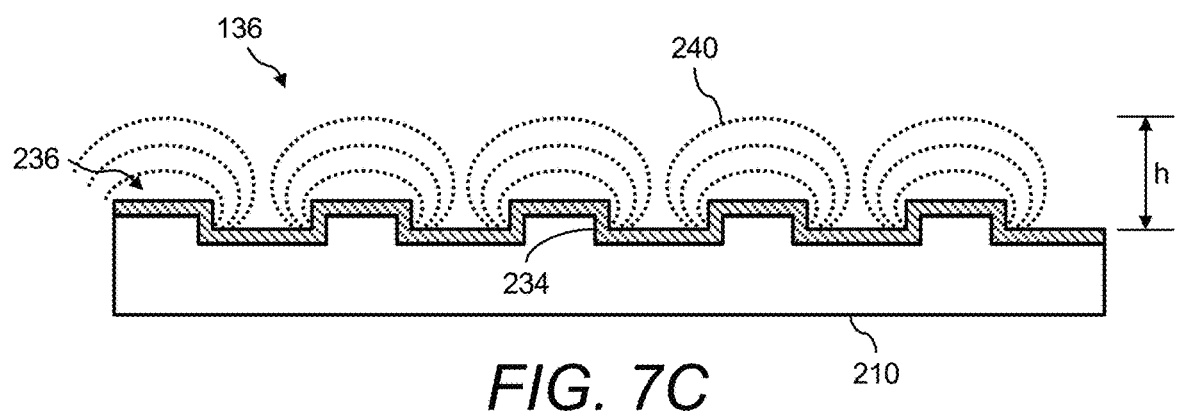

Referring now to FIG. 7A, FIG. 7B, and FIG. 7C, various examples of LSPR sensors are provided wherein the LSPR sensor layer may include nanostructures that can produce LSPR. For example, FIG. 7A shows a side view of an LSPR sensor 136 that may include colloidal-shaped nanostructures. LSPR sensor 136 may include a substantially transparent substrate 210, such as a glass, plastic, or TPE substrate. Next, an adhesive layer 230 may be provided atop substrate 210. Next, an array or arrangement of nanoparticles 232 may be provided on the surface of adhesive layer 230. In one example, nanoparticles 232 may be metal nanoparticles, such as gold nanoparticles, that are immobilized on or linked to substrate 210 using physical or chemical coupling, such as using adhesive layer 230. Nanoparticles 232 may be, for example, from about 1 nm to about 1000 nm in various dimensions and in various shapes, such as spheres, stars, rice, cubes, cages, urchins, rods, and the like. Next, capture molecules 214 (not shown) as described in FIG. 5 and FIG. 6 may be immobilized on nanoparticles 232.

By contrast, FIG. 7B and FIG. 7C show various examples of LSPR sensors 136 that may be formed using nanograting technology. LSPR sensors 136 of FIG. 7B and FIG. 7C may include a substantially transparent substrate 210 that is patterned with a certain nanograting pattern. Substrate 210 may be formed of, for example, glass, plastic, TPE, cured epoxy, and the like. In another example, substrate 210 may be a substantially transparent PCB, such as a substantially transparent ceramic PCB. Then, a LSPR sensor layer 234 may be provided atop the grated substrate 210. LSPR sensor layer 234 may be a thin gold film that is deposited on the grated substrate 210. The result may include a surface with certain nano-features 236 thereon. A glass substrate 210 may be patterned, for example, using a standard photolithography process and etching. A TPE substrate 210 may be patterned, for example, using an embossing process. In other examples, LSPR sensors 136 may be substantially transparent or can include colored, opaque, or translucent substrates and/or dielectric materials, such as, but not limited to, substrates that include clear Kapton, orange Kapton, or glass as a dielectric.

In the example shown in FIG. 7B, LSPR sensor 136 is patterned to provide certain sawtooth-shaped nano-features 236. LSPR sensor layer 234 may include certain peaks and certain valleys. In one example, the peaks and valleys of sawtooth-shaped nano-features 236 may be provided on about a 1300 nm pitch. Further, the valleys may be, for example, about 55 nm deep. Next, capture molecules 214 (not shown) as described in FIG. 5 and FIG. 6 may be immobilized on LSPR sensor layer 234 that has the sawtooth (or triangle) topology.

In the example shown in FIG. 7C, LSPR sensor 136 is patterned to provide certain square wave-shaped nano-features 236. LSPR sensor layer 234 may have certain plateaus and certain troughs. In one example, each plateau and each trough may be about 700 nm wide, for an overall pitch of about 1400 nm. Further, the troughs may be, for example, about 55 nm deep. Next, capture molecules 214 (not shown) as described in FIG. 5 and FIG. 6 may be immobilized on LSPR sensor layer 234 that has the square wave topology. With respect to the LSPR sensors 136 shown in FIG. 7B and FIG. 7C, a simple fabrication process may be used for LSPR portion 114 of DMF-LSPR cartridge 110. The sawtooth-shaped nano-features and/or the square wave-shaped nano-features may be formed directly into fluid channel 130 or any microfluidics channel. The gold coating may be added atop the embossed features. In so doing, a good LSPR effect may be created using one fabrication step that is highly repeatable and consistent. Further, the nano-features may be formed in either the top substrate 118 or bottom substrate 116.

Referring now again to the LSPR sensors 136 shown in FIG. 7A, FIG. 7B, and FIG. 7C, each may emit an optical signal 240 that is present very close to the surface. In one example, the LSPR optical signal 240 may be detected within from about 0 nm to about 100 nm from the surface. In comparison, the optical signals of standard SPR sensors may be detected up to about 1000 nm from the surface. In both LSPR and SPR the measurement signal is a combination of the binding component and the bulk component. However, due to longer decay length of SPR and consequently higher bulk refractive index sensitivity, SPR is more affected by the bulk than LSPR, requiring more control over temperature which affects refractive index of the bulk solution. Consequently, standard SPR sensors are subject to a large bulk effect whereas LSPR sensors have a small bulk effect.

Figure 7D:
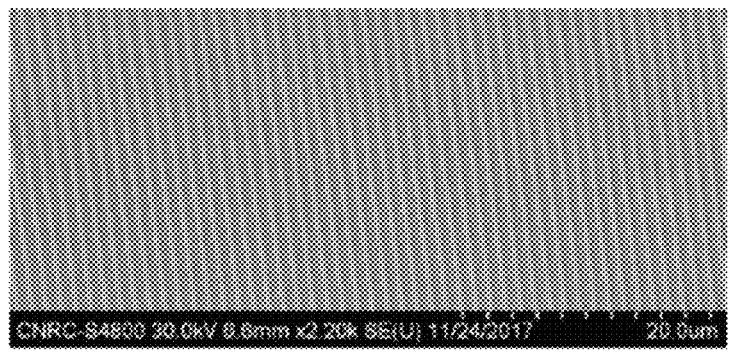
FIGS. 7D, 7E, 7F, and 7G show examples of an LSPR sensor of the presently disclosed DMF-LSPR cartridge.
Figure 7D:
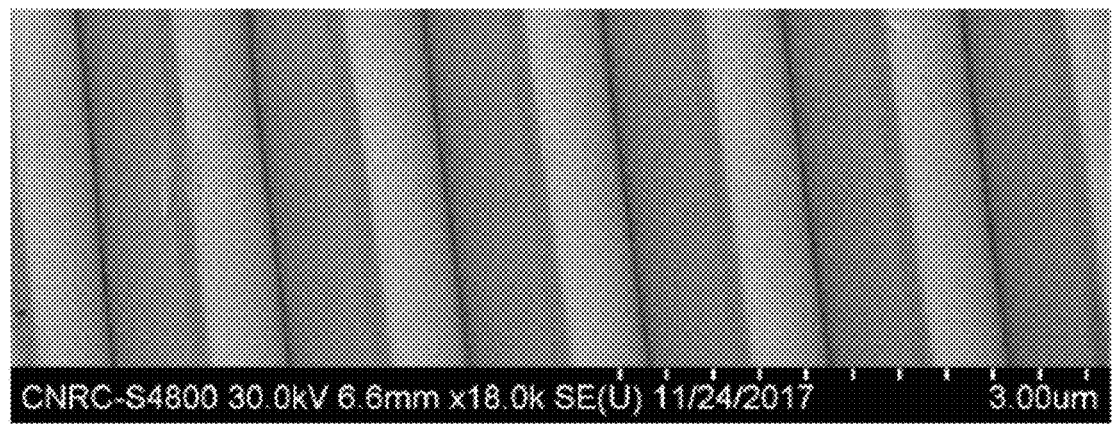
Figure 7D:
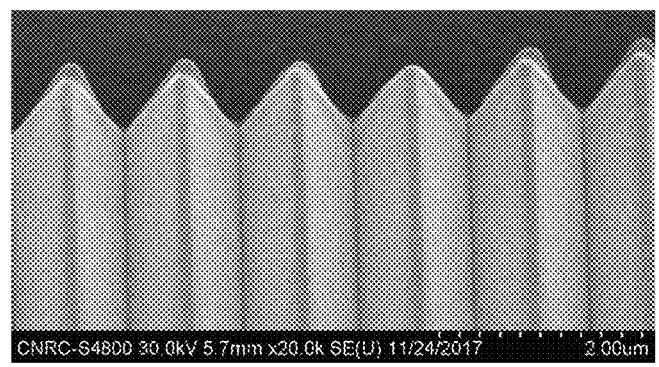
Figure 7E:
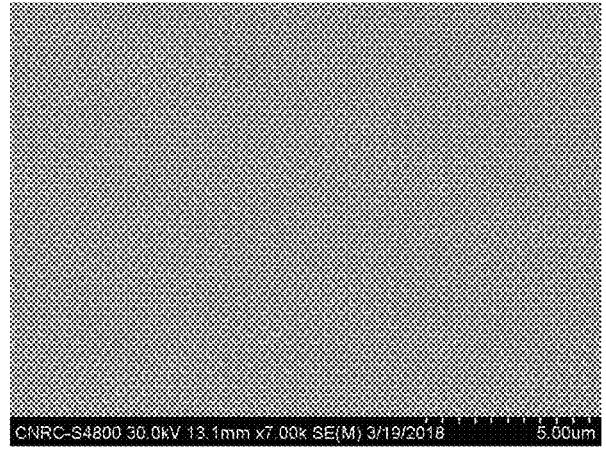
Figure 7E:
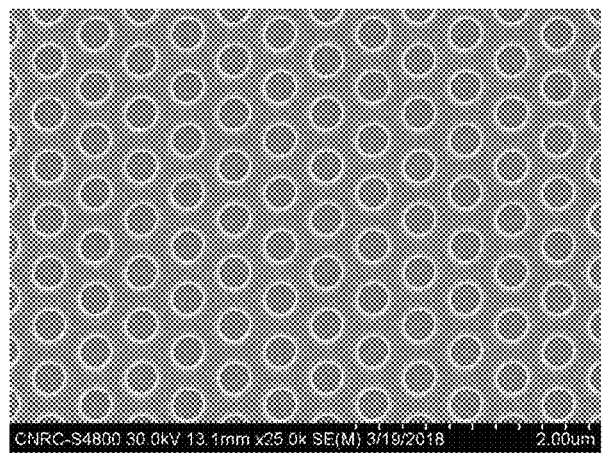
Figure 7E:
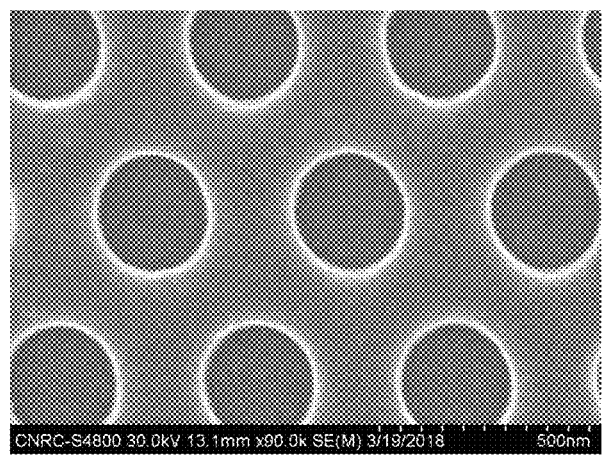
Figure 7F:
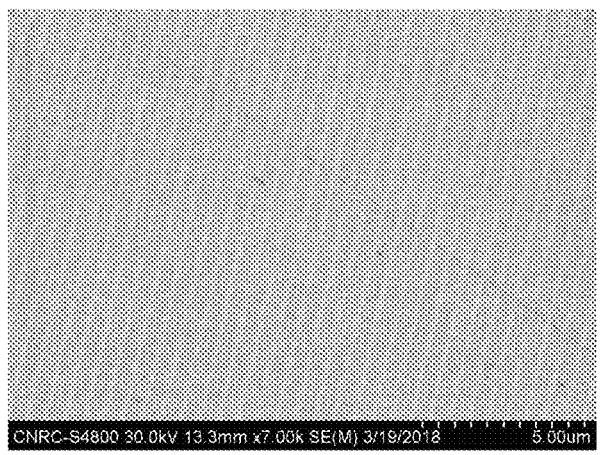
Figure 7F:
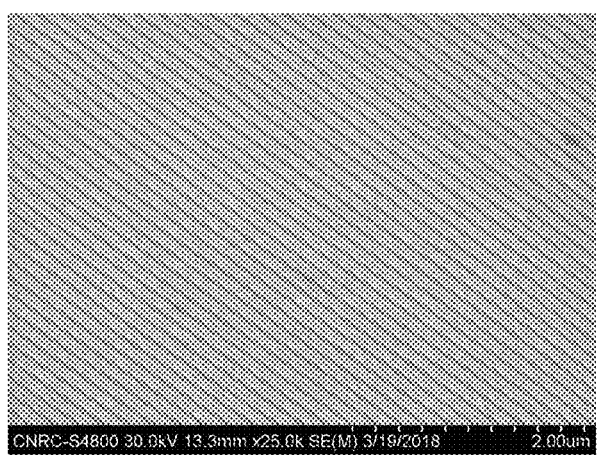
Figure 7F:
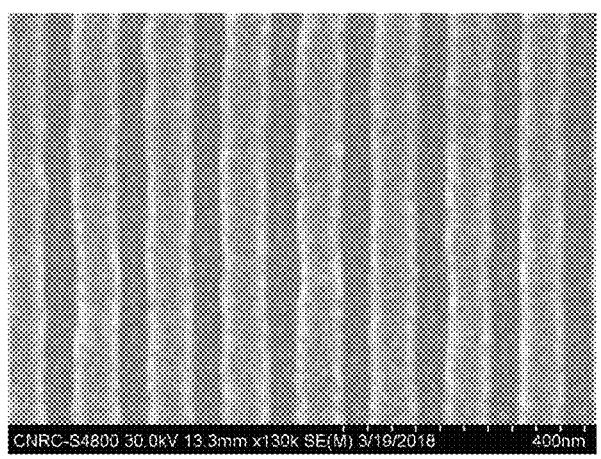
Figure 7G:
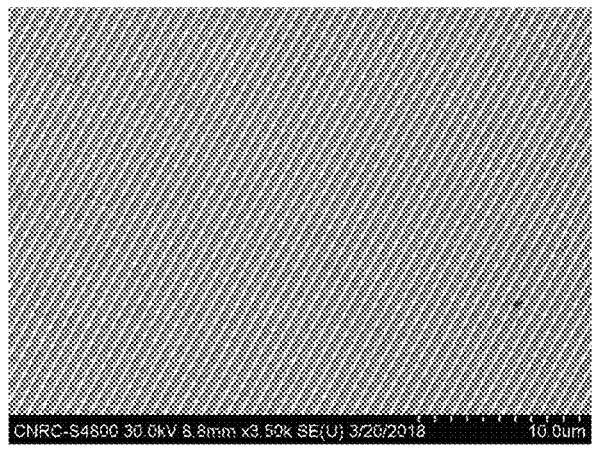
Figure 7G:
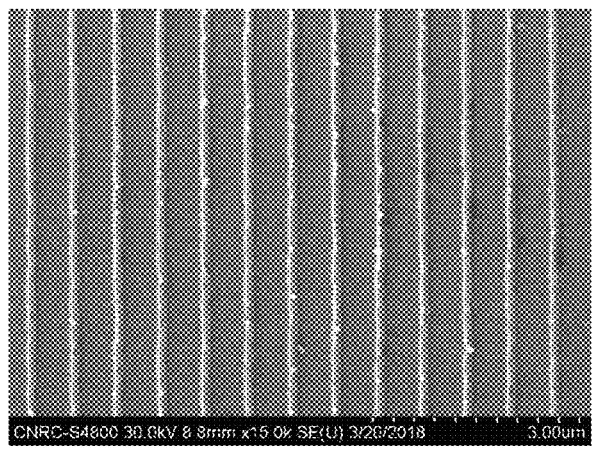
Figure 7G:
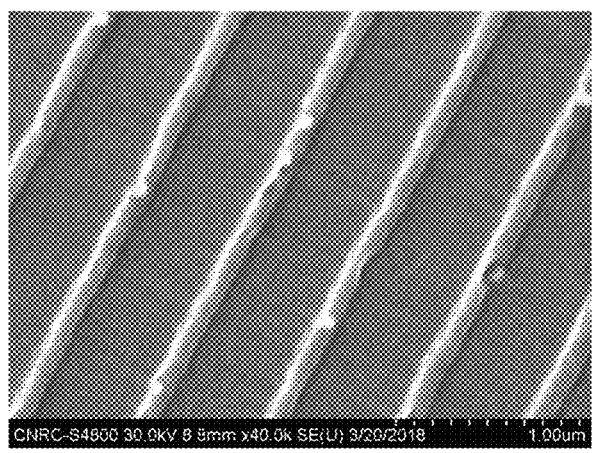

Referring now to FIG. 7D, FIG. 7E, FIG. 7F, and FIG. 7G, images of other examples of grating structures are depicted that may be suitable to provide the LSPR effect in the LSPR sensors (e.g., LSPR sensor 136) of LSPR portion 114 of DMF-LSPR cartridge 110. FIG. 7D shows an example of a 1300 nm pitch triangle grating 250 at various magnifications. FIG. 7E shows an example of a 520 nm pitch hexagonal holes grating 252 at various magnifications. FIG. 7F shows an example of a 140 nm pitch linear grating 254 at various magnifications. FIG. 7G shows an example of a 700 nm pitch linear blazed grating 256 at various magnifications.

In PR system 100, the LSPR sensors (e.g., LSPR sensor 136) of LSPR portion 114 of DMF-LSPR cartridge 110 facilitates certain advantages as compared with standard SPR sensors. Examples of these advantages include, but are not limited to, (1) more simple and robust optics; (2) minimal background interference; for example, about 100× less sensitive to background; (3) high sensitivity; for example, about 50× more sensitive to binding events because the sensing volume is very small (i.e., can sense close to the surface, such as about 40 nm from the surface); (4) robust spectral shift data; and (5) no temperature control needed.

Figure 8A:
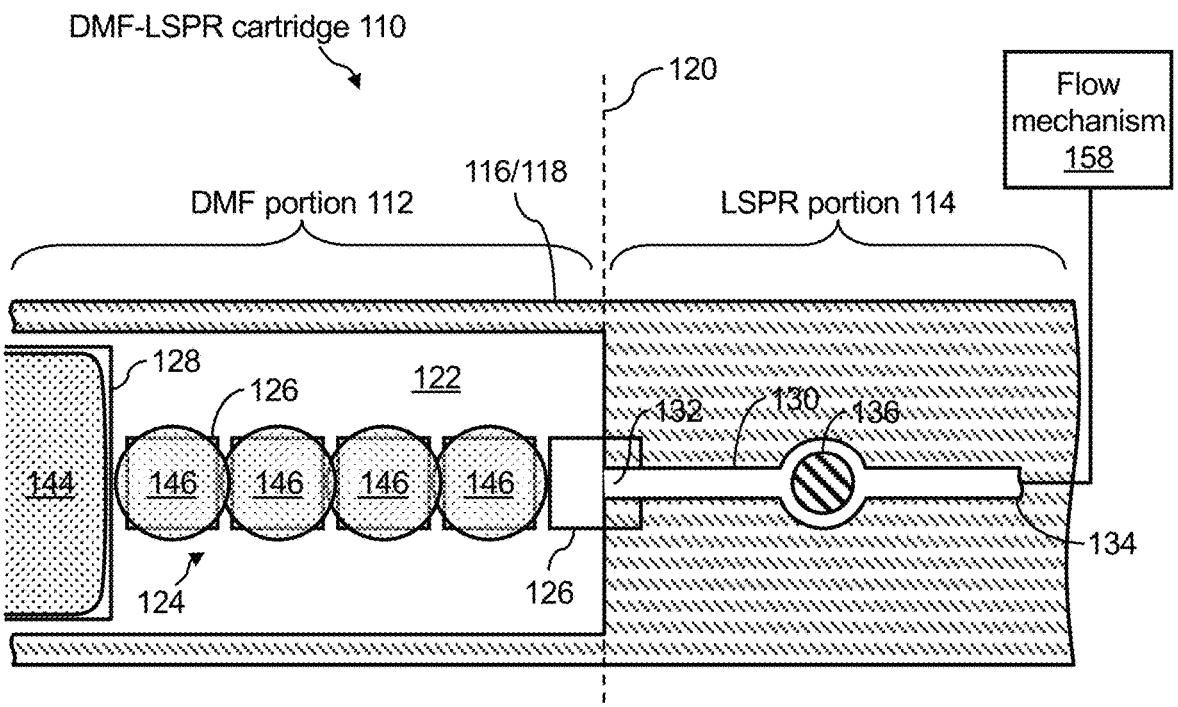
FIG. 8A through FIG. 8F illustrate various views of another example of a single-channel DMF-LSPR cartridge and an example of a process of using the single-channel DMF-LSPR cartridge for analysis of analytes.
Figure 8B:
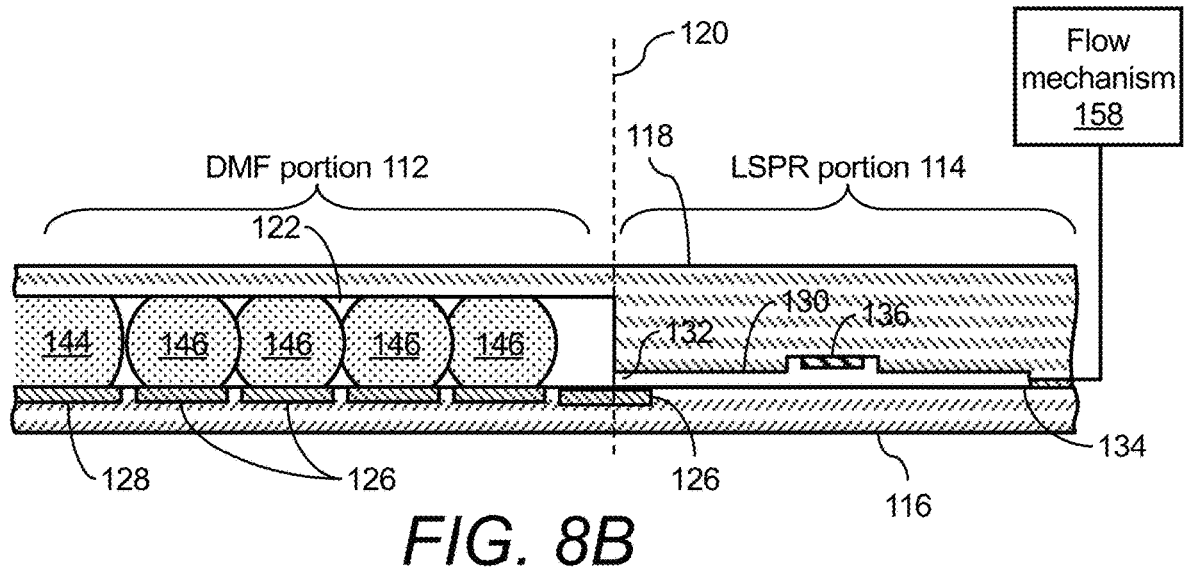

FIG. 8A through FIG. 8F illustrate various views of another example of a single-channel DMF-LSPR cartridge 110 and an example of a process of using the single-channel DMF-LSPR cartridge 110 for analysis of analytes. For example, FIG. 8A and FIG. 8B show a plan view and a side view, respectively, of fluid 144 at reservoir electrode 128 and droplets 146 being dispensed along the line of droplet operations electrodes 126. In this step, droplets 146 in DMF portion 112 have not yet entered fluid channel 130 of LSPR portion 114.

Figure 8C:
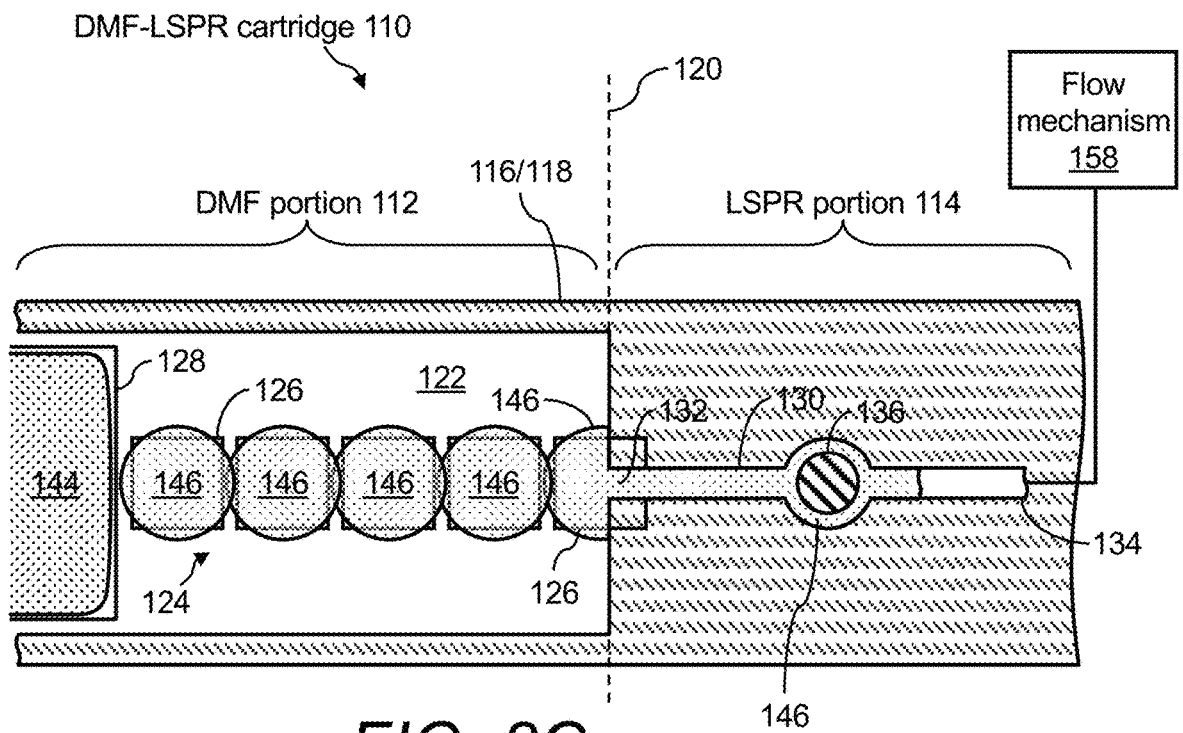
Figure 8D:
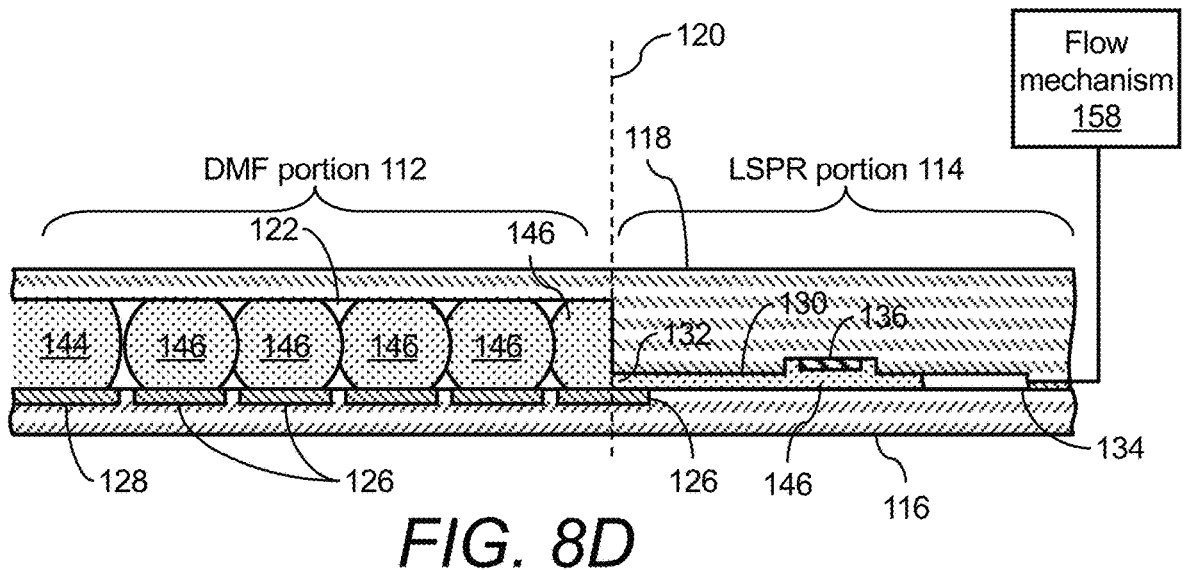

Next, FIG. 8C and FIG. 8D show a plan view and a side view, respectively, of a droplet 146 at boundary droplet operations electrode 126 and then crossing the boundary (i.e., interface 120) of DMF portion 112 and LSPR portion 114 of single-channel DMF-LSPR cartridge 110. In this step, fluid 146 is entering fluid channel 130 of LSPR portion 114 and flowing to LSPR sensor 136 with the assistance of flow mechanism 158.

Figure 8E:
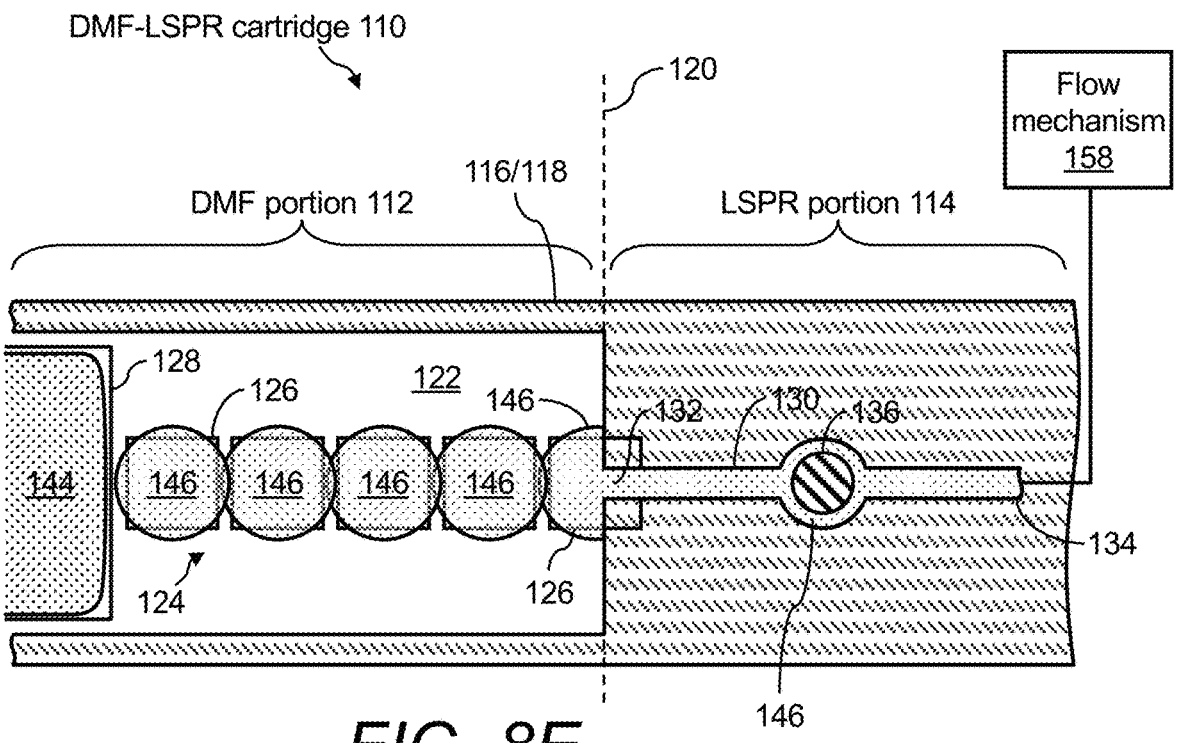
Figure 8F:
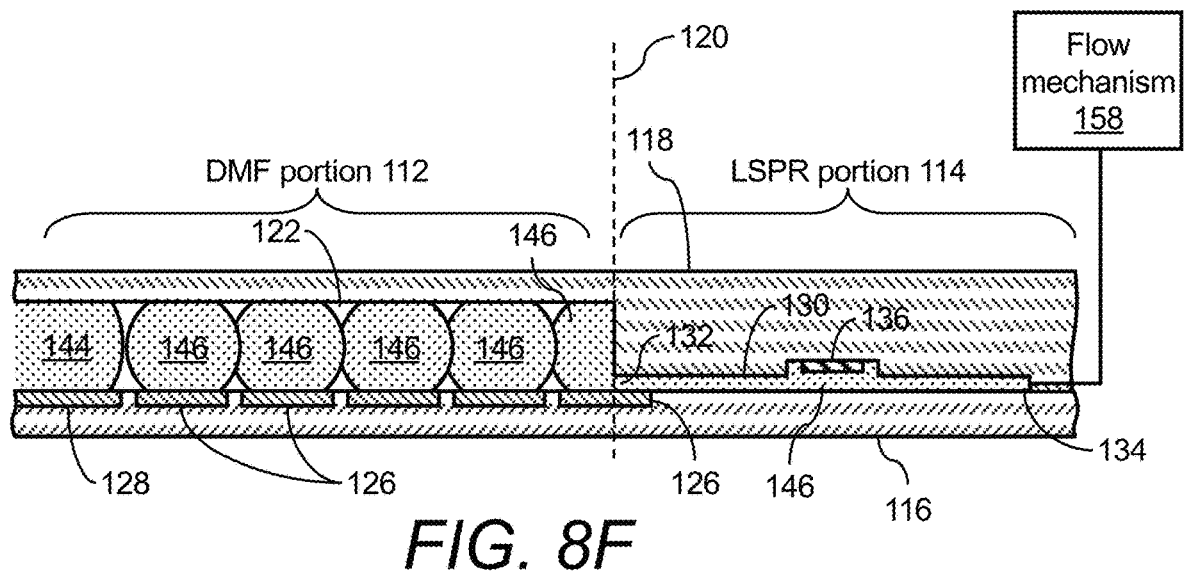

Next, FIG. 8E and FIG. 8F show a plan view and a side view, respectively, of the original droplet 146 entirely out of DMF portion 112 of single-channel DMF-LSPR cartridge 110 and fluid 146 now entirely filling fluid channel 130 of LSPR portion 114, again with the assistance of flow mechanism 158. In this step, the detection operation can occur using LSPR sensor 136, illumination source 154 (not shown), and optical measurement device 156 (not shown).

In the operation of any DMF-LSPR cartridge 110, such as shown in FIG. 8A through FIG. 8F, optical feedback (not shown) or electrical feedback (not shown) or both may be used to determine the position of the droplets 146 in DMF portion 112 of DMF-LSPR cartridge 110. This feedback may be used to ensure that the droplets 146 transported to the boundary (i.e., interface 120) are correctly timed. Namely, it is desirable that the next droplet 146 in line is moved to boundary droplet operations electrode 126 as the current droplet 146 nearly but not totally disappears into fluid channel 130 of LSPR portion 114. With no gap between droplets 146, air may be prevented from entering fluid channel 130. Accordingly, droplets 146 may be transported at a high rate along droplet operations electrode 126 such that a substantially continuous stream of fluid 146 is delivered to inlet 132 of fluid channel 130.

Further, the presently disclosed PR system 100 is not limited to the single-channel DMF-LSPR cartridges 110 shown in FIG. 2 through FIG. 8F. These are exemplary only. Any single-channel designs of DMF-LSPR cartridge 110 are possible within PR system 100.

Figure 9:
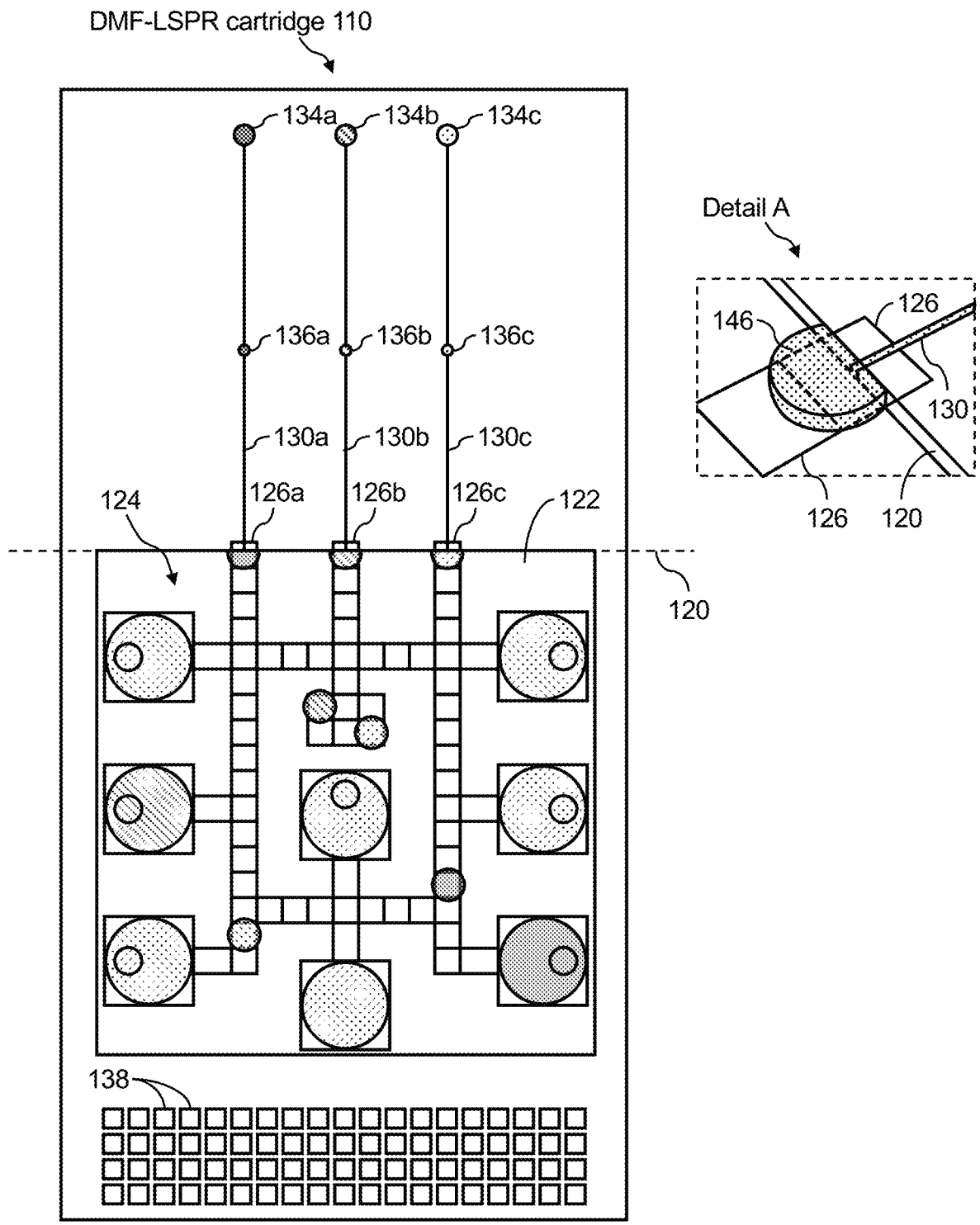
FIG. 9 is a plan view of a multiple-channel DMF-LSPR cartridge, which is another example of a DMF-LSPR cartridge of the presently disclosed PR system.

FIG. 9 is a plan view of an example of a multiple-channel DMF-LSPR cartridge 110. Multiple-channel DMF-LSPR cartridge 110 may include another example of electrode arrangement 124 wherein electrode arrangement 124 may include an arrangement of reservoir electrodes 128 and droplet operations electrodes 126 that support a plurality of fluid channels 130 such as three channels, meaning three separate fluid channels 130 (e.g., fluid channels 130a, 130b, 130c) and LSPR sensors 136 (e.g., LSPR sensors 136a, 136b, 136c).

In one example, PR system 100 may include only one illumination source 154 (not shown) that is used in common with LSPR sensors 136a, 136b, 136c of multiple-channel DMF-LSPR cartridge 110 and may include only one optical measurement device 156 (not shown) that is used in common with LSPR sensors 136a, 136b, 136c. In this example, the respective fluid channels 130 (e.g., fluid channels 130a, 130b, 130c) and LSPR sensors 136 (e.g., LSPR sensors 136a, 136b, 136c) may be operated in a synchronized manner.

In another example, PR system 100 may include three separate illumination sources 154 (not shown) and may include three separate optical measurement devices 156 (not shown) in combination with multiple-channel DMF-LSPR cartridge 110. That is, each of the LSPR sensors 136a, 136b, 136c may be provided a dedicated illumination source 154 (not shown) and optical measurement device 156 (not shown), respectively. In this example, the respective fluid channels 130 (e.g., fluid channels 130a, 130b, 130c) and LSPR sensors 136 (e.g., LSPR sensors 136a, 136b, 136c) may be operated independently.

Additionally, a Detail A of FIG. 9 shows more details of a droplet 146 crossing the boundary (i.e., interface 120) of DMF portion 112 and LSPR portion 114 of multiple-channel DMF-LSPR cartridge 110.

Further, the presently disclosed PR system 100 is not limited to the multiple-channel DMF-LSPR cartridge 110 shown in FIG. 9. This is exemplary only. Any multiple-channel designs of DMF-LSPR cartridge 110 are possible within PR system 100.

Figure 10:
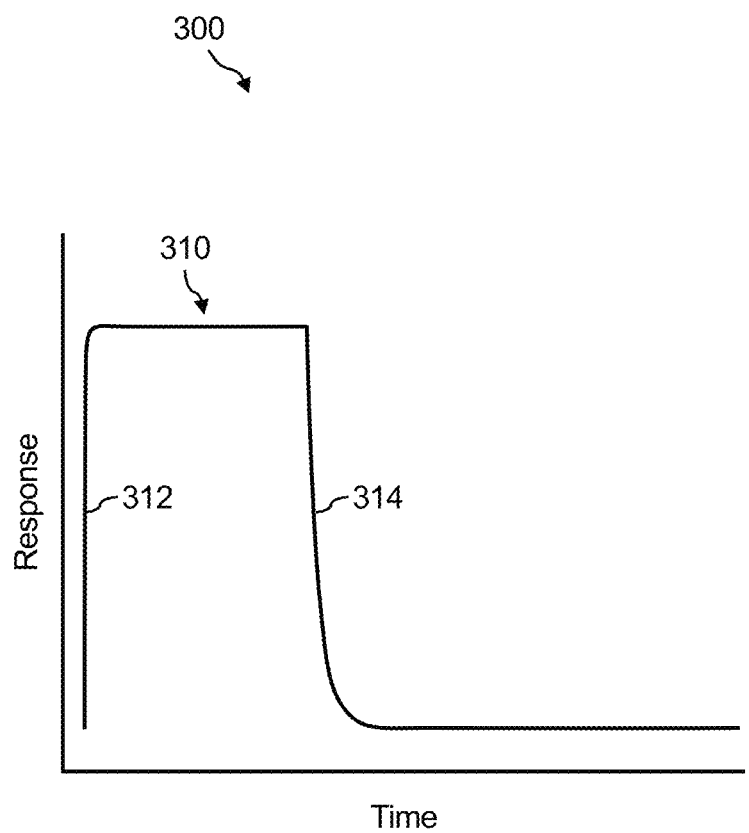
FIG. 10 is a plot of an example of the binding kinetics of an LSPR sensor of the presently disclosed DMF-LSPR cartridge for analysis of analytes.

FIG. 10 shows a plot 300 that illustrates the binding kinetics of the LSPR sensors (e.g., LSPR sensor 136) of LSPR portion 114 of DMF-LSPR cartridge 110. $K_D$ is the equilibrium dissociation constant between an antibody and its antigen. The $K_D$ value is a quantitative measurement of analyte affinity. $K_D$ can be expressed as $K_D = K_{OFF} \div K_{ON}$, where the $K_{OFF}$ value indicates the kinetic OFF-rate of the analyte sample and the $K_{ON}$ value indicates the kinetic ON-rate of the analyte sample.

Plot 300 shows a response curve 310 that indicates, for example, the response time of the analyte sample binding to LSPR sensor 136 as measured using illumination source 154 and optical measurement device 156. A rising portion 312 of curve 310 indicates the $K_{ON}$ of the analyte sample while a falling portion 314 of curve 310 indicates the $K_{OFF}$ of the analyte sample. In PR system 100, LSPR sensor 136 of DMF-LSPR cartridge 110 may be used to measure the $K_{ON}$ value and/or $K_{OFF}$ value of a certain analyte sample. The PR system 100 (e.g., the controller 150) may also calculate the $K_D$ value wherein the $K_D$ value indicates the amount of interaction (or saturation) of the analytes to the surface. For example, a low $K_D$ value means a strong affinity and a high $K_D$ value means a weak affinity.

Figure 11:
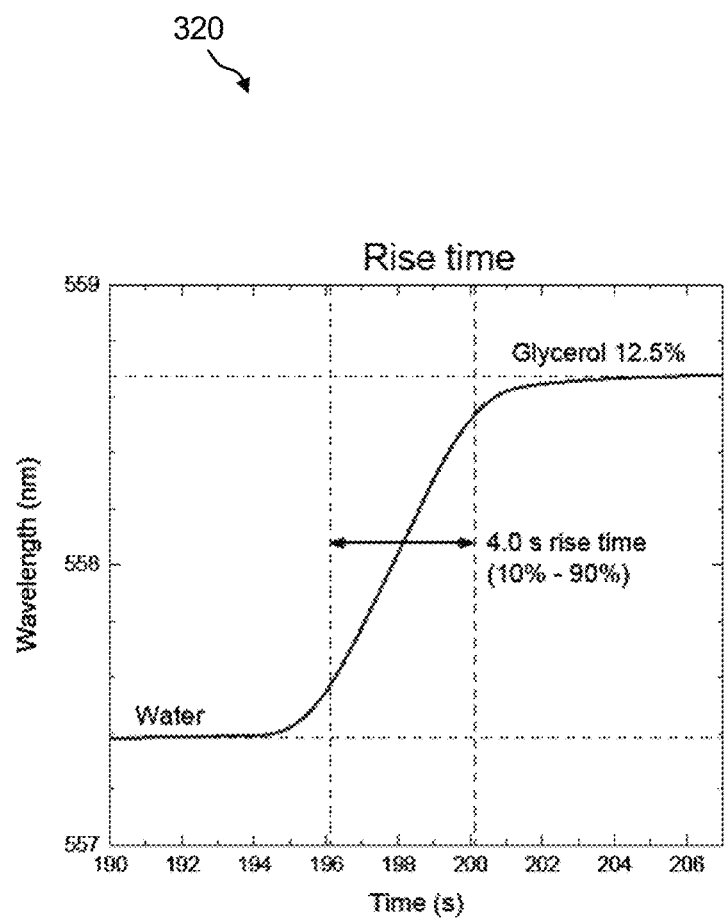
FIG. 11 and FIG. 12 show plots of an example of the $K_{ON}$ and $K_{OFF}$, respectively, of glycerol.
Figure 12:
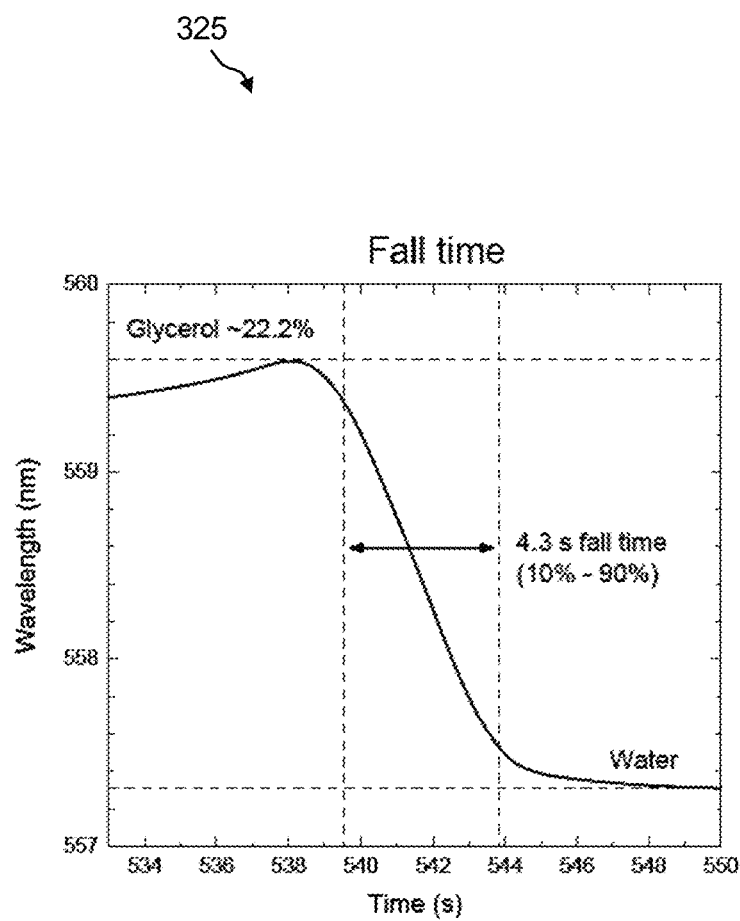

Further to the example, FIG. 11 and FIG. 12 show plots of an example of the $K_{ON}$ and $K_{OFF}$, respectively, of glycerol. FIG. 11 shows a plot 320 of an example of the rise time (i.e., the $K_{ON}$) with respect to detecting water and then glycerol. In this example, a rapid rise time is indicated; in this case, a rise time of about 4 seconds. FIG. 12 shows a plot 325 of an example of the fall time (i.e., the $K_{OFF}$) with respect to detecting glycerol and then back to water. In this example, a rapid fall time is indicated; in this case, a fall time of about 4.3 seconds. In PR system 100, these rapid rise and fall times are essential to measuring the true binding rate to minimize the effects of dispersion between the analyte sample and buffer.

Figure 13:
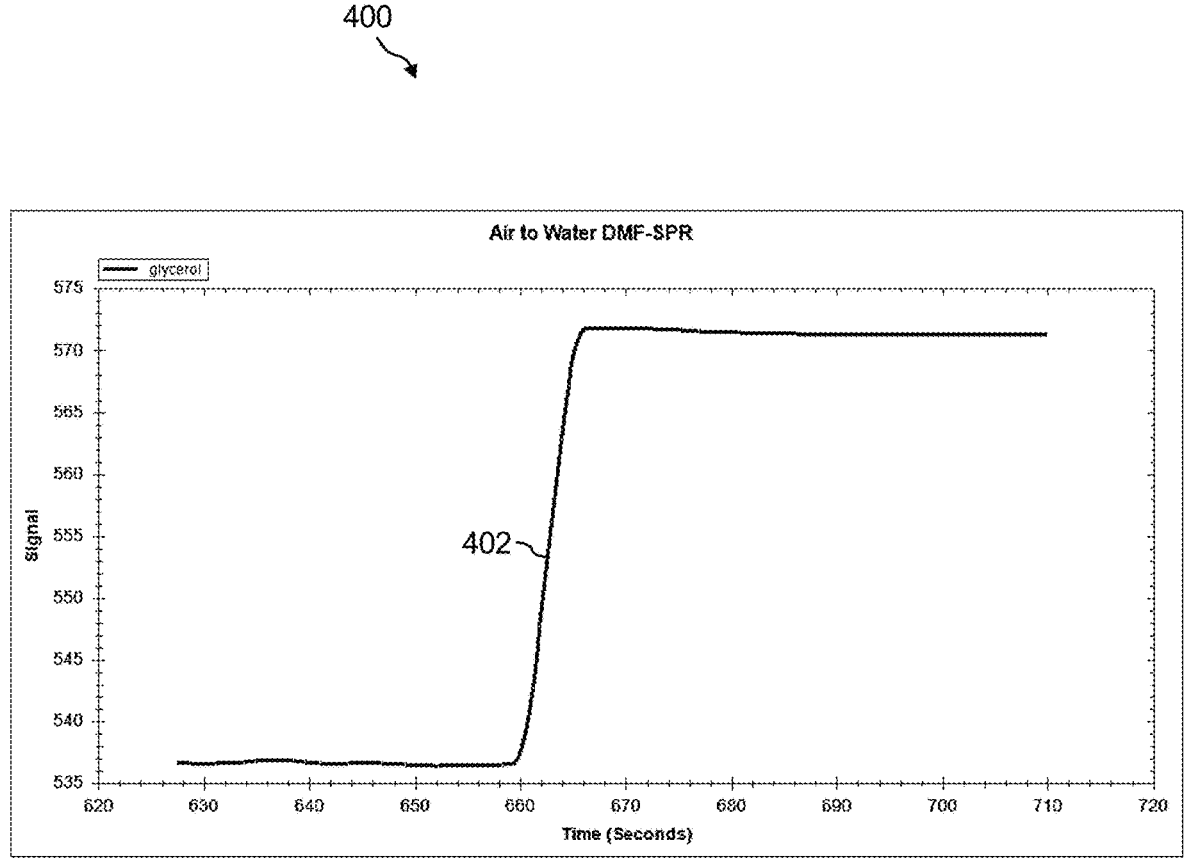
FIG. 13, FIG. 14, and FIG. 15 illustrate plots of examples of signals detected using the LSPR sensor of the DMF-LSPR cartridge of the presently described PR system.
Figure 14:
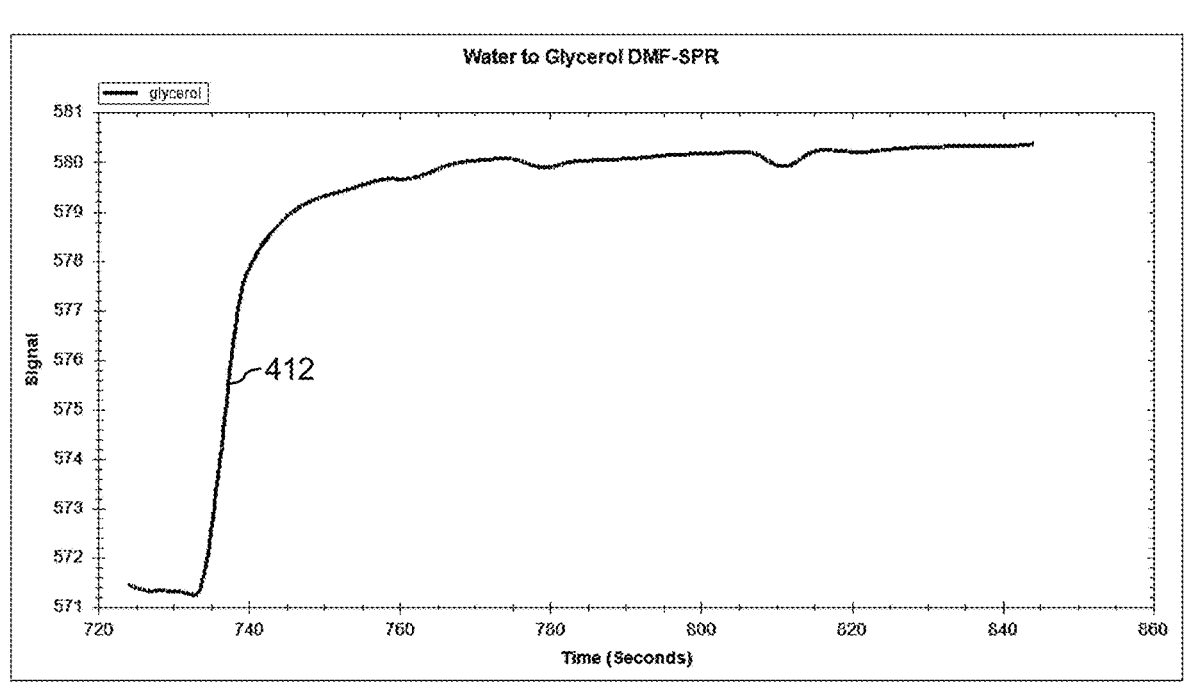
Figure 15:
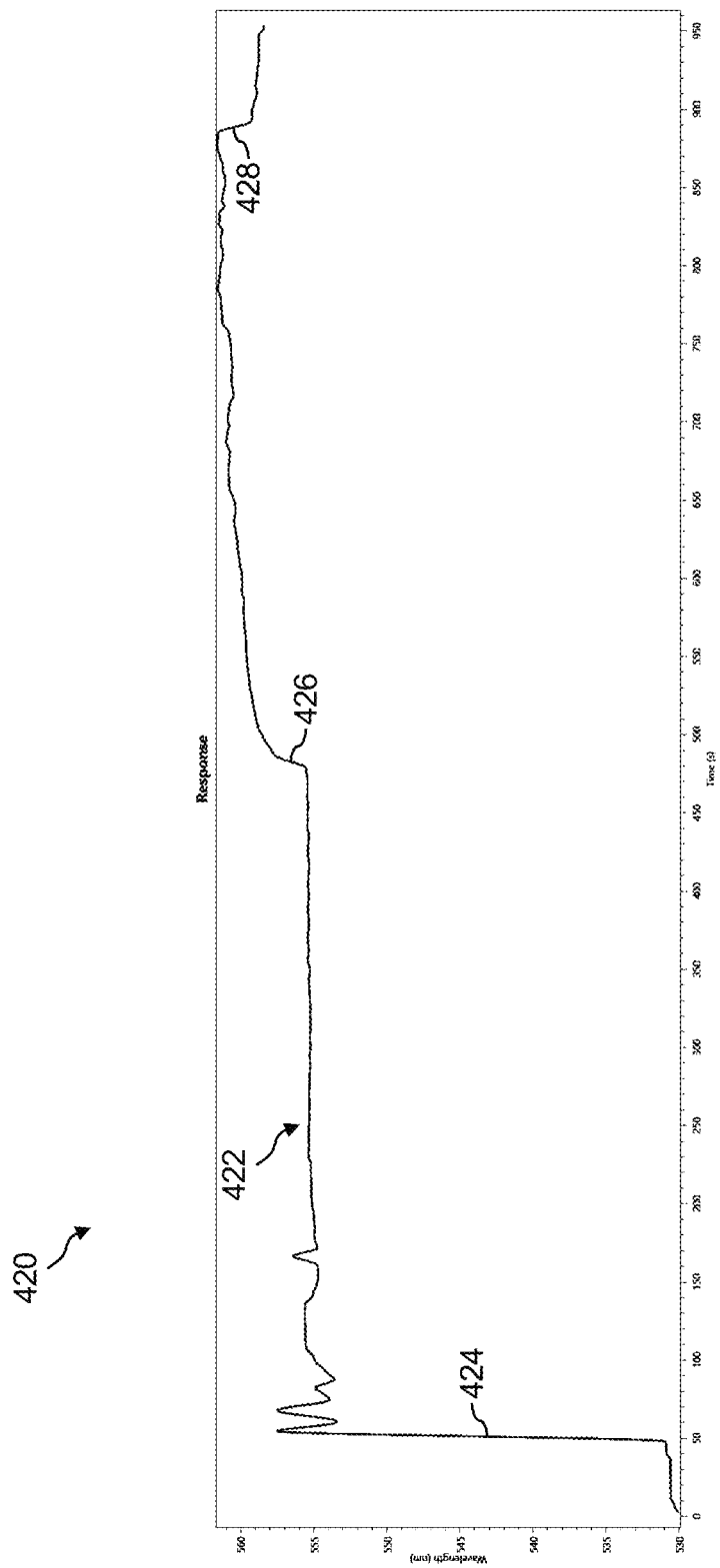

FIG. 13, FIG. 14, and FIG. 15 show plots of examples of signals detected in experiments using LSPR sensor 136 of DMF-LSPR cartridge 110 of the presently disclosed PR system 100 shown in FIG. 1. For example, FIG. 13 shows a plot 400. A curve 402 of plot 400 indicates the optical signal switching from air to a droplet of water as detected at LSPR sensor 136. FIG. 14 shows a plot 410. A curve 412 of plot 410 indicates the optical signal switching from water to a droplet of 25% glycerol as detected at LSPR sensor 136. FIG. 15 shows a plot 420. A curve 422 of plot 420 indicates the optical signal switching from air to water (i.e., at a transition 424), then switching from water to 25% glycerol (i.e., at a transition 426), then switching from 25% glycerol back to water (i.e., at a transition 428), as detected at LSPR sensor 136.

Figure 16:
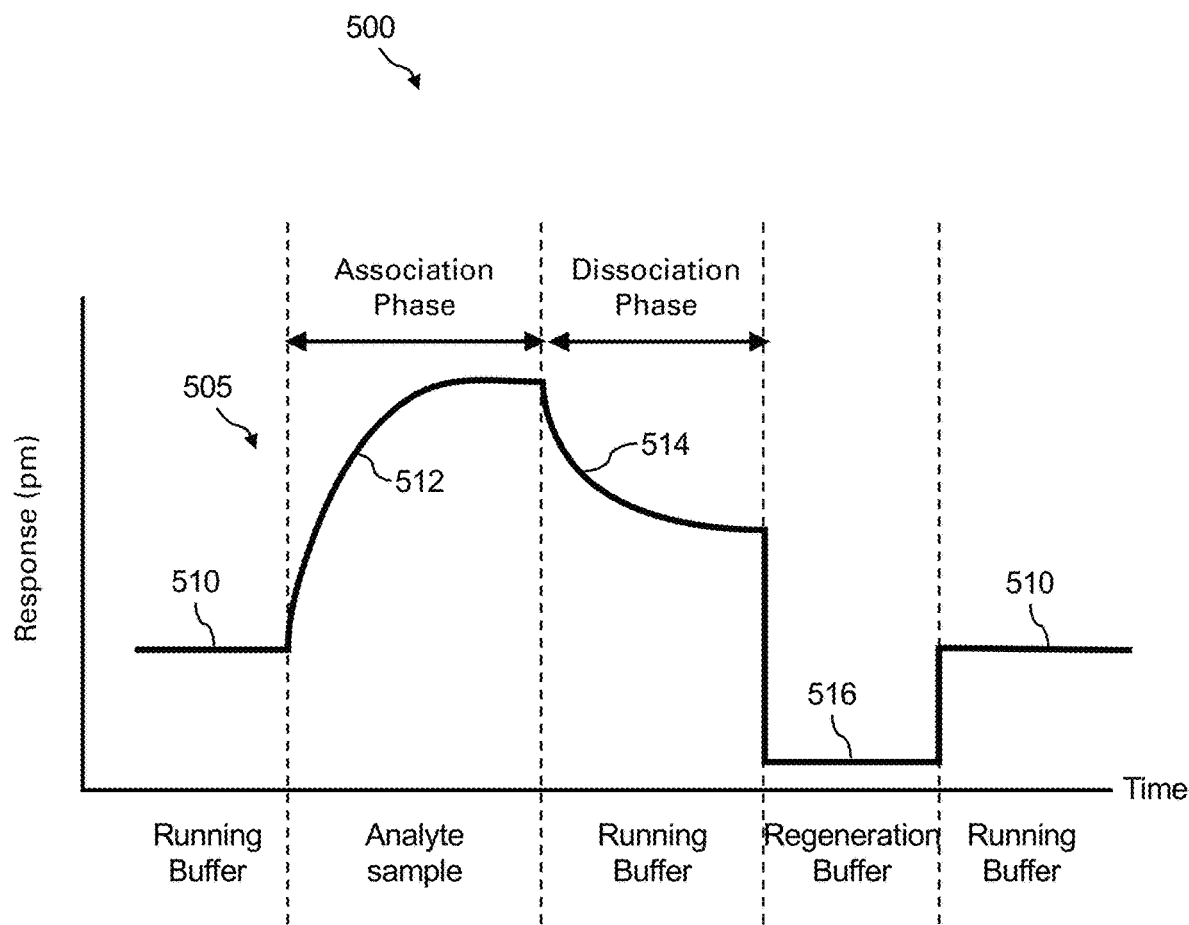
FIG. 16 is a plot (or sensorgram) of an example of a detection cycle of a DMF-LSPR cartridge of the presently described PR system.

FIG. 16 shows a plot 500 (or sensorgram) of an example of a detection cycle of DMF-LSPR cartridge 110 of a PR system 100. A response curve 505 of plot 500 depicts an example of the real-time optical signal from LSPR sensor 136, in this case, a real-time optical signal that correlates to various fluids flowing over LSPR sensor 136.

A curve region 510 of response curve 505 correlates to a first portion of the detection cycle in which a running buffer solution is flowing over LSPR sensor 136. Curve region 510 is the baseline LSPR signal.

A curve region 512 of response curve 505 correlates to a next portion of the detection cycle in which the running buffer is replaced with some concentration of the analyte of interest flowing over LSPR sensor 136. In this portion of the cycle, the solution may be some amount of analyte diluted in the running buffer. For example, a 10 nanomolar solution of the protein sample and buffer. Here, there is an increase in the response, referred to as the association phase. The response increase is due to the analyte binding to the binding partner on the surface of LSPR sensor 136. In one example, the association phase may occur over 1-2 minutes in real time. Note that curve region 512 may plateau as equilibrium is approached and/or reached for a given concentration at LSPR sensor 136. Curve portion 512 indicates the equilibrium for the ON-rate of the analyte.

A curve region 514 of response curve 505 correlates to a next portion of the detection cycle in which the analyte of interest is replaced with running buffer solution again flowing over LSPR sensor 136. At curve region 514 the concentration of the analyte sample falls to zero and thus there is a decrease in the response, which is referred to as the dissociation phase. In the dissociation phase, the response falls back toward the baseline LSPR signal. In one example, the dissociation phase may occur over 1-2 minutes in real time. curve region 514 indicates the equilibrium for the OFF-rate of the analyte.

A curve region 516 of response curve 505 correlates to a next portion of the detection cycle in which the running buffer solution is replaced with a regeneration buffer solution flowing over LSPR sensor 136. It will be appreciated that the composition of the running buffer solution varies with the SPR application. Buffers may, for example, be selected to improve the system performance by reducing non-specific binding, improving functionalization density and/or improving analyte stability. Examples of suitable buffers include Tris buffers, phosphate buffered saline and HEPES buffered saline. The regeneration buffer solution may be, for example, a low pH buffer solution that forces the complex to dissociate. The regeneration buffer increases the potential that there is substantially no analyte on the surface of LSPR sensor 136 before beginning the next detection cycle; i.e., assists in forcing the LSPR sensor 136 back to the baseline LSPR signal.

The sensor data of the association phase (i.e., curve region 512) and the sensor data of the dissociation phase (i.e., curve region 514) may include two pieces of information that is processed in PR system 100. For example, the sensor data of the association phase (i.e., curve region 512) may be fit to a curve and then the ON-rate (i.e., $K_{ON}$ value) of the analyte of interest may be determined from the shape of the curve. Next, the sensor data of the dissociation phase (i.e., curve region 514) may be fit to a curve and then the OFF-rate (i.e., $K_{OFF}$ value) of the analyte of interest may be determined from the shape of the curve. In so doing, the ON-rate (i.e., the $K_{ON}$ value), the OFF-rate (i.e., the $K_{OFF}$ value), and the $K_D$ value of the interaction between the analyte and ligand may be determined.

Figure 17:
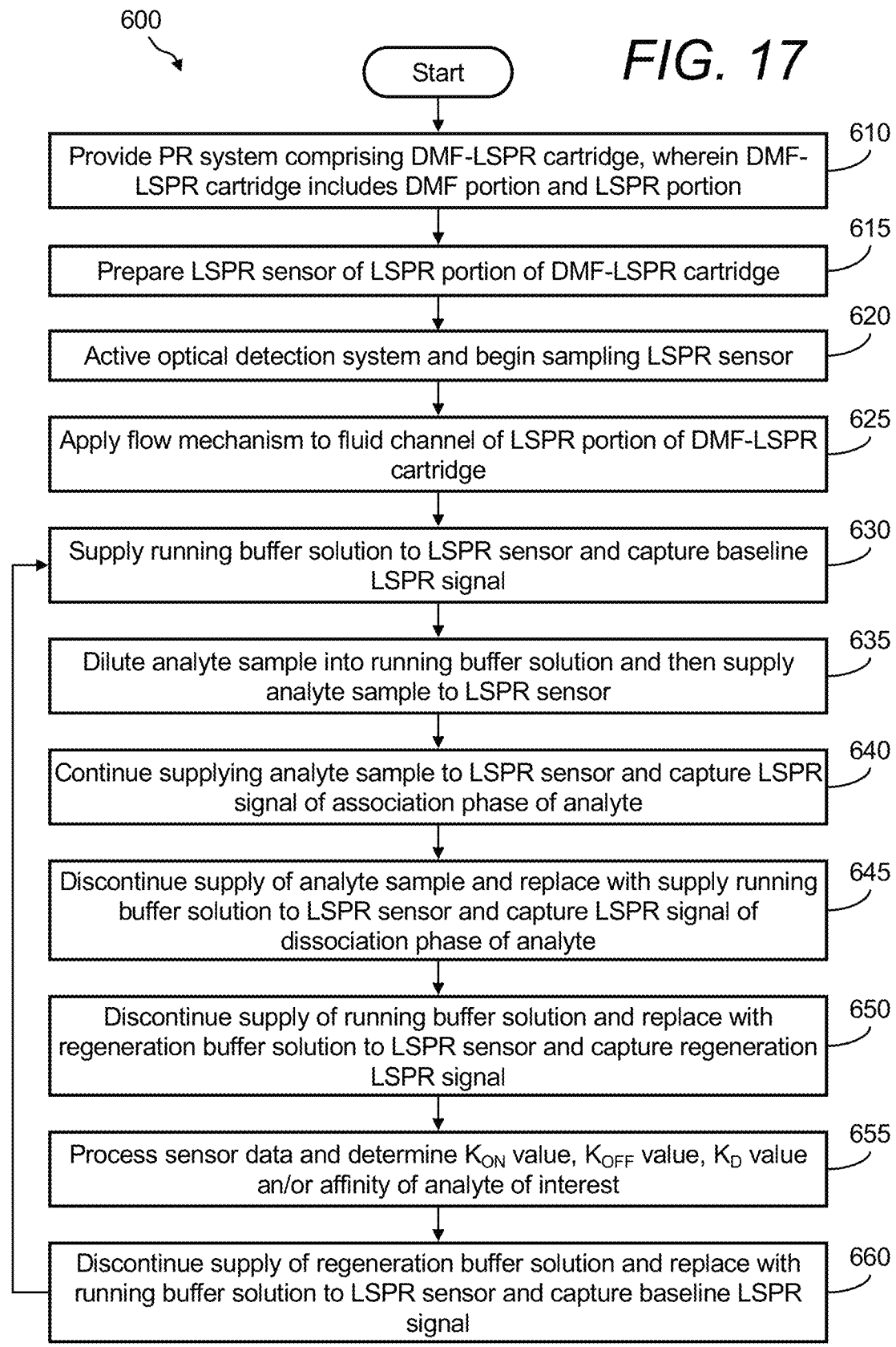
FIG. 17 is a flow diagram of an example of a method of using the presently disclosed PR system that may include a DMF-LSPR cartridge for analysis of analytes.

FIG. 17 is a flow diagram of an example of a method 600 of using the presently disclosed PR system 100 that may include DMF-LSPR cartridge 110 for analysis of analytes. In method 600, the LSPR signal from LSPR sensor 136 may be captured in real time and then the information may be processed. Method 600 may include, but is not limited to, the following steps.

At a step 610, PR system 100 may be provided that may include DMF-LSPR cartridge 110 wherein DMF-LSPR cartridge 110 may include DMF portion 112 and LSPR portion 114.

At a step 615, LSPR sensor 136 of LSPR portion 114 of DMF-LSPR cartridge 110 may be prepared. For example, one reservoir of DMF portion 112 of DMF-LSPR cartridge 110 may be loaded with a solution of ligands (e.g., capture molecules 214 shown in FIG. 5 and FIG. 6). The solution of ligands may be diluted with the running buffer. Depending on the type of surface chemistry on LSPR sensor 136, there may be an activation step or conditioning step to get the surface of LSPR sensor 136 ready for the ligand. Once the surface is ready, ligand droplets 146 may be transported over the surface of LSPR sensor 136 until the desired density is reached. The surface of LSPR sensor 136 may be washed with running buffer to remove any non-specifically bound ligand. LSPR sensor 136 may now ready for the first analyte step.

At a step 620, the optical detection system may be activated and sampling of the LSPR signal may begin. For example, activate illumination source 154 and optical measurement device 156 may be activated. Optical measurement device 156 may begin sampling the LSPR signal from LSPR sensor 136.

At a step 625, flow mechanism (e.g., vacuum force) may be applied to fluid channel 130 of LSPR portion 114 of DMF-LSPR cartridge 110. For example, flow mechanism 158 may be activated to provide vacuum force to fluid channel 130.

At a step 630, running buffer solution may be supplied to LSPR sensor 136 and the baseline LSPR signal may be captured. For example, using droplet operations in DMF portion 112, droplets 146 of running buffer solution may be supplied to fluid channel 130 and with vacuum force at fluid channel 130, a substantially continuous stream of running buffer solution flows across LSPR sensor 136 of LSPR portion 114. Then, using optical measurement device 156, the baseline LSPR signal from LSPR sensor 136 may be captured. Referring now again to FIG. 16, curve region 510 of response curve 505 of plot 500 may be an example of the baseline LSPR signal that may be captured using optical measurement device 156.

At a step 635, the analyte sample may be diluted into the running buffer solution and then the analyte sample may be supplied to LSPR sensor 136. For example, using droplet operations in DMF portion 112, the analyte sample may be diluted into the running buffer solution. Then, droplets 146 of analyte sample may be supplied to fluid channel 130 and with vacuum force at fluid channel 130, a substantially continuous stream of analyte sample flows across LSPR sensor 136 of LSPR portion 114.

At a step 640, the analyte sample continues flowing across LSPR sensor 136 and then the LSPR signal of the association phase of the analyte may be captured. For example, using droplet operations in DMF portion 112 and with vacuum force at fluid channel 130, a substantially continuous stream of analyte sample flows across LSPR sensor 136 of LSPR portion 114. Then, using optical measurement device 156, the LSPR signal from LSPR sensor 136 may be captured, which may correspond to the LSPR signal of the association phase of the analyte. Referring now again to FIG. 16, curve region 512 of response curve 505 of plot 500 provides an example of the association phase LSPR signal that may be captured using optical measurement device 156.

At a step 645, the supply of analyte sample may be discontinued to LSPR sensor 136 and replaced with a supply the running buffer solution and then the LSPR signal of the dissociation phase of the analyte is captured. For example, using droplet operations in DMF portion 112 and with vacuum force at fluid channel 130, the supply of analyte sample may be discontinued and replaced with running buffer solution. Then, a substantially continuous stream of running buffer solution may flow across LSPR sensor 136 of LSPR portion 114. Then, using optical measurement device 156, the LSPR signal from LSPR sensor 136 may be captured, which may correspond to the LSPR signal of the dissociation phase of the analyte. Referring now again to FIG. 16, curve region 514 of response curve 505 of plot 500 provides an example of the dissociation phase LSPR signal that may be captured using optical measurement device 156.

At a step 650, the supply of running buffer solution may be discontinued to LSPR sensor 136 and replaced with a supply the regeneration buffer solution and then the regeneration LSPR signal may be captured. For example, using droplet operations in DMF portion 112 and with vacuum force at fluid channel 130, the supply of running buffer solution may be discontinued and replaced with regeneration buffer solution. Then, a substantially continuous stream of regeneration buffer solution may flow across LSPR sensor 136 of LSPR portion 114. Then, using optical measurement device 156, the regeneration LSPR signal from LSPR sensor 136 may be captured. Referring now again to FIG. 16, curve region 516 of response curve 505 of plot 500 provides an example of the regeneration LSPR signal that may be captured using optical measurement device 156.

At a step 655, the sensor data may be processed and the $K_{ON}$ value, $K_{OFF}$ value, $K_D$ value, and/or affinity of the analyte of interest may be determined. For example, using controller 150 of PR system 100, the sensor data of the association phase (e.g., curve region 512 of response curve 505 of plot 500) may be fit to a curve and then the ON-rate (i.e., $K_{ON}$ value) of the analyte of interest can be determined from the shape of the curve. Next, the sensor data of the dissociation phase (e.g., curve region 514 of response curve 505 of plot 500) may be fit to a curve and then the OFF-rate (i.e., $K_{OFF}$ value) of the analyte of interest can be determined from the shape of the curve. Any binding model can be used, such as 1:1 binding, 1:2 binding, bivalent binding, and so on. Typically, data may be fit with global fit models across all concentrations of the analyte.

At a step 660, the supply of regeneration buffer solution may be discontinued to LSPR sensor 136 and replaced with a supply the running buffer solution and then the baseline LSPR signal may be captured. For example, using droplet operations in DMF portion 112 and with vacuum force at fluid channel 130, the supply of regeneration buffer solution may be discontinued and replaced with running buffer solution. Then, using optical measurement device 156, the baseline LSPR signal from LSPR sensor 136 may be captured. Referring now again to FIG. 16, curve region 510 of response curve 505 of plot 500 provides an example of the baseline LSPR signal that may be captured using optical measurement device 156.

At the completion of method step 660, method 600 may return to step 630 wherein method steps 630 through 660 may repeat until the sample preparation process is completed. Method steps 630 through 660 may be repeated using multiple concentrations of the analyte of interest. For example, typically 5 concentrations from about 0.1× to about 10× the $K_D$ value and with about 3-fold differences between each concentration.

Figure 18:
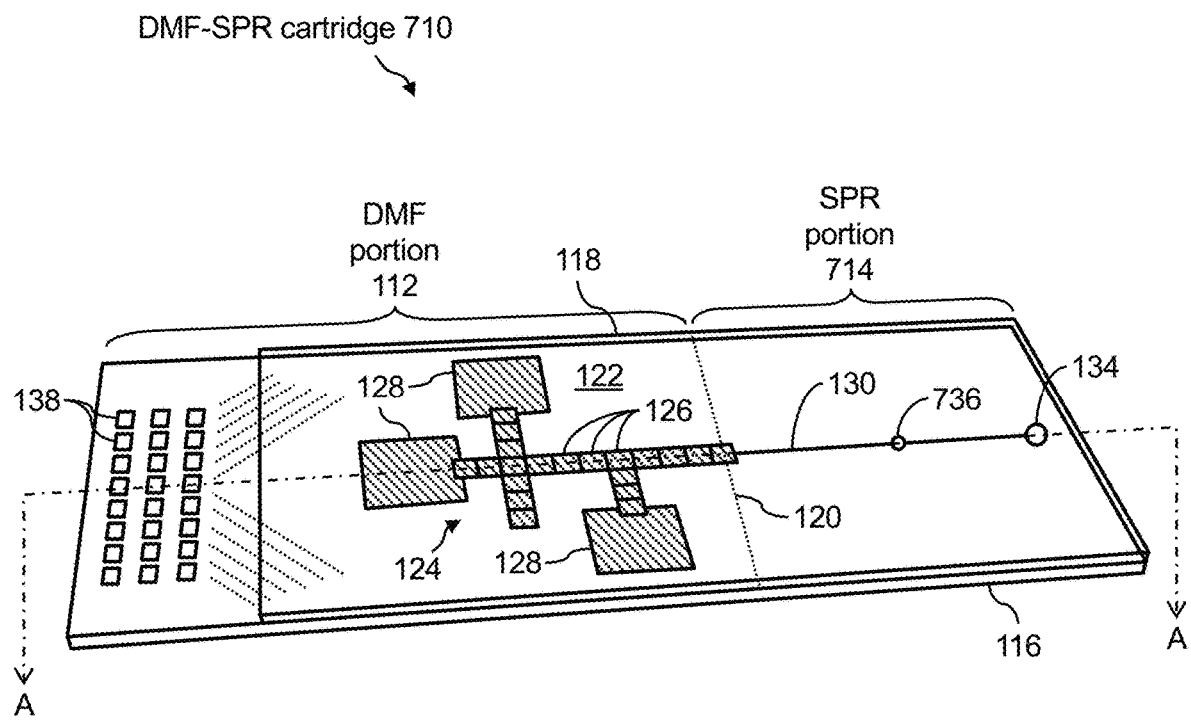
FIG. 18 and FIG. 19 is a perspective view and a side view, respectively, of an example of a DMF-SPR cartridge.
Figure 19:
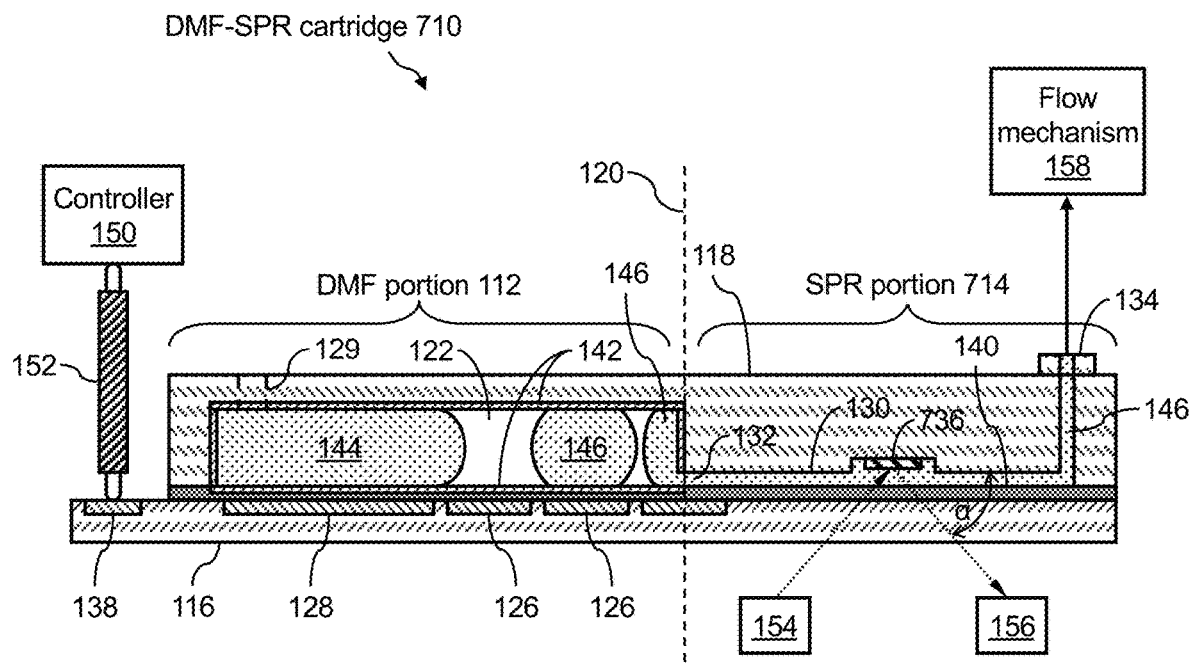

Further, the presently disclosed PR system 100 is not limited to a cartridge (e.g., DMF-LSPR cartridge 110) that supports both DMF capability and LSPR capability only. In other examples, PR system 100 may include a cartridge that supports both DMF capability and SPR capability, along with an optical detection system that operates in reflection mode rather than transmission mode. For example, FIG. 18 and FIG. 19 is a perspective view and a side view, respectively, of an example of a DMF-SPR cartridge 710.

DMF-SPR cartridge 710 may be substantially the same as DMF-LSPR cartridge 110 as described with reference to FIG. 1 through FIG. 17 except that it may include an SPR sensor and a corresponding optical detection system operating in reflection mode instead of an LSPR sensor and a corresponding optical detection system operating in transmission mode. For example, DMF-SPR cartridge 710 may include DMF portion 112 as described in relation to FIG. 1 through FIG. 17 above in combination with an SPR portion 714. SPR portion 714 may be substantially the same as LSPR portion 114 of DMF-LSPR cartridge 110 except that LSPR sensor 136 may be replaced with an SPR sensor 736.

SPR sensor 736 may be interrogated optically in reflection mode. For example, illumination source 154 and optical measurement device 156 may be arranged on one side of SPR sensor 736 wherein the reflectance angle α can be measured. In operation, the reflectance angle α may be measured prior to binding. Then binding occurs which causes the reflectance angle α to change. The amount of change indicates the antibody affinity. Other sensors can also be used in place of the SPR or LSPR sensor. For example, optical sensors may be used, such as biolayer interferometry, piezoelectric sensors, and electrical sensors.

In summary and referring now again to FIG. 1 through FIG. 19, the presently disclosed PR system 100, which may include DMF-LSPR cartridge 110 that supports both DMF capability and LSPR capability, and method 600 may be used to measure the optical spectrum of LSPR sensor 136 prior to any analyte binding events occurring thereon and then measure the optical spectrum of LSPR sensor 136 after analyte binding events have occurred thereon.

Further, in the presently disclosed PR system 100, DMF portion 112 of DMF-LSPR cartridge 110 facilitates DMF capabilities generally for merging, splitting, dispensing, diluting, other fluid handling operations, and the like. One application of these DMF capabilities may be sample preparation. LSPR portion 114 of DMF-LSPR cartridge 110 may include LSPR sensor 136 for (1) detecting, for example, certain molecules (e.g., target analytes) and/or chemicals in the sample, and (2) for analysis of analytes; e.g., for measuring binding events in real time to extract ON-rate information, OFF-rate information, and/or affinity information.

Further, in the presently disclosed PR system 100, which may include DMF-LSPR cartridge 110, and method 600, optical measurements may be taken very close to the surface of LSPR sensor 136 as compared with standard SPR. Accordingly, using DMF-LSPR cartridge 110, the majority of the optical signal is from very close to the surface where the actual binding events occur. By contrast, in standard SPR, measurements are taken far from the surface and are subject to a large bulk effect.

Further, in the presently disclosed PR system 100, which may include DMF-LSPR cartridge 110, and method 600, the diffusion and/or flow rate of the analyte may be faster than the binding rate, thereby assisting the LSPR sensor 136 to measure the binding rate in a manner that is not limited by a slow diffusion or flow rate. The rise and fall time may also be very fast ensuring minimal dispersion, allowing very fast binding rates to be measured.

Further, in the presently disclosed PR system 100, which may include DMF-LSPR cartridge 110, and method 600, the LSPR sensor 136 can be used to determine the $K_D$ value, the $K_{ON}$ value, and/or the $K_{OFF}$ value of the analyte sample with an immobilized ligand wherein the $K_D$ value is a quantitative measurement of analyte affinity, the $K_{ON}$ value indicates the kinetic ON-rate of the analyte sample, and the $K_{OFF}$ value indicates the kinetic OFF-rate of the analyte sample.

Further, as compared with standard SPR technology the presently disclosed PR system 100, which may include DMF-LSPR cartridge 110, and method 600, facilitates (1) reduced instrument cost without sacrificing on performance; (2) reduced cost of the microfluidics needed for a multiple-channel fully automated, high-throughput system; (3) a DMF-LSPR cartridge (e.g., DMF-LSPR cartridge 110) that allows a range of product price points and capabilities with minimal technical changes; (4) reduced instrument maintenance, cleaning, and/or downtime; (5) reduced assay complexity, training, and/or hands-on time; (6) flexibility to automate assay optimization when combined with artificial intelligence/big data collection and analysis, and (7) a DMF-LSPR cartridge that is not limited to running one assay only; namely, a single DMF-LSPR cartridge design may support the ability to run multiple different assays on the fly.

While FIG. 1 through FIG. 19 show and describe a PR system that may include the DMF-LSPR cartridge that may further include DMF portion and LSPR portion and wherein the LSPR portion may include an LSPR sensor for the analysis of analytes, the presently disclosed PR system and cartridge is not limited to this configuration only. For example, FIG. 20 through FIG. 44 show and describe another configuration of PR system in which the LSPR portion of the DMF-LSPR cartridge may include an "in-line reference channel," meaning a fluid channel that may include at least one "reference spot" in line with at least one "sample spot."

Figure 20:
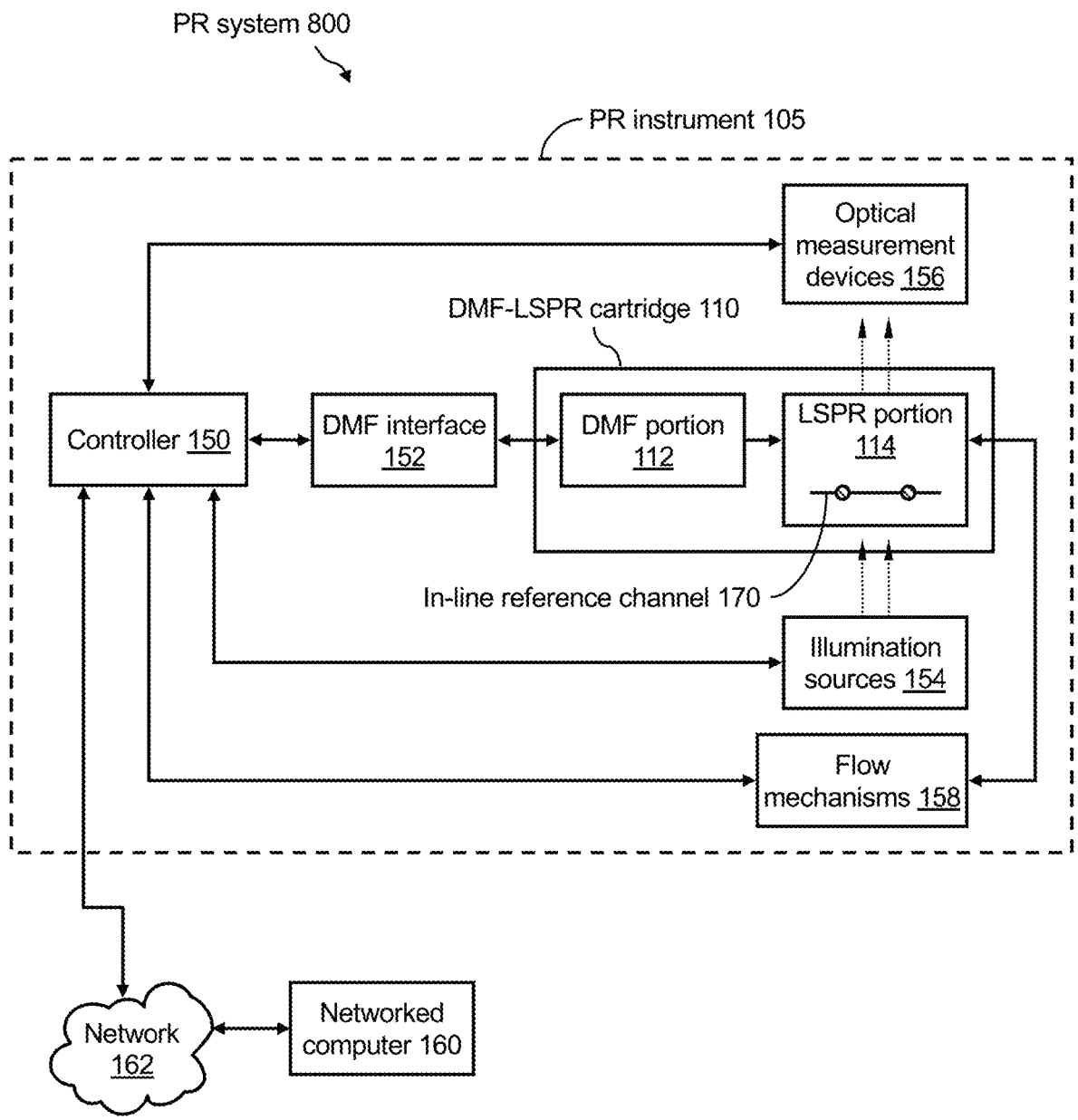
FIG. 20 is a block diagram of another example of the presently disclosed PR system including a DMF-LSPR cartridge that further includes, but is not limited to, an in-line reference channel.

FIG. 20 is a block diagram of an example of the presently disclosed PR system 800 that may include a cartridge that supports both DMF and LSPR for analysis of analytes. PR system 800 is substantially the same as PR system 100 that is described hereinabove with reference to FIG. 1 through FIG. 19 except that in PR system 800 the LSPR portion 114 of DMF-LSPR cartridge 110 may further include an in-line reference channel 170. Additionally, PR system 800 may include multiple illumination sources 154, multiple optical measurement devices 156, and/or multiple flow mechanisms 158.

Namely, like PR system 100, PR system 800 may be an LSPR system, wherein PR system 800 may include DMF-LSPR cartridge 110 that supports both DMF capability and LSPR capability for analysis of analytes. In PR system 800 for analysis of analytes, analysis may include, for example, detection, identification, quantification, or measuring analytes and/or measuring the interactions of analytes with other substances, such as measuring binding kinetics. Exemplary analytes may include, but are not limited to, small molecules, proteins, peptides, antibodies, lipids, cells, nucleic acids, atoms, ions, and the like. For example, PR system 800 may be used to measure the binding kinetics of a ligand to a macromolecule, such as a receptor.

Again, DMF portion 112 of DMF-LSPR cartridge 110 may facilitate DMF capabilities generally for merging, splitting, dispensing, diluting, other fluid handling operations, and the like. LSPR portion 114 may include the detection portion of DMF-LSPR cartridge 110 that may include in-line reference channel 170. DMF portion 112 may be fluidly coupled to in-line reference channel 170 of LSPR portion 114. In-line reference channel 170 may be a fluid channel that may include at least one reference spot 174 (see FIG. 21) in line with at least one sample spot 172 (see FIG. 21).

Each sample spot 172 in in-line reference channel 170 may include an LSPR sensor 136 (see FIG. 21) that is functionalized for (1) detecting, for example, certain molecules (e.g., target analytes) and/or chemicals in the sample, and (2) analysis of analytes; e.g., for measuring binding events in real time to extract ON-rate information, OFF-rate information, and/or affinity information. In one example, each reference spot 174 in in-line reference channel 170 may include an LSPR sensor 136 (see FIG. 21) that is not functionalized. In another example, each reference spot 174 in in-line reference channel 170 may include an LSPR sensor 136 that is functionalized with a non-target molecule or a "dummy" molecule. More details of various examples of DMF-LSPR cartridge 110 are shown and described hereinbelow with reference to FIG. 21 through FIG. 32.

In PR system 800, multiple outlets 134 (see FIG. 21) may be provided along in-line reference channel 170 of LSPR portion 114 of DMF-LSPR cartridge 110. Each of the outlets 134 may be fluidly coupled to a respective flow mechanism 158 for directing and/or assisting the flow to/from a certain sample spot 172 or a certain reference spot 174. Each of the flow mechanisms 158 may be any mechanism for producing and/or assisting flow through in-line reference channel 170 of LSPR portion 114. Each of the flow mechanisms 158 may be, for example, a positive or negative pressure source (e.g., a syringe pump), a microfluidic pump, an electro-osmotic pump, a passive pumping mechanism (e.g., capillary action, gravity flow), and the like.

Figure 21:
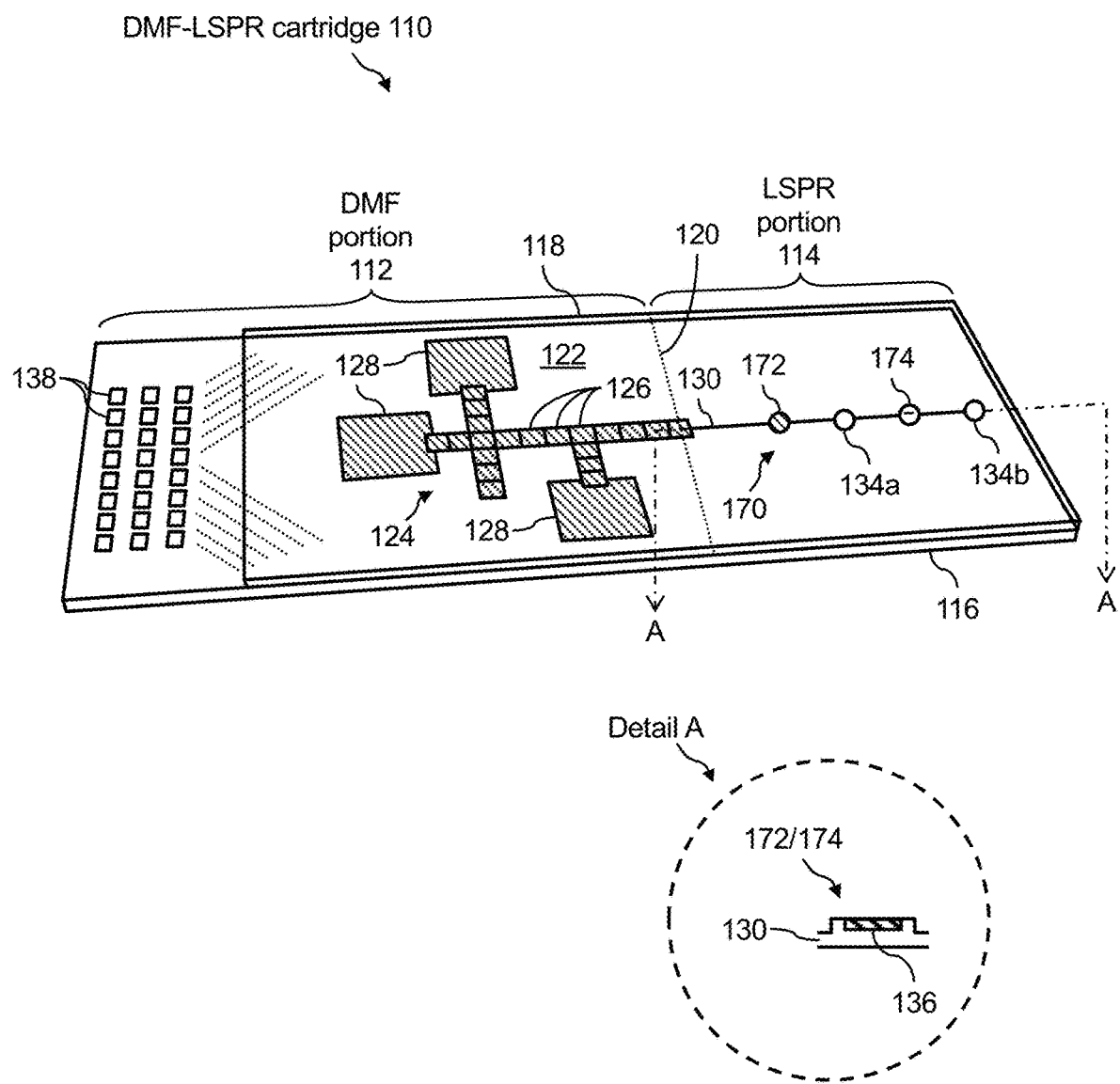
FIG. 21 is a perspective view of a DMF-LSPR cartridge that may include the in-line reference channel, which is one example of a DMF-LSPR cartridge of the presently disclosed PR system.

FIG. 21 is a perspective view of an example of a DMF-LSPR cartridge 110 that may include in-line reference channel 170. In this example, DMF-LSPR cartridge 110 may be a single-channel device, meaning that it may include one in-line reference channel 170 only. However, this is exemplary only. Accordingly, DMF-LSPR cartridge 110 may include multiple in-line reference channels 170 and can therefore be a multiple-channel device.

In DMF-LSPR cartridge 110, boundary droplet operations electrode 126 of DMF portion 112 may supply in-line reference channel 170 of LSPR portion 114. In-line reference channel 170 may include fluid channel 130, wherein inlet 132 (see FIG. 22) of fluid channel 130 is at boundary droplet operations electrode 126. From inlet 132, fluid channel 130 extends along LSPR portion 114.

Generally, the dimensions of fluid channel 130 may be microchannel sized in order to keep volume consumption low. Additionally, the width of fluid channel 130 should be less than the width of boundary droplet operations electrode 126. In one example, fluid channel 130 may be from about 50 μm to about 1000 μm wide (side-to-side) and from about 25 μm to about 200 μm high (or deep, top to bottom). In another example, fluid channel 130 may be about 100 μm wide and about 50 μm high (or deep). Additionally, in other examples, it may be beneficial to taper the height h (see FIG. 22) of reaction (or assay) chamber 122 to a preferred height (or depth) of fluid channel 130.

At least one functionalized LSPR sensor 136 (see Detail A of FIG. 21) may be provided along fluid channel 130 to provide at least one sample spot 172. At least one non-functionalized LSPR sensor 136 (see Detail A of FIG. 21) may be provided along fluid channel 130 to provide at least one reference spot 174. Further, one or more outlets 134 (see FIG. 22, FIG. 25, FIG. 28) may be provided along fluid channel 130 in relation to the one or more sample spots 172 and/or the one or more reference spots 174. Together, fluid channel 130, the at least one functionalized LSPR sensor 136 (i.e., sample spot 172), the at least one non-functionalized LSPR sensor 136 (i.e., reference spot 174), and the one or more outlets 134 may include in-line reference channel 170.

Figure 22:
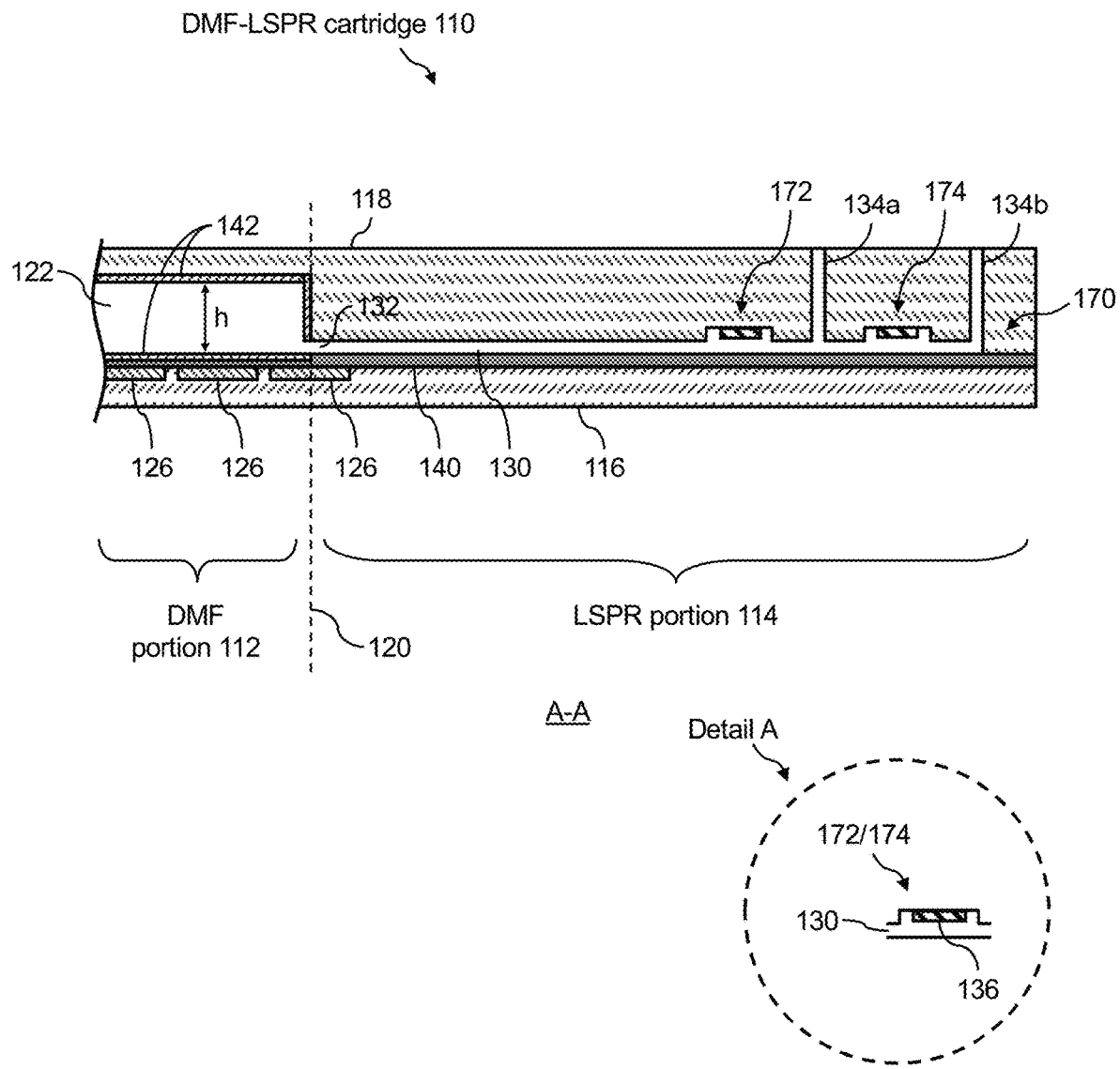
FIG. 22 is a cross-sectional view of an example of a DMF-LSPR cartridge showing an example of the in-line reference channel.

FIG. 22 is a cross-sectional view of an example of the presently disclosed DMF-LSPR cartridge 110 and showing an example of in-line reference channel 170. For example, FIG. 22 is a partial cross-sectional view of DMF-LSPR cartridge 110 taken along line A-A of FIG. 21. As described with reference to PR system 100 of FIG. 1 through FIG. 19, DMF-LSPR cartridge 110 may include dielectric layer 140 atop bottom substrate 116 and electrode arrangement 124. Further, the surfaces of reaction (or assay) chamber 122 may be coated with hydrophobic layer 142. Again, reaction (or assay) chamber 122 has a height h, which can vary in various examples. In one example, the height h may be about 300 µm.

In operation, a quantity of fluid (e.g., liquid reagents, buffer solution, sample fluid) may be provided atop a certain reservoir electrode 128. Then, droplets (not shown) may be dispensed via droplet operations from the reservoir electrode 128 to a line of droplet operations electrodes 126. The fluid and/or droplets may contain, for example, target analytes for binding to LSPR sensors 136 of sample spots 172. Accordingly, illumination sources 154 and optical measurement devices 156 may provide a simple optical detection system for determining the degree of binding at LSPR sensors 136.

In reaction (or assay) chamber 122, the space surrounding the fluid (not shown) and/or droplets (not shown) may be filled with, for example, air or filler fluid (e.g., a low-viscosity oil, such as silicone oil or hexadecane filler fluid). Further, the droplets may, for example, be aqueous or non-aqueous, or may be mixtures or emulsions including aqueous and non-aqueous components, or may be oil-covered droplets (i.e., droplet oil-shell configuration). The droplets may be transported via droplet operations along the droplet operations electrodes 126. For example, the droplets may be transported at a rate that generally allows continuous replenishing of the solution at the inlet of in-line reference channel 170 and thus preventing air to enter the channel. With the vacuum-assist of flow mechanisms 158, fluid may be pulled into in-line reference channel 170 of LSPR portion 114 and across LSPR sensors 136 of sample spots 172 and/or LSPR sensor 136 of reference spot 174. While fluid is at LSPR sensors 136, a detection operation may occur via illumination sources 154 and optical measurement devices 156. For example, optical measurement devices 156 may continuously sample LSPR sensors 136 as fluid flows across LSPR sensors 136.

Referring still to FIG. 22, in-line reference channel 170 may include (in order starting from boundary line interface 120) a sample spot 172 (i.e., a functionalized LSPR sensor 136), then a first outlet 134 (e.g., outlet 134a), then a reference spot 174 (i.e., a non-functionalized LSPR sensor 136), and then a second outlet 134 (e.g., outlet 134b). In one configuration and referring now to FIG. 23A, a schematic diagram shows outlet 134a fluidly coupled to a flow mechanism 158a and outlet 134b fluidly coupled to a flow mechanism 158b. In this way, outlets 134a and 134b may be independently controlled. However, in another configuration and referring now to FIG. 23B, a schematic diagram shows that outlets 134a and 134b may be fluidly coupled to a common flow mechanism 158 and controlled separately by respective valves 176a and 176b.

Figure 23A:
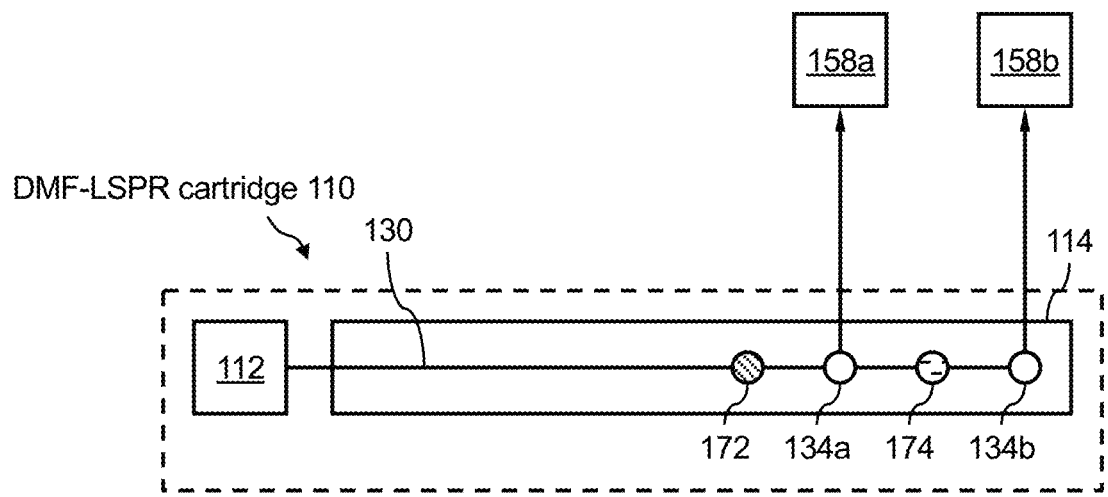
FIG. 23A and FIG. 23B are schematic diagrams of examples of the DMF-LSPR cartridge and in-line reference channel shown in FIG. 22.
Figure 23B:
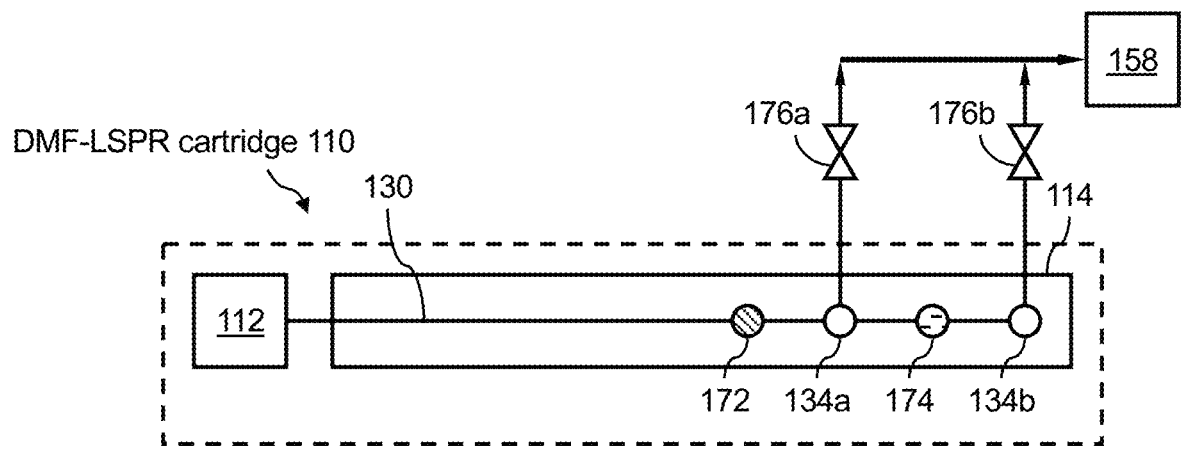
Figure 24:
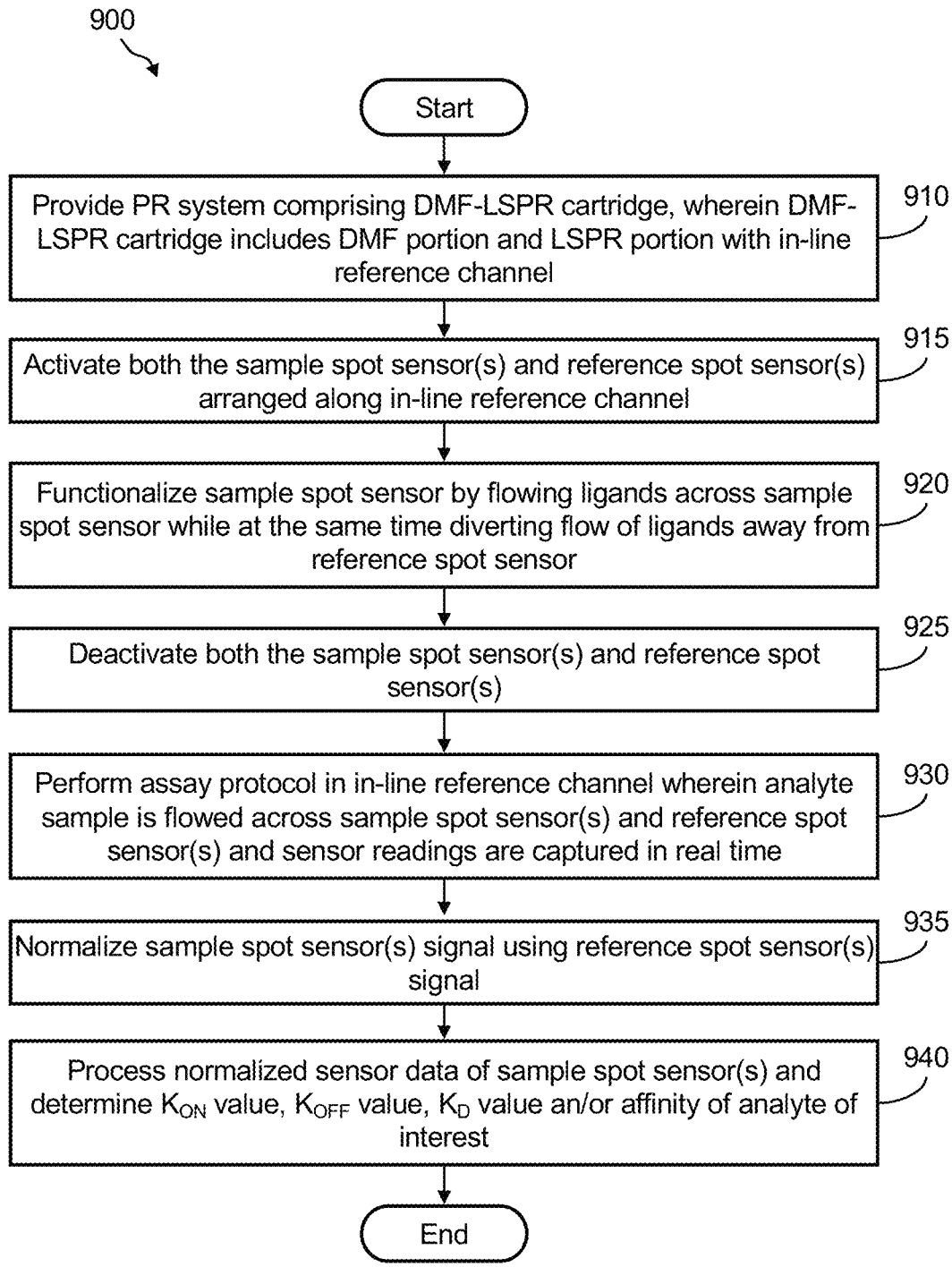
FIG. 24 is a flow diagram of an example of a method of using a DMF-LSPR cartridge and in-line reference channel.

FIG. 24 is a flow diagram of an example of a method 900 of using DMF-LSPR cartridge 110 and in-line reference channel 170 shown in FIG. 22, FIG. 23A, and FIG. 23B, wherein method 900 may include an example of a process of controlling the fluid flow with respect to in-line reference channel 170. Further, by way of example, method 900 describes a process for a carboxyl group (COOH)-based DMF-LSPR cartridge 110. Additionally, while the steps of method 900 correlate to the configuration of DMF-LSPR cartridge 110 and in-line reference channel 170 shown in FIG. 22, FIG. 23A, and FIG. 23B, this is exemplary only. The steps of method 900 may be modified for any configuration of any number and/or arrangements of sample spots 172, reference spots 174, and/or outlets 134 and in any order. Method 900 may include, but is not limited to, the following steps.

At a step 910, PR system 800 may be provided that may include DMF-LSPR cartridge 110, wherein DMF-LSPR cartridge 110 may include DMF portion 112 and LSPR portion 114 that has in-line reference channel 170, such as the in-line reference channel 170 shown in FIG. 22, FIG. 23A, and FIG. 23B.

At a step 915, both the sample spot sensor(s) and reference spot sensor(s) that are arranged along in-line reference channel 170 may be activated. For example, "activation" may include an amine coupling step in which the COOH functional surface coating on the LSPR sensors 136 is converted into an active ester. For example, a solution of EDC/NHS in an activation buffer may be supplied to in-line reference channel 170, flow mechanism 158a connected to outlet 134a is not activated, while flow mechanism 158b connected to outlet 134b is activated. EDC is 1-Ethyl-3-(3-dimethylaminopropyl)-carbodiimide. NHS is N-hydroxysuccinimide. In so doing, the solution may flow along the full length of in-line reference channel 170 and both the LSPR sensor 136 at sample spot 172 and the LSPR sensor 136 at reference spot 174 may be activated. For example, this EDC NHS solution reacts with the COOH sites on the LSPR sensors 136 and turns them into active functional groups that can covalently bind to any amine group on the ligand.

At a step 920, LSPR sensor 136 at sample spot 172 may be functionalized by flowing a solution of ligands (e.g., ligands diluted with the running buffer) across the LSPR sensor 136 at sample spot 172. At the same time, the flow of ligands may be diverted away from the LSPR sensor 136 at reference spot 174. For example, a solution of ligands may be supplied to in-line reference channel 170, flow mechanism 158a connected to outlet 134a is activated, while flow mechanism 158b connected to outlet 134b is not activated. In so doing, the solution may flow along a partial portion only of in-line reference channel 170. For example, the solution flows across the LSPR sensor 136 at sample spot 172 and may be pulled out of outlet 134a before reaching the LSPR sensor 136 at reference spot 174. Accordingly, LSPR sensor 136 at reference spot 174 is not exposed to the ligand solution and remains non-functionalized.

At a step 925, both the sample spot sensor(s) and reference spot sensor(s) that are arranged along in-line reference channel 170 may be deactivated. Deactivation is performed to convert any remaining active binding sites on the LSPR sensors 136 into non-active sites. For example, a "blocking" solution, such as ethanolamine, may be used to react with any remaining COOH site and deactivate them. For example, a solution of ethanolamine may be supplied to in-line reference channel 170, flow mechanism 158a connected to outlet 134a is not activated, while flow mechanism 158b connected to outlet 134b is activated. In so doing, the ethanolamine solution may be flowed along the full length of in-line reference channel 170 and both the LSPR sensor 136 at sample spot 172 and the LSPR sensor 136 at reference spot 174 are deactivated.

At a step 930, the assay protocol may be performed in in-line reference channel 170 wherein the analyte sample may be flowed across the sample spot sensor(s) and the reference spot sensor(s) and sensor readings may be captured in real time. For example, an assay protocol may be performed in which the analyte sample is supplied to in-line reference channel 170. Next, running buffer may be transported over the sensor surfaces for a set period of time (to capture the dissociation phase). Next, if needed, a regeneration buffer may be transported over the sensor surfaces to remove any analyte remaining after the dissociation period. Next, a different concentration of analyte may be injected (usually 3× the previous one) and the above is repeated. This is typically done for at least three analyte concentrations to perform the kinetic analysis.

In step 930, flow mechanism 158a connected to outlet 134a is not activated, while flow mechanism 158b connected to outlet 134b is activated. In so doing, the fluid may be flowed along the full length of in-line reference channel 170 and across both the LSPR sensor 136 at sample spot 172 and the LSPR sensor 136 at reference spot 174. At the same time, using illumination sources 154 and optical measurement device 156, the LSPR signal from LSPR sensor 136 at sample spot 172 and the LSPR signal from LSPR sensor 136 at reference spot 174 may be captured in real time while running the assay protocol.

At a step 935, the sample spot sensor(s) signal may be normalized using the reference spot sensor(s) signal. For example, the signal of LSPR sensor 136 at reference spot 174 may be used to normalize the signal of LSPR sensor 136 at sample spot 172. For example, the signal of LSPR sensor 136 at reference spot 174 may be used to subtract out from the signal of LSPR sensor 136 at sample spot 172 any non-specific binding of the analyte to the sensor, any instrument drift, any bulk refractive index shifts, and so on.

At a step 940, the normalized sensor data from the sample spot sensor(s) may be processed and the $K_{ON}$ value, $K_{OFF}$ value, $K_D$ value, and/or affinity of the analyte of interest may be determined. For example, using controller 150 of PR system 800, the normalized sensor data from LSPR sensor 136 at sample spot 172 may be processed by fitting a binding model to the data and using a regression to find the $K_{ON}$ value, $K_{OFF}$ value, $K_D$ value, and/or affinity of the analyte of interest that best represents the experimental data. This may be accomplished using a data set that may include, for example, the at least three analyte concentrations described in step 930.

Figure 25:
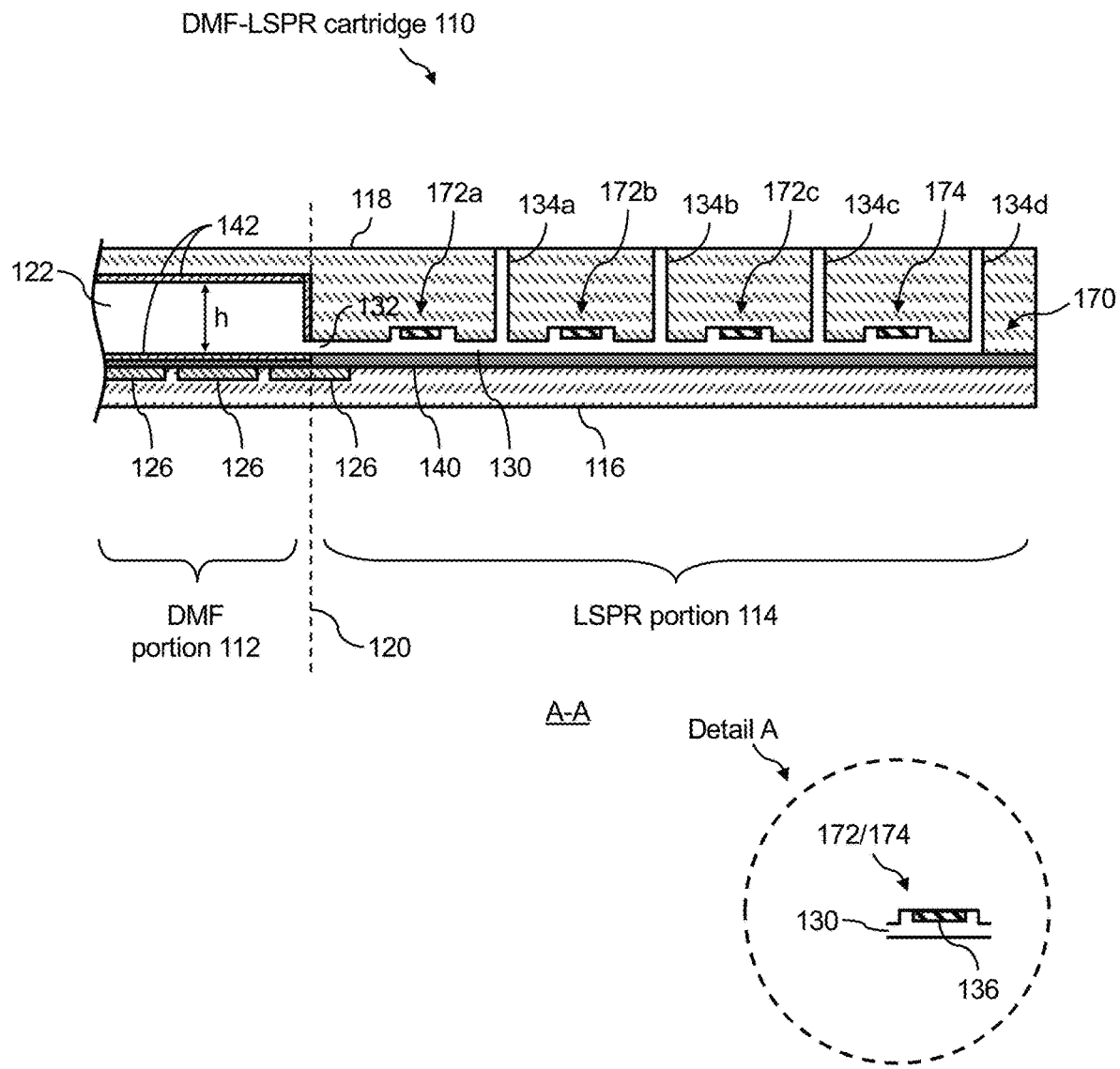
FIG. 25 is a cross-sectional view of an example of a DMF-LSPR cartridge showing another example of the in-line reference channel.

FIG. 25 is a cross-sectional view of the presently disclosed DMF-LSPR cartridge 110 and depicts another example of an in-line reference channel 170. For example, FIG. 25 is a partial cross-sectional view of DMF-LSPR cartridge 110 taken along line A-A of FIG. 21. In this example, in-line reference channel 170 may include (in order starting from boundary line interface 120) a first sample spot 172 (e.g., sample spot 172a), then a first outlet 134 (e.g., outlet 134a), then a second sample spot 172 (e.g., sample spot 172b), then a second outlet 134 (e.g., outlet 134b), then a third sample spot 172 (e.g., sample spot 172c), then a third outlet 134 (e.g., outlet 134c), then a reference spot 174, and then a fourth outlet 134 (e.g., outlet 134d). In one configuration and referring now to FIG. 26A, a schematic diagram shows outlet 134a may be fluidly coupled to a flow mechanism 158a, outlet 134b may be fluidly coupled to a flow mechanism 158b, outlet 134c may be fluidly coupled to a flow mechanism 158c, and outlet 134d may be fluidly coupled to a flow mechanism 158d. In this way, outlets 134a, 134b, 134c, and 134d may be independently controlled. However, in another configuration and referring now to FIG. 26B, a schematic diagram shows that outlets 134a, 134b, 134c, and 134d may be fluidly coupled to a common flow mechanism 158 and may be controlled separately by respective valves 176a, 176b, 176c, and 176d.

Figure 26A:
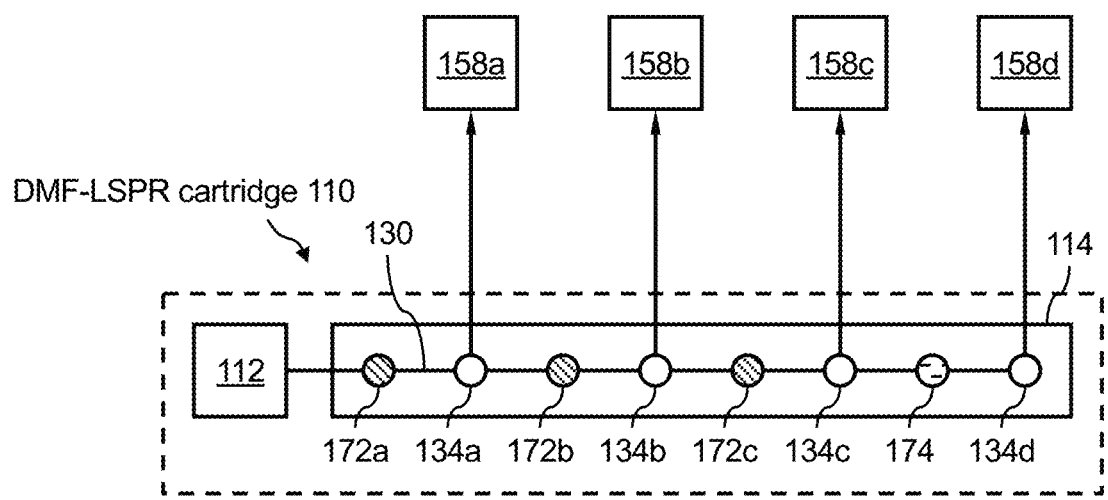
FIG. 26A and FIG. 26B are schematic diagrams of example of the DMF-LSPR cartridge and in-line reference channel shown in FIG. 25.
Figure 26B:
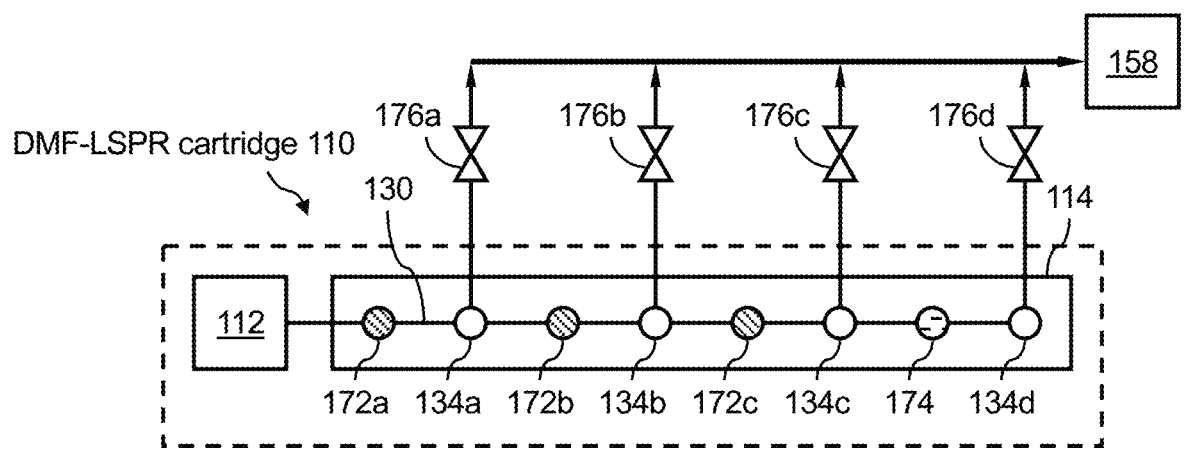
Figure 27:
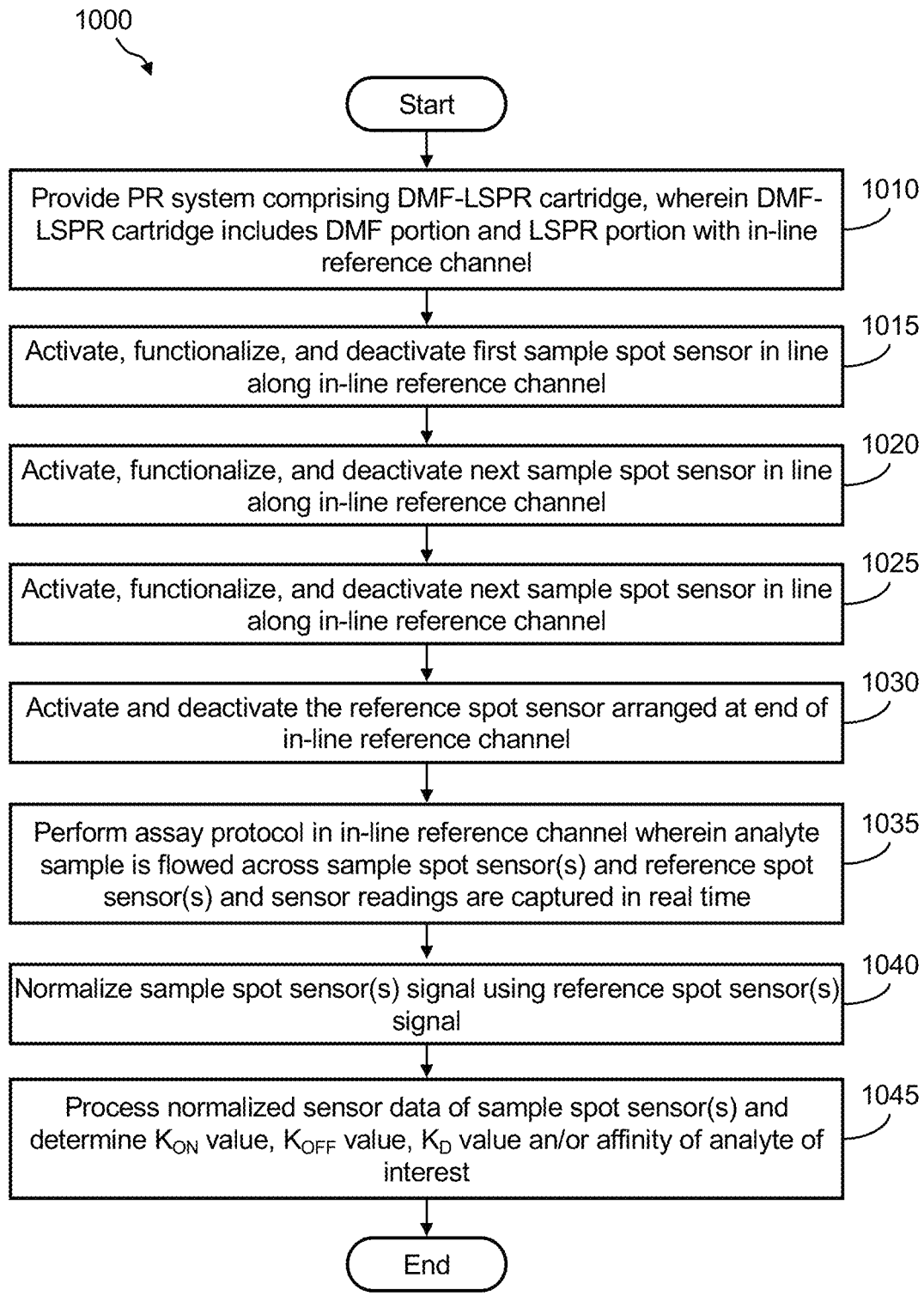
FIG. 27 is a flow diagram of an example of a method of using a DMF-LSPR cartridge and in-line reference channel.

FIG. 27 is a flow diagram of an example of a method 1000 of using DMF-LSPR cartridge 110 and in-line reference channel 170 shown in FIG. 25, FIG. 26A, and FIG. 26B, wherein method 1000 may include an example of a process of controlling the fluid flow with respect to in-line reference channel 170. Further, by way of example, method 1000 describes a process for a carboxyl group (COOH)-based DMF-LSPR cartridge 110. Additionally, while the steps of method 1000 correlate to the configuration of DMF-LSPR cartridge 110 and in-line reference channel 170 shown in FIG. 25, FIG. 26A, and FIG. 26B, this is exemplary only. The steps of method 1000 may be modified for any configuration of any number and/or arrangements of sample spots 172, reference spots 174, and/or outlets 134 and in any order. Method 1000 may include, but is not limited to, the following steps.

At a step 1010, PR system 800 may be provided that may include DMF-LSPR cartridge 110, wherein DMF-LSPR cartridge 110 may include DMF portion 112 and LSPR portion 114 that may include in-line reference channel 170, such as the in-line reference channel 170 shown in FIG. 25, FIG. 26A, and FIG. 26B.

At a step 1015, the first sample spot sensor along in-line reference channel 170 may be activated, then functionalized, and then deactivated. First, in an example activation process, a solution of EDC/NHS in an activation buffer may be supplied to in-line reference channel 170, flow mechanism 158a connected to outlet 134a is activated, while flow mechanisms 158b, 158c, and 158d connected to outlets 134b, 134c, and 134d, respectively, are not activated. In so doing, the solution may be flowed across sample spot 172a and the LSPR sensor 136 at sample spot 172a may be activated. At the same time, using flow mechanism 158a and outlet 134a, the flow of EDC/NHS solution may be diverted away from sample spots 172b and 172c as well as from reference spot 174. Next, in an example functionalization process, a solution of a first type of ligands may be supplied to in-line reference channel 170, flow mechanism 158a connected to outlet 134a is activated, while flow mechanisms 158b, 158c, and 158d connected to outlets 134b, 134c, and 134d, respectively, are not activated. In so doing, sample spot 172a may be functionalized by flowing a solution of ligands across the LSPR sensor 136 at sample spot 172a. At the same time, using flow mechanism 158a and outlet 134a, the flow of ligands may be diverted away from sample spots 172b and 172c as well as from reference spot 174. Next, in an example deactivation process, a "blocking" solution, such as ethanolamine, may be supplied to in-line reference channel 170, flow mechanism 158a connected to outlet 134a is activated, while flow mechanisms 158b, 158c, and 158d connected to outlets 134b, 134c, and 134d, respectively, are not activated. In so doing, ethanolamine may flow across the LSPR sensor 136 at sample spot 172a and thereby deactivates the LSPR sensor 136. At the same time, using flow mechanism 158a and outlet 134a, the flow of ethanolamine may be diverted away from sample spots 172*b* and 172*c* as well as from reference spot 174.

At a step 1020, the next sample spot sensor along in-line reference channel 170 may be activated, then functionalized, and then deactivated. First, in an example activation process, a solution of EDC/NHS in an activation buffer may be supplied to in-line reference channel 170, flow mechanism 158*b* connected to outlet 134*b* is activated, while flow mechanisms 158*a*, 158*c*, and 158*d* connected to outlets 134*a*, 134*c*, and 134*d*, respectively, are not activated. In so doing, the solution may be flowed across sample spot 172*b* and the LSPR sensor 136 at sample spot 172*b* may be activated. At the same time, using flow mechanism 158*b* and outlet 134*b*, the flow of EDC/NHS solution may be diverted away from sample spot 172*c* as well as from reference spot 174. Next, in an example functionalization process, a solution of a second type of ligands may be supplied to in-line reference channel 170, flow mechanism 158*b* connected to outlet 134*b* is activated, while flow mechanisms 158*a*, 158*c*, and 158*d* connected to outlets 134*a*, 134*c*, and 134*d*, respectively, are not activated. In so doing, sample spot 172*b* may be functionalized by flowing a solution of ligands across the LSPR sensor 136 at sample spot 172*b*. At the same time, using flow mechanism 158*b* and outlet 134*b*, the flow of ligands may be diverted away from sample spot 172*c* as well as from reference spot 174. Next, in an example deactivation process, a "blocking" solution, such as ethanolamine, may be supplied to in-line reference channel 170, flow mechanism 158*b* connected to outlet 134*b* is activated, while flow mechanisms 158*a*, 158*c*, and 158*d* connected to outlets 134*a*, 134*c*, and 134*d*, respectively, are not activated. In so doing, ethanolamine may flow across the LSPR sensor 136 at sample spot 172*b* and thereby deactivates the LSPR sensor 136. At the same time, using flow mechanism 158*b* and outlet 134*b*, the flow of ethanolamine may be diverted away from sample spot 172*c* as well as from reference spot 174. Sample spot 172*a* may be unaffected by any flow in this step because it is previously activated, functionalized, and deactivated.

At a step 1025, the next sample spot sensor along in-line reference channel 170 may be activated, then functionalized, and then deactivated. First, in an example activation process, a solution of EDC/NHS in an activation buffer may be supplied to in-line reference channel 170, flow mechanism 158*c* connected to outlet 134*c* is activated, while flow mechanisms 158*a*, 158*b*, and 158*d* connected to outlets 134*a*, 134*b*, and 134*d*, respectively, are not activated. In so doing, the solution may flow across sample spot 172*c* and the LSPR sensor 136 at sample spot 172*c* may be activated. At the same time, using flow mechanism 158*c* and outlet 134*c*, the flow of EDC/NHS solution may be diverted away from reference spot 174. Next, in an example functionalization process, a solution of a third type of ligands may be supplied to in-line reference channel 170, flow mechanism 158*c* connected to outlet 134*c* is activated, while flow mechanisms 158*a*, 158*b*, and 158*d* connected to outlets 134*a*, 134*b*, and 134*d*, respectively, are not activated. In so doing, sample spot 172*c* may be functionalized by flowing a solution of ligands across the LSPR sensor 136 at sample spot 172*c*. At the same time, using flow mechanism 158*c* and outlet 134*c*, the flow of ligands may be diverted away from reference spot 174. Next, in an example deactivation process, a "blocking" solution, such as ethanolamine, may be supplied to in-line reference channel 170, flow mechanism 158*c* connected to outlet 134*c* is activated, while flow mechanisms 158*a*, 158*b*, and 158*d* connected to outlets 134*a*, 134*b*, and 134*d*, respectively, are not activated. In so doing, ethanolamine may flow across the LSPR sensor 136 at sample spot 172*c* and thereby deactivates the LSPR sensor 136. At the same time, using flow mechanism 158*c* and outlet 134*c*, the flow of ethanolamine may be diverted away from reference spot 174. Sample spots 172*a* and 172*b* may be unaffected by any flow in this step because they are previously activated, functionalized, and deactivated.

At a step 1030, the reference spot sensor along in-line reference channel 170 may be activated and then deactivated. First, in an example activation process, a solution of EDC/NHS in an activation buffer may be supplied to in-line reference channel 170, flow mechanism 158*d* connected to outlet 134*d* is activated, while flow mechanisms 158*a*, 158*b*, and 158*c* connected to outlets 134*a*, 134*b*, and 134*c*, respectively, are not activated. In so doing, the solution may flow across reference spot 174 and the LSPR sensor 136 at reference spot 174 may be activated. Next, in an example deactivation process, a "blocking" solution, such as ethanolamine, may be supplied to in-line reference channel 170, flow mechanism 158*d* connected to outlet 134*d* is activated, while flow mechanisms 158*a*, 158*b*, and 158*c* connected to outlets 134*a*, 134*b*, and 134*c*, respectively, are not activated. In so doing, ethanolamine may flow across the LSPR sensor 136 at reference spot 174 and thereby may deactivate the LSPR sensor 136. Sample spots 172*a*, 172*b*, and 172*c* may be unaffected by any flow in this step because they are previously activated, functionalized, and deactivated.

In another example of method 1000 and in particular of steps 1015, 1020, 1025, and 1030, all of the sensors may be activated at the same time rather than in separate steps. For example, in one step, the solution of EDC/NHS may be supplied across all spots (e.g., sample spots 172*a*, 172*b*, and 172*c* and reference spot 174) and out of outlet 134*d*. In so doing, all of the sensor surfaces may be activated in one step, which saves time compared to the individual activation steps. This process may still include that each of the LSPR sensors 136 are individually functionalized and then individually deactivated as described above in steps 1015, 1020, 1025, and 1030.

At a step 1035, the assay protocol may be performed in in-line reference channel 170 wherein the analyte sample may be flowed across the sample spot sensor(s) and the reference spot sensor(s) and sensor readings are captured in real time. For example, an assay protocol may be performed in which the analyte sample is supplied to in-line reference channel 170. Next, running buffer may be transported over the sensor surfaces for a set period of time (to capture the dissociation phase). Next, if needed, a regeneration buffer may be transported over the sensor surfaces to remove any analyte remaining after the dissociation period. Next, a different concentration of analyte may be injected (usually 3× the previous one) and the above is repeated. This is typically done for at least three analyte concentrations to perform the kinetic analysis.

In step 1035, flow mechanism 158*d* connected to outlet 134*d* may be activated, while flow mechanisms 158*a*, 158*b*, and 158*c* connected to outlets 134*a*, 134*b*, and 134*c*, respectively, are not activated. In so doing, the analyte sample may be flowed along the full length of in-line reference channel 170 and across the LSPR sensors 136 at sample spots 172*a*, 172*b*, and 172*c* and the LSPR sensor 136 at reference spot 174. At the same time, using illumination sources 154 and optical measurement device 156, the LSPR signals from the LSPR sensors 136 at sample spots 172*a*, 172*b*, and 172*c* and the LSPR signal from LSPR sensor 136 at reference spot 174 may be captured in real time while running the assay protocol.

At a step 1040, the sample spot sensor(s) signal may be normalized using the reference spot sensor(s) signal. For example, the signal of LSPR sensor 136 at reference spot 174 may be used to normalize the signal of the LSPR sensors 136 at sample spots 172a, 172b, and 172c. For example, the signal of LSPR sensor 136 at reference spot 174 may be used to subtract out from the signal of each of the LSPR sensors 136 at sample spots 172a, 172b, and 172c any non-specific binding of the analyte to the sensor, any instrument drift, any bulk refractive index shifts, and so on.

At a step 1045, the normalized sensor data from the sample spot sensor(s) may be processed and the $K_{ON}$ value, $K_{OFF}$ value, $K_D$ value, and/or affinity of the analyte of interest may be determined. For example, using controller 150 of PR system 800, the normalized sensor data from each of the LSPR sensors 136 at sample spots 172a, 172b, and 172c may be processed by fitting a binding model to the data and using a regression to find the $K_{ON}$ value, $K_{OFF}$ value, $K_D$ value, and/or affinity of the analyte of interest that best represents the experimental data. This may be accomplished using a data set that may include, for example, the at least three analyte concentrations described in step 1035.

The configuration of in-line reference channel 170 shown in FIG. 25, FIG. 26A, and FIG. 26B and utilized in method 1000 of FIG. 27 may allow one analyte sample flowing down in-line reference channel 170 to be monitored by multiple different ligand interactions and facilitates a DMF-LSPR cartridge 110 that is configured for high throughput.

Figure 28:
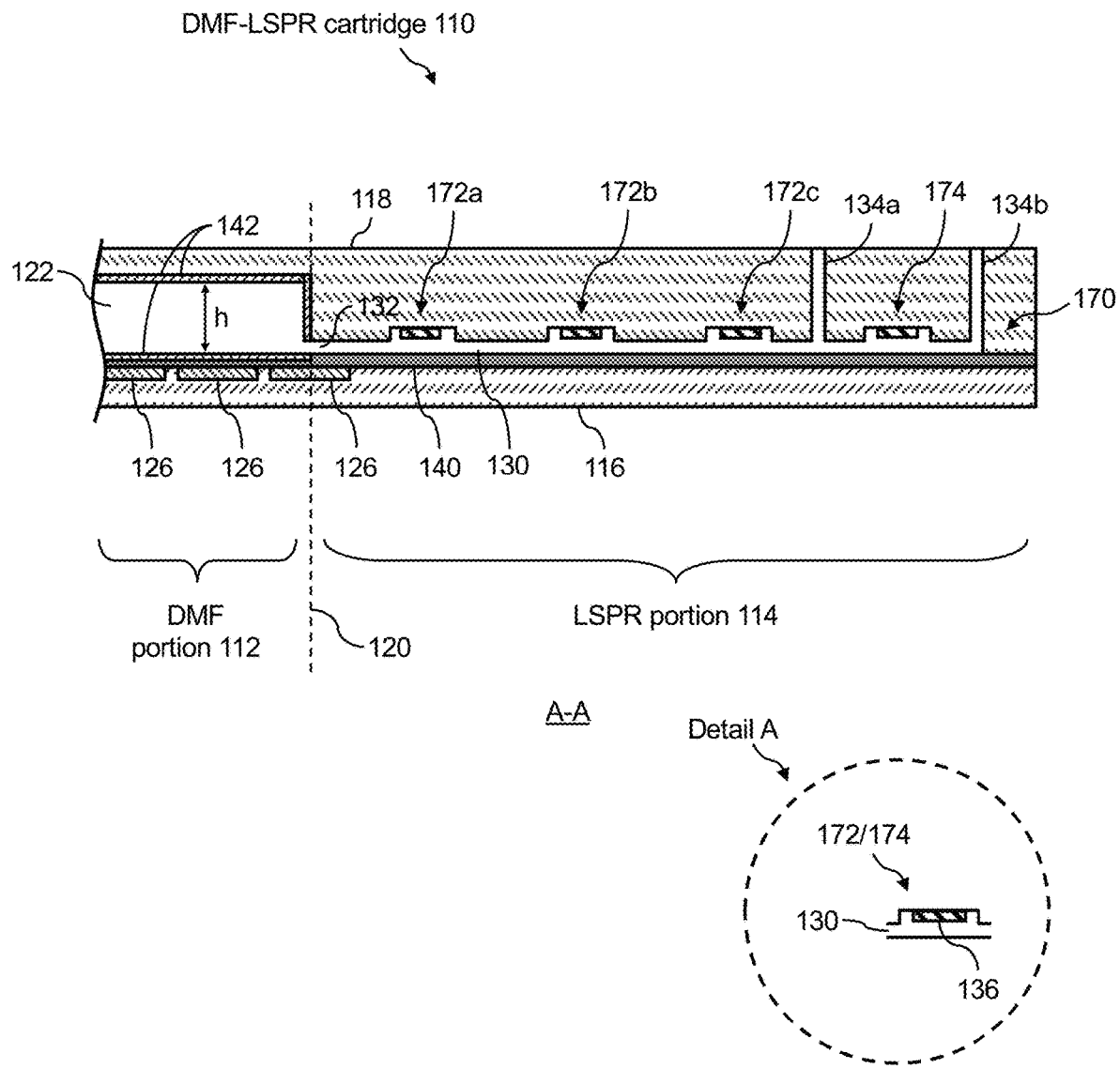
FIG. 28 is a cross-sectional view of an example of a DMF-LSPR cartridge showing yet another example of the in-line reference channel.

FIG. 28 is a cross-sectional view of the presently disclosed DMF-LSPR cartridge 110 and depicts another example of in-line reference channel 170. For example, FIG. 28 is a partial cross-sectional view of DMF-LSPR cartridge 110 taken along line A-A of FIG. 21. In this example, in-line reference channel 170 may include (in order starting from boundary line interface 120) a first sample spot 172 (e.g., sample spot 172a), then a second sample spot 172 (e.g., sample spot 172b), then a third sample spot 172 (e.g., sample spot 172c), then a first outlet 134 (e.g., outlet 134a), then a reference spot 174, and then a second outlet 134 (e.g., outlet 134b). In one configuration and referring now to FIG. 29A, a schematic diagram shows outlet 134a may be fluidly coupled to a flow mechanism 158a and outlet 134b may be fluidly coupled to a flow mechanism 158b. In this way, outlets 134a and 134b may be independently controlled. However, in another configuration and referring now to FIG. 29B, a schematic diagram shows outlets 134a and 134b may be fluidly coupled to a common flow mechanism 158 and controlled separately by respective valves 176a and 176b.

Figure 29A:
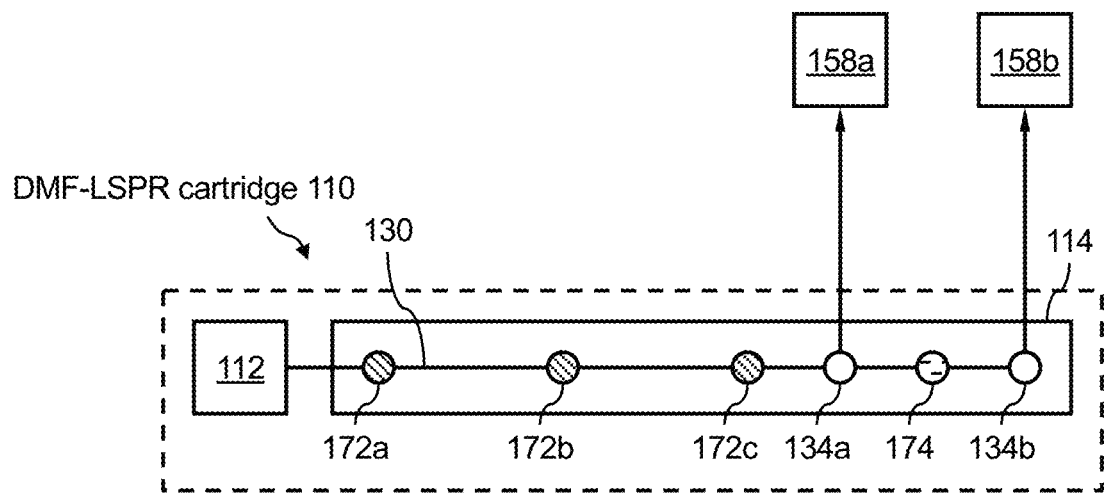
FIG. 29A and FIG. 29B are schematic diagrams of examples of the DMF-LSPR cartridge and in-line reference channel shown in FIG. 28.
Figure 29B:
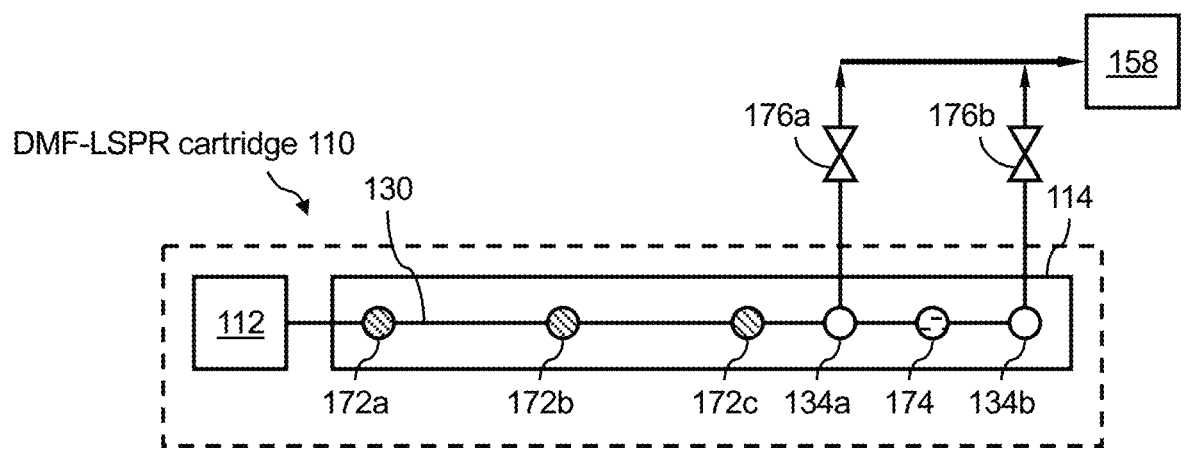
Figure 30:
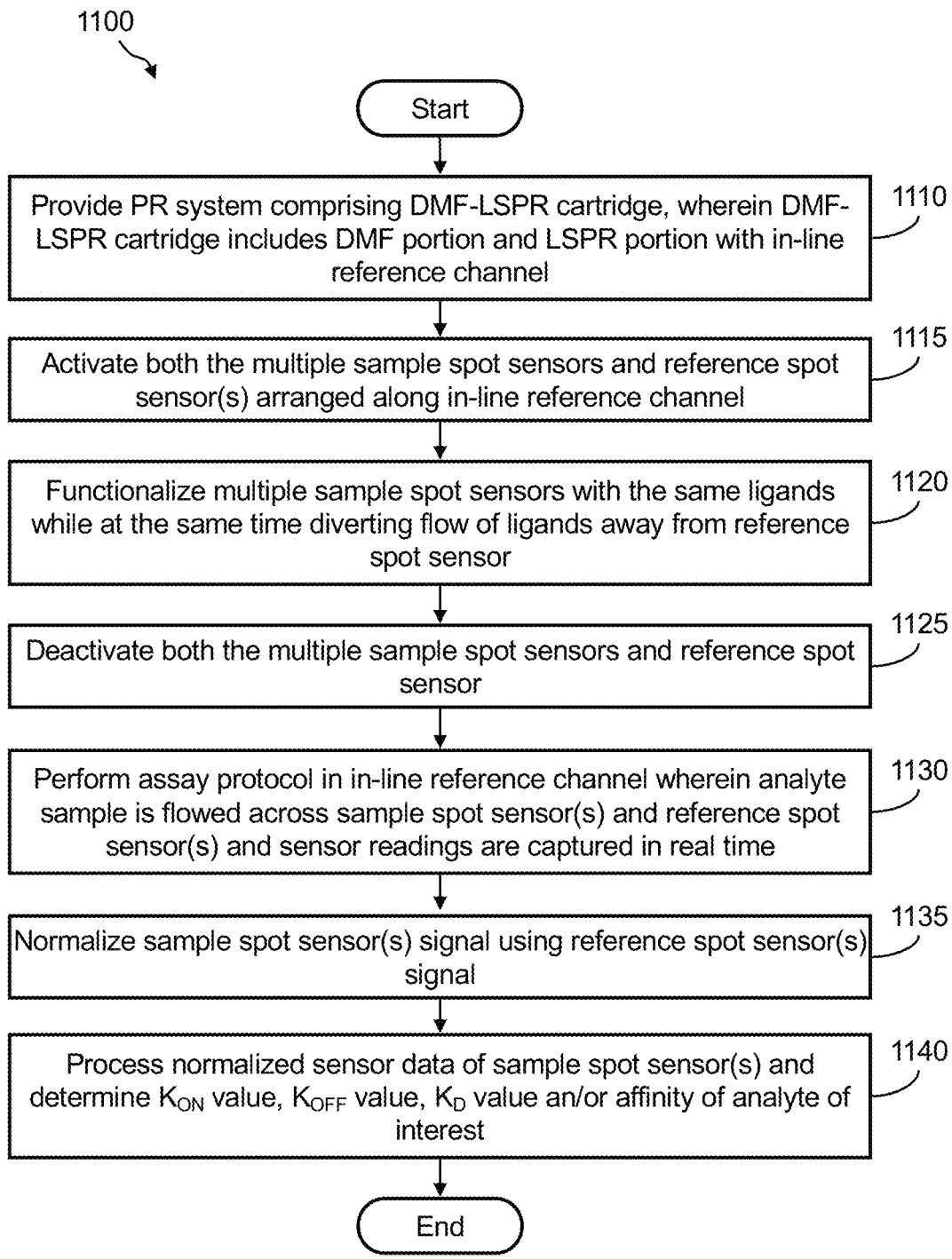
FIG. 30 is a flow diagram of an example of a method of using the DMF-LSPR cartridge and in-line reference channel shown in FIG. 28.

FIG. 30 is a flow diagram of an example of a method 1100 of using DMF-LSPR cartridge 110 and in-line reference channel 170 shown in FIG. 28, FIG. 29A, and FIG. 29B, wherein method 1100 may include an example of a process of controlling the fluid flow with respect to in-line reference channel 170. Further, by way of example, method 1100 describes a process for a carboxyl group (COOH)-based DMF-LSPR cartridge 110. Additionally, while the steps of method 1100 correlate to the configuration of DMF-LSPR cartridge 110 and in-line reference channel 170 shown in FIG. 28, FIG. 29A, and FIG. 29B, this is exemplary only. The steps of method 1100 may be modified for any configuration of any number and/or arrangements of sample spots 172, reference spots 174, and/or outlets 134 and in any order. Method 1100 may include, but is not limited to, the following steps.

At a step 1110, PR system 800 may be provided that may include DMF-LSPR cartridge 110, wherein DMF-LSPR cartridge 110 may include DMF portion 112 and LSPR portion 114 that has in-line reference channel 170, such as the in-line reference channel 170 shown in FIG. 28, FIG. 29A, and FIG. 29B.

At a step 1115, both the sample spot sensor(s) and reference spot sensor(s) that are arranged along in-line reference channel 170 may be activated. For example, a solution of EDC/NHS in an activation buffer may be supplied to in-line reference channel 170, flow mechanism 158a connected to outlet 134a is not activated, while flow mechanism 158b connected to outlet 134b is activated. In so doing, the solution may be flowed along the full length of in-line reference channel 170 and both the LSPR sensors 136 at sample spots 172a, 172b, and 172c, as well as the LSPR sensor 136 at reference spot 174 may be activated.

At a step 1120, the multiple sample spot sensors may be functionalized with the same ligands. For example, a solution of ligands may be supplied to in-line reference channel 170, flow mechanism 158a connected to outlet 134a is activated, while flow mechanism 158b connected to outlet 134b is not activated. In so doing, the solution flows across the LSPR sensors 136 of sample spots 172a, 172b, and 172c and the LSPR sensors 136 of sample spots 172a, 172b, and 172c may be functionalized with the same type of ligands. At the same time, using flow mechanism 158a and outlet 134a, the flow of ligands may be diverted away from reference spot 174 so that the LSPR sensor 136 of reference spot 174 is not exposed to the ligand solution.

At a step 1125, both the multiple sample spot sensors and reference spot sensors that are arranged along in-line reference channel 170 may be deactivated. For example, a "blocking" solution, such as ethanolamine, may be supplied to in-line reference channel 170, flow mechanism 158b connected to outlet 134b may be activated, while flow mechanism 158a connected to outlet 134a is not activated. In so doing, ethanolamine may flow along the full length of in-line reference channel 170 and across the LSPR sensors 136 of sample spots 172a, 172b, and 172c and the LSPR sensor 136 of reference spot 174 and thereby deactivates all of the LSPR sensors 136.

At a step 1130, the assay protocol may be performed in in-line reference channel 170 wherein the analyte sample is flowed across the sample spot sensor(s) and the reference spot sensor(s) and sensor readings may be captured in real time. For example, an assay protocol may be performed in which the analyte sample is supplied to in-line reference channel 170. Next, running buffer may be transported over the sensor surfaces for a set period of time (to capture the dissociation phase). Next, if needed, a regeneration buffer may be transported over the sensor surfaces to remove any analyte remaining after the dissociation period. Next, a different concentration of analyte may be injected (usually 3× the previous one) and the above is repeated. This is typically done for at least three analyte concentrations to perform the kinetic analysis.

In step 1130, flow mechanism 158b connected to outlet 134b may be activated, while flow mechanism 158a connected to outlet 134a is not activated. In so doing, the analyte sample may be flowed along the full length of in-line reference channel 170 and across the LSPR sensors 136 at sample spots 172a, 172b, and 172c and the LSPR sensor 136 at reference spot 174. At the same time, using illumination sources 154 and optical measurement device 156, the LSPR signals from the LSPR sensors 136 at sample spots 172a, 172b, and 172c and the LSPR signal from LSPR sensor 136 at reference spot 174 may be captured in real time while running the assay protocol.

At a step 1135, the sample spot sensor(s) signal may be normalized using the reference spot sensor(s) signal. For example, the signal of LSPR sensor 136 at reference spot 174 may be used to normalize the signal of the LSPR sensors 136 at sample spots 172a, 172b, and 172c. For example, the signal of LSPR sensor 136 at reference spot 174 may be used to subtract out from the signal of each of the LSPR sensors 136 at sample spots 172a, 172b, and 172c any non-specific binding of the analyte to the sensor, any instrument drift, any bulk refractive index shifts, and so on.

At a step 1140, the normalized sensor data from the sample spot sensor(s) may be processed and the $K_{ON}$ value, $K_{OFF}$ value, $K_D$ value, and/or affinity of the analyte of interest may be determined. For example, using controller 150 of PR system 800, the normalized sensor data from each of the LSPR sensors 136 at sample spots 172a, 172b, and 172c may be processed by fitting a binding model to the data and using a regression to find the $K_{ON}$ value, $K_{OFF}$ value, $K_D$ value, and/or affinity of the analyte of interest that best represents the experimental data. This may be accomplished using a data set that may include, for example, the at least three analyte concentrations described in step 1130.

The configuration of in-line reference channel 170 shown in FIG. 28, FIG. 29A, and FIG. 29B and utilized in method 1100 of FIG. 30 may allow one analyte sample flowing down in-line reference channel 170 to be monitored by multiple sample spots functionalized with the same ligand and provides triplicate measurements of the same ligand interaction with respect to a reference.

Figure 31:
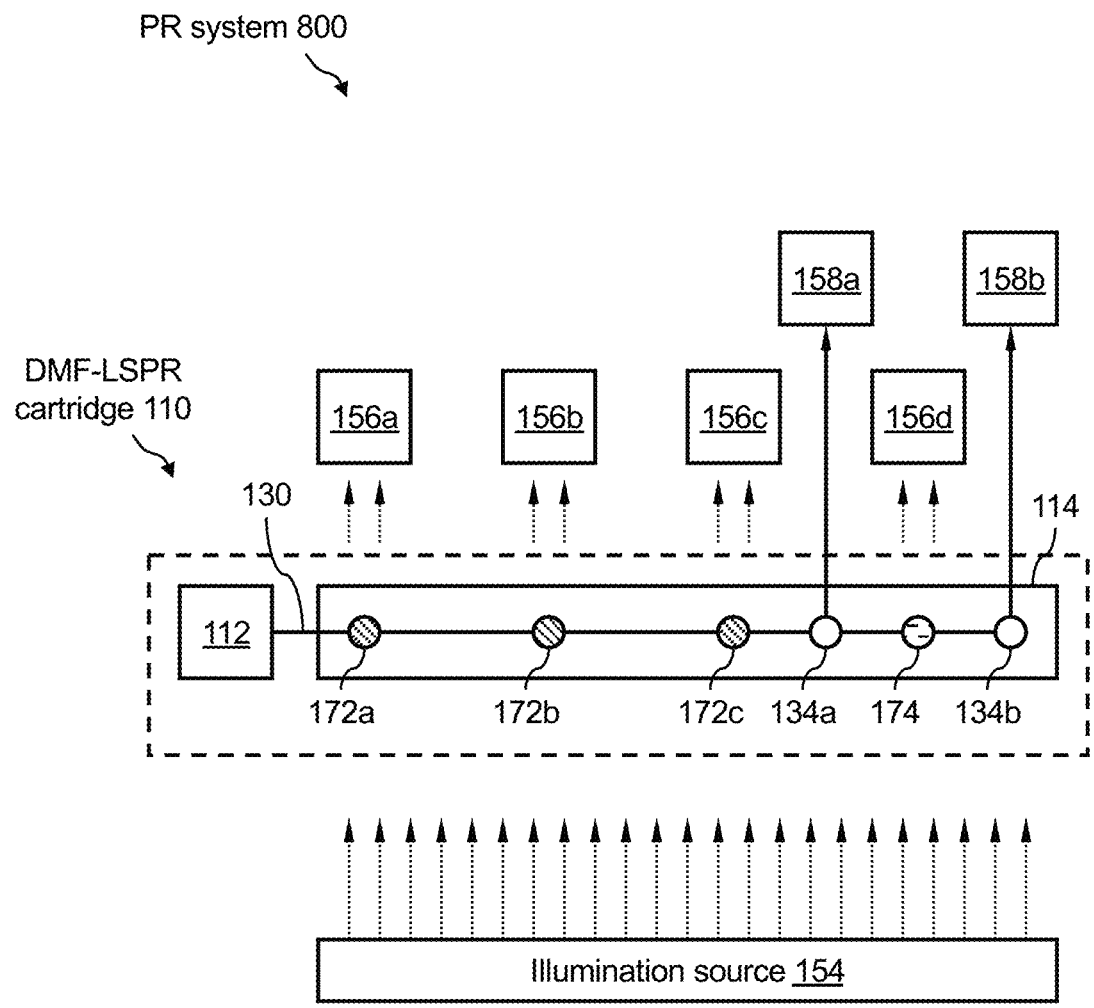
FIG. 31 and FIG. 32 are schematic diagrams of examples of optical detection systems in relation to the in-line reference channel of the presently disclosed DMF-LSPR cartridge.
Figure 32:
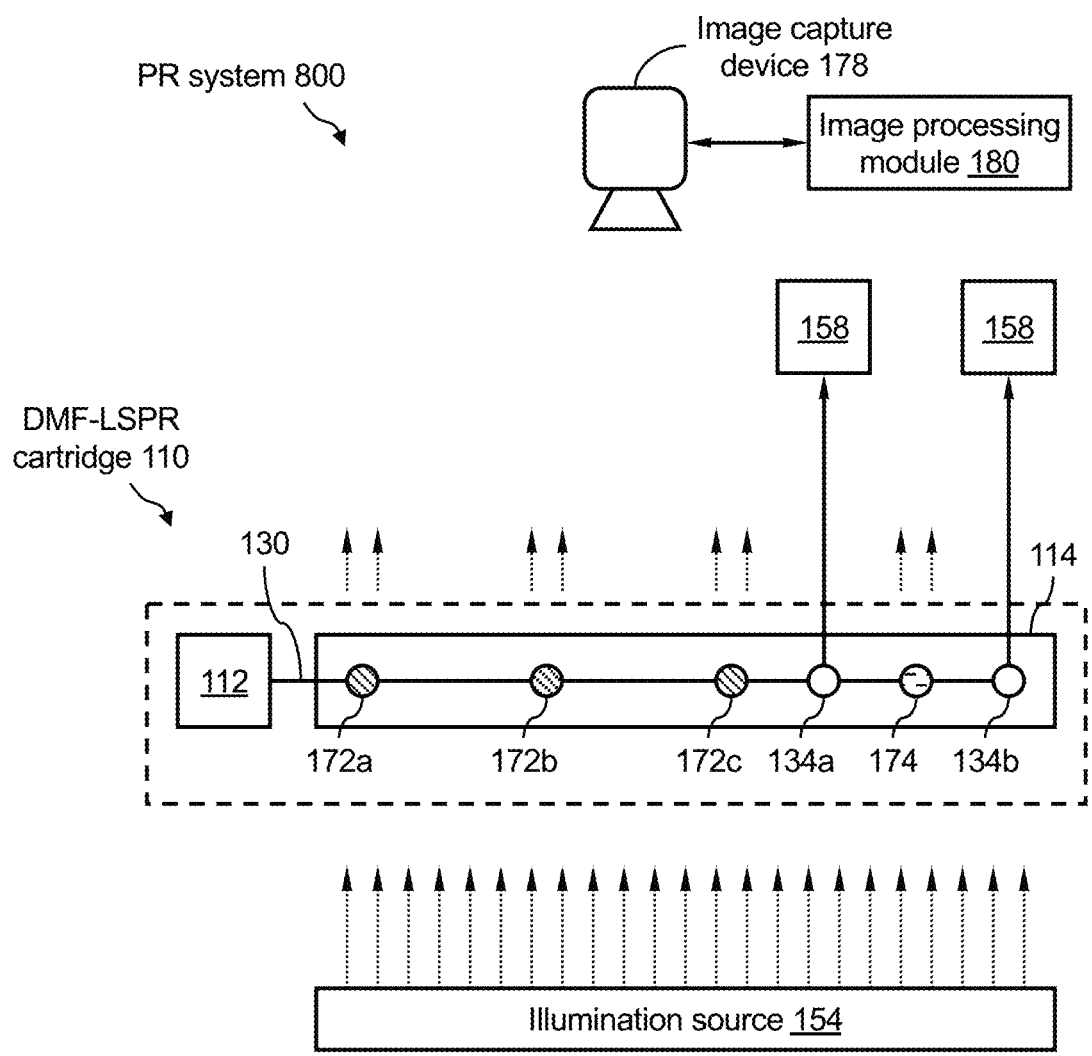
Figure 33:
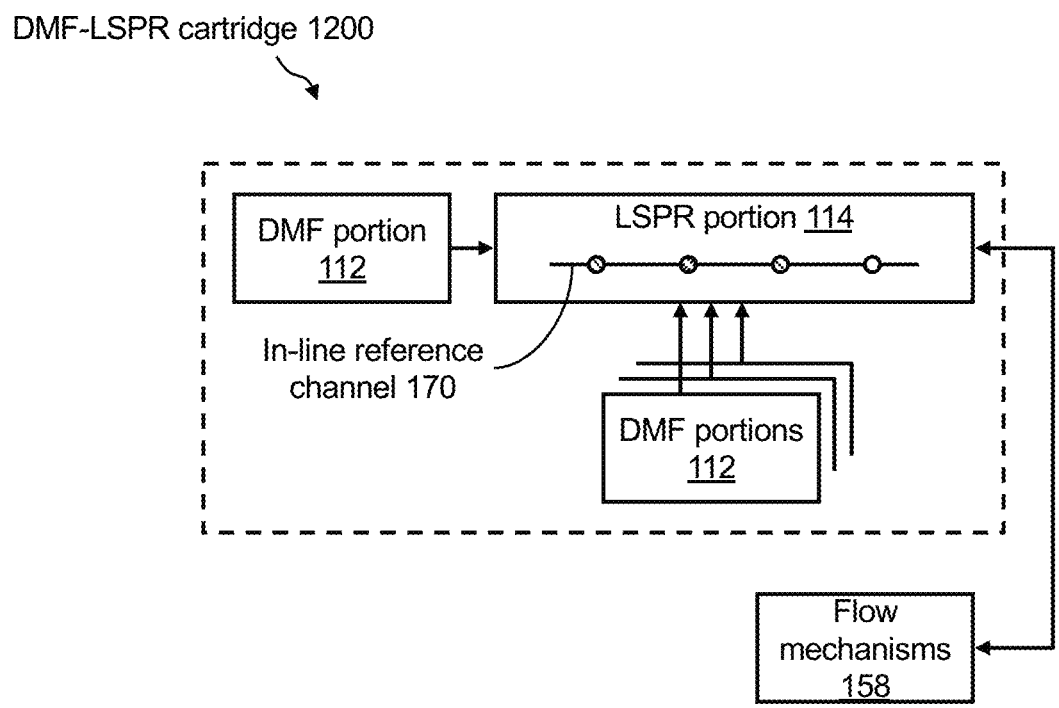
FIG. 33, FIG. 34, FIG. 35, and FIG. 36 are schematic diagrams of examples of DMF-LSPR cartridges that include one LSPR portion supplied by multiple DMF portions.

FIG. 31 and FIG. 32 show schematic diagrams of examples of optical detection systems in relation to the in-line reference channel 170 of the presently disclosed DMF-LSPR cartridge 110. In one configuration, FIG. 31 shows LSPR portion 114 of DMF-LSPR cartridge 110 that may include multiple LSPR sensors. For example, LSPR portion 114 may include sample spots 172a, 172b, and 172c and one reference spot 174, wherein each spot may include an LSPR sensor 136. In this example, each of the sample spots 172a, 172b, and 172c and the reference spot 174 may have a dedicated optical measurement device 156 for capturing readings therefrom. For example, optical measurement device 156a may be directed toward sample spot 172a, optical measurement device 156b may be directed toward sample spot 172b, optical measurement device 156c may be directed toward sample spot 172c, and optical measurement device 156d may be directed toward reference spot 174.

Optical measurement devices 156a, 156b, 156c, and 156d (e.g., spectrometers) may be arranged on one side of DMF-LSPR cartridge 110 and illumination sources 154 may be arranged on the other side of DMF-LSPR cartridge 110. In this configuration, white light from illumination sources 154 may be directed at and pass through each of the LSPR sensors 136 of sample spots 172a, 172b, and 172c and reference spot 174. Then, as the sample analyte flows through in-line reference channel 170 and across all of the LSPR sensors 136, each of the optical measurement devices 156 may capture in real time the optical LSPR signal emitted from its corresponding LSPR sensor 136. In LSPR portion 114 of DMF-LSPR cartridge 110, the arrangement of illumination sources 154, the LSPR sensors 136 of sample spots 172 and reference spot 174, and optical measurement devices 156 may provide an optical detection system that operates in transmission mode.

The presently disclosed PR system 800 is not limited to multiple optical measurement devices 156 that correspond to the respective LSPR sensors 136 in in-line reference channel 170. In another configuration and referring now to FIG. 32, the multiple optical measurement devices 156 in PR system 800 may be replaced with a single image capture device 178. Image capture device 178 may be any image capture device that is suitable for use in a portable device, such as, but not limited to, the types of digital cameras that may be installed in mobile phones, other digital cameras, wide angle digital cameras, 360 degree digital cameras, infrared (IR) cameras, digital video cameras, and the like. The image data from image capture device 178 may be provided in any standard or proprietary image file format (e.g., JPEG, TIFF, BMP, etc.).

Image capture device 178 may be directed toward in-line reference channel 170 wherein all of the LSPR sensors 136 of sample spots 172 and reference spot 174 are within its field of view. Accordingly, as the sample analyte flows through in-line reference channel 170 and across all of the LSPR sensor 136, image capture device 178 may be used to capture images of LSPR sensor 136 in real time. Each image captured using image capture device 178 may be processed, for example, using an image processing module 180. For example, each image may include all of the LSPR sensors 136 of sample spots 172 and reference spot 174 and image processing module 180 may be used to process the image data (e.g., spatial and intensity information) at each spot to provide separate readings for each spot. In other examples, image capture device 178 may be a hyperspectral camera that can take images that include spatial and spectral data versus a camera that can provide spatial and intensity data only.

Referring again to FIG. 20 through FIG. 32, the presently disclosed PR system 800 and DMF-LSPR cartridge 110 is not limited to the configurations of in-line reference channel 170, sample spots 172, reference spots 174, outlets 134, optical measurement devices 156, and flow mechanisms 158 shown therein. For example, in-line reference channel 170 of DMF-LSPR cartridge 110 may include any number and/or arrangements of sample spots 172, reference spots 174, and/or outlets 134 and in any order. Accordingly, PR system 800 may include any number and/or arrangements of illumination sources 154, optical measurement devices 156, flow mechanisms 158, and/or image capture devices 178. Additionally, so that the sample fluid at each of the various "spots" (e.g., sample spot(s) 172 and reference spot(s) 174) along in-line reference channel 170 is substantially the same, adjacent "spots" are preferably spaced as close together as possible.

Further, the presently disclosed PR system 800 is not limited to a cartridge (e.g., DMF-LSPR cartridge 110) that may include one DMF portion 112 and one LSPR portion 114 only. For example and referring now to FIG. 33, a schematic diagram is provided of a DMF-LSPR cartridge 1200 that may include one LSPR portion 114 that may further include the in-line reference channel 170, wherein the in-line reference channel 170 may be supplied by multiple DMF portions 112. For example, the inlet of in-line reference channel 170 may be supplied by one DMF portion 112 and then each of the multiple sample spots 172 and reference spot 174 along in-line reference channel 170 may be supplied by its own dedicated DMF portion 112. In this way, using droplet operations of a certain DMF portion 112, fluid at each spot may be manipulated individually in and out of in-line reference channel 170. Further, using the respective DMF portions 112, the fluid supplying each spot may be processed independently and differently from other spots. For example, using the multiple DMF portions 112, different ligands may be immobilized at the different sample spots 172.

Figure 34:
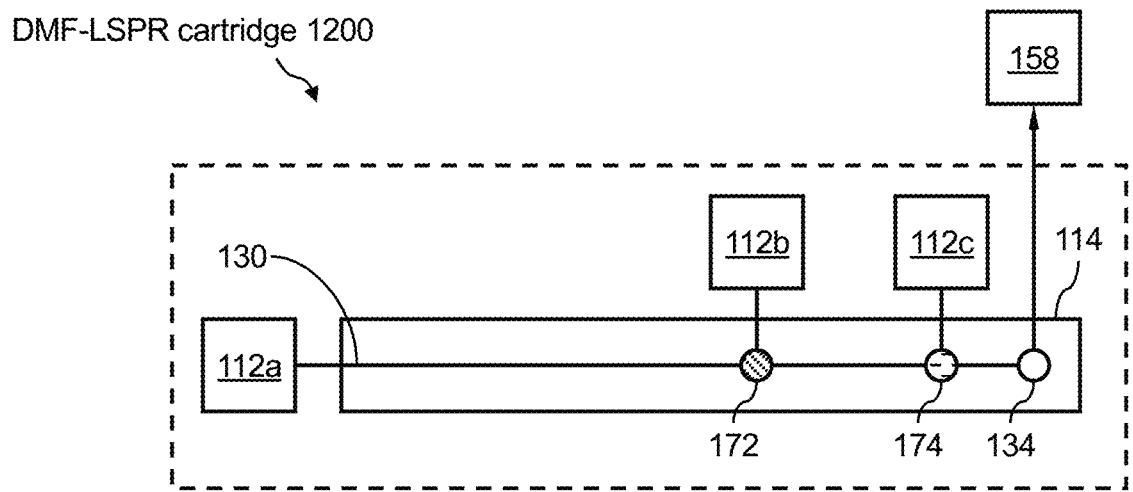

In one example, FIG. 34 shows a DMF-LSPR cartridge 1200 that may include a DMF portion 112a supplying the inlet of in-line reference channel 170 of LSPR portion 114, a DMF portion 112b supplying one sample spot 172, and a DMF portion 112c supplying one reference spot 174. In this example, there may be one outlet 134 connected to a flow mechanism 158 at the end of in-line reference channel 170.

Figure 35:
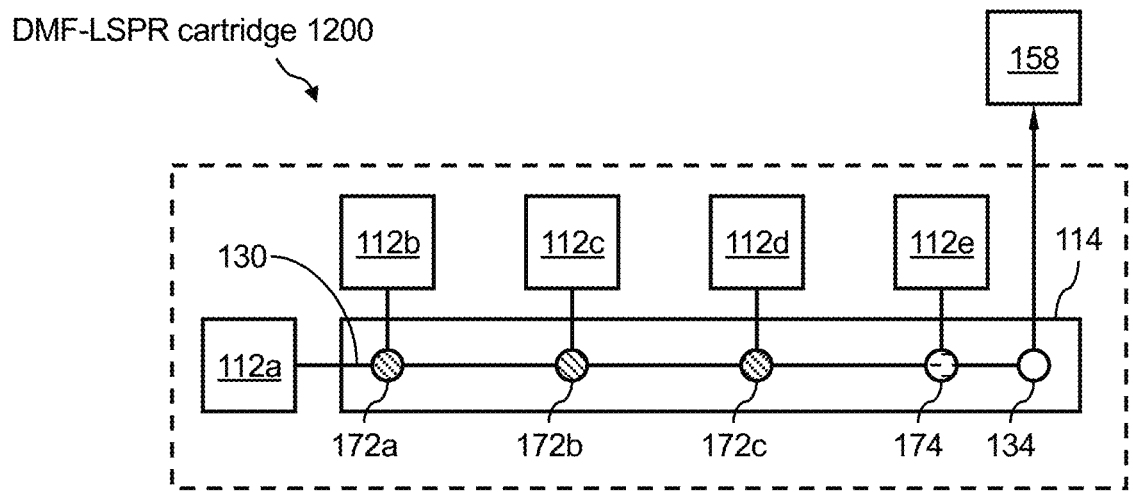

In another example, FIG. 35 shows a DMF-LSPR cartridge 1200 that may include a DMF portion 112a supplying the inlet of in-line reference channel 170 of LSPR portion 114, a DMF portion 112b supplying a sample spot 172a, a DMF portion 112c supplying a sample spot 172b, a DMF portion 112d supplying a sample spot 172c, and a DMF portion 112e supplying one reference spot 174. In this example, there may be one outlet 134 connected to a flow mechanism 158 at the end of in-line reference channel 170.

Figure 36:
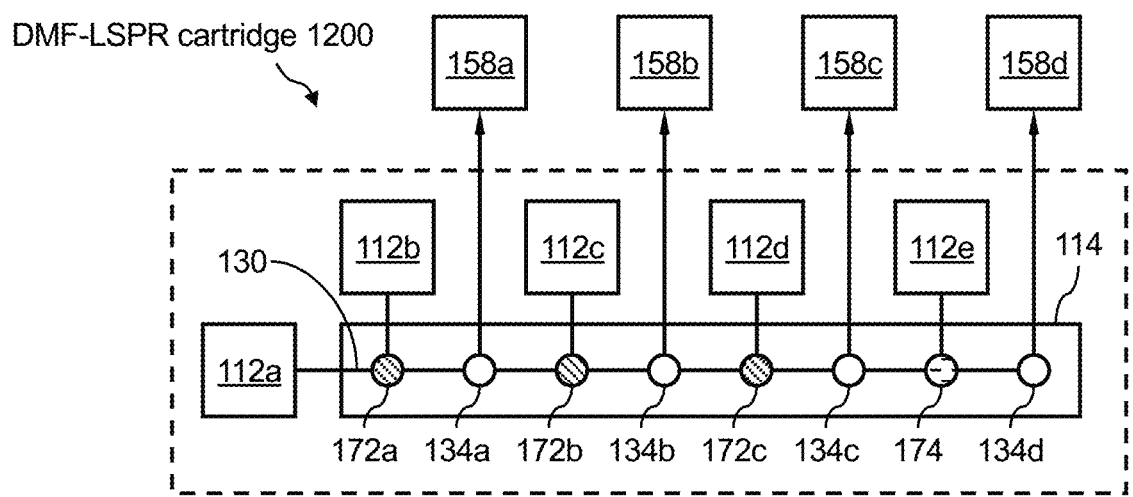

In yet another example, FIG. 36 shows a DMF-LSPR cartridge 1200 that may include a DMF portion 112a supplying the inlet of in-line reference channel 170 of LSPR portion 114, a DMF portion 112b supplying a sample spot 172a, a DMF portion 112c supplying a sample spot 172b, a DMF portion 112d supplying a sample spot 172c, and a DMF portion 112e supplying one reference spot 174. In this example, an outlet 134a connected to flow mechanism 158a may be provided between sample spot 172a and sample spot 172b. An outlet 134b connected to flow mechanism 158b may be provided between sample spot 172b and sample spot 172c. An outlet 134c connected to flow mechanism 158c may be provided between sample spot 172c and reference spot 174. An outlet 134d connected to flow mechanism 158d may be provided at the end of in-line reference channel 170.

DMF-LSPR cartridge 1200 is not limited to the examples shown in FIG. 33, FIG. 34, FIG. 35, and FIG. 36. DMF-LSPR cartridge 1200 can include any in-line reference channel 170 with any configurations of sample spots 172, reference spots 174, and outlets 134 and can include any number and configuration of DMF portions 112 supplying in-line reference channel 170 of LSPR portion 114.

Figure 37:
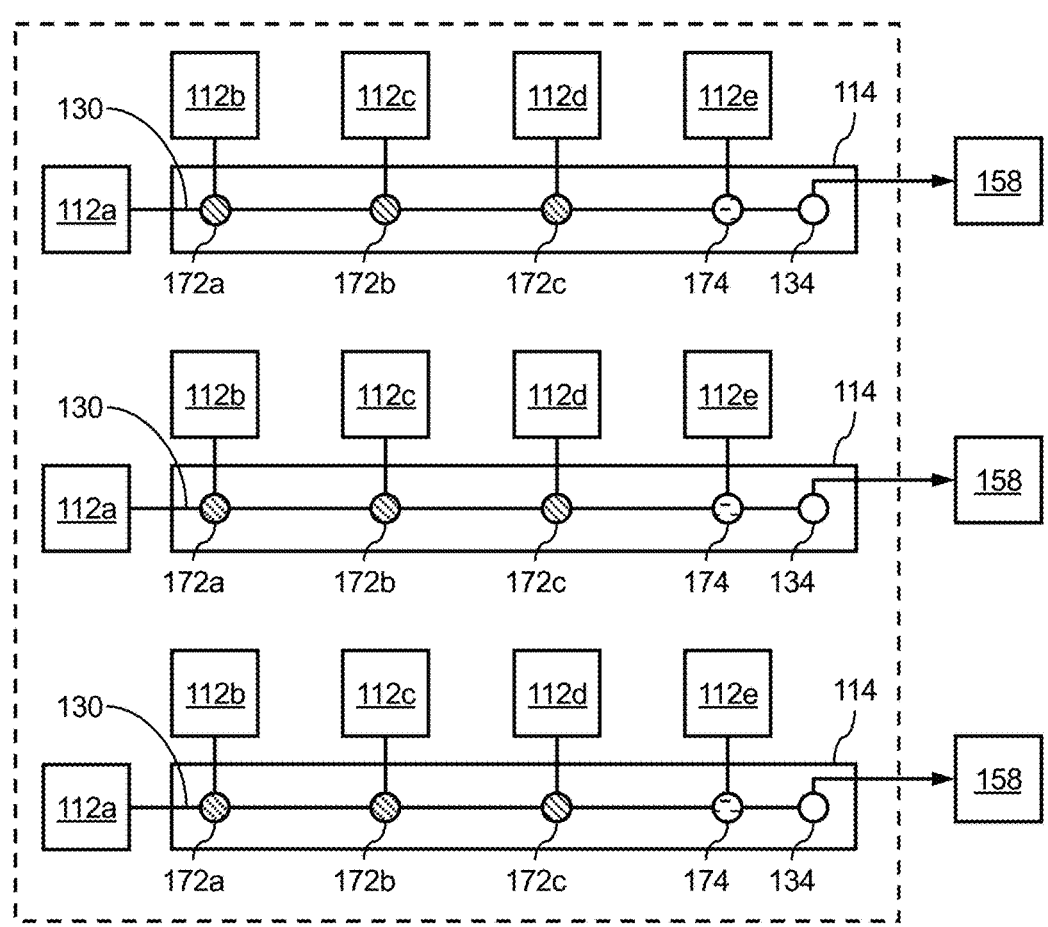
FIG. 37 is a schematic diagram of an example of a multiple-channel DMF-LSPR cartridge.

Further, any of the configurations and/or designs shown in FIG. 20 through FIG. 36 may be repeated on the same DMF-LSPR cartridge to support multiple channels. In one example, FIG. 37 shows the DMF-LSPR cartridge 1200 of FIG. 35 repeated multiple times (e.g., three times) to form a multiple-channel DMF-LSPR cartridge 1300. Again, the configuration shown in FIG. 35 is exemplary only. DMF-LSPR cartridge 1200 may include any DMF-LSPR configurations and/or designs and repeated any number of times.

Figure 38:
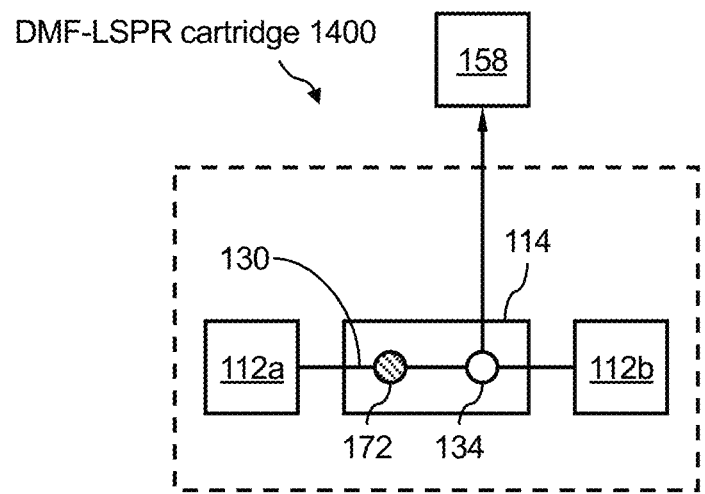
FIG. 38 is a schematic diagram of an example of a DMF-LSPR cartridge that may include a first DMF portion supplying the inlet of the in-line reference channel and wherein the outlet of the in-line reference channel supplies a second DMF portion.

In yet another example, FIG. 38 shows a schematic diagram of an example of a DMF-LSPR cartridge 1400 that may include a first DMF portion 112 (e.g., DMF portion 112a) that supplies the inlet of in-line reference channel 170 and wherein the outlet of in-line reference channel 170 supplies a second DMF portion 112 (e.g., DMF portion 112b). In this configuration, DMF portion 112a may supply the inlet of in-line reference channel 170 as described hereinabove in FIG. 20 through FIG. 37. Further, DMF portion 112b may be used to capture and process the fluid is coming through in-line reference channel 170. For example, DMF portion 112b may be used to re-use and/or reprocess the fluid after it passes through in-line reference channel 170.

Figure 39:
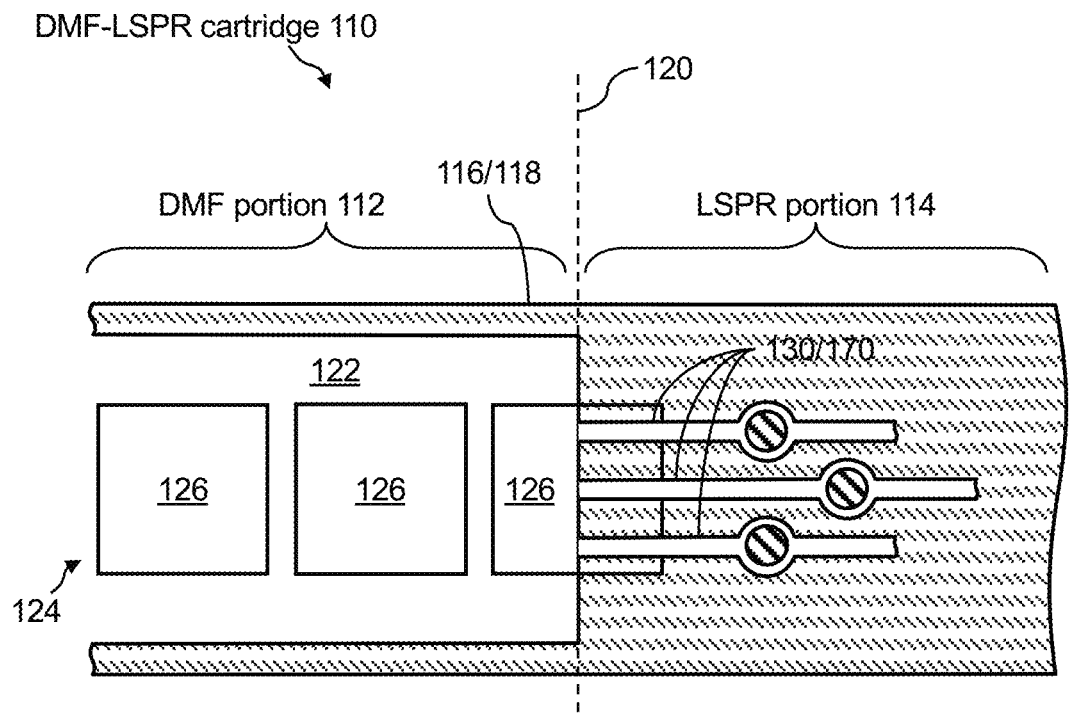
FIG. 39 is a plan view of an example of a single boundary droplet operations electrode of the DMF-LSPR cartridge that supplies multiple fluid channels.

In yet another example, FIG. 39 shows a plan view of an example of a boundary droplet operations electrode 126 of DMF-LSPR cartridge 110 that supplies multiple fluid channels 130 and/or multiple in-line reference channels 170. In this example, boundary droplet operations electrode 126 may supply three fluid channels 130. The three fluid channels 130 may remain independent for a triplicate measurement or the three fluid channels 130 may merge together to form one channel, which may be useful to reduce or substantially eliminate dead volume at the interface between DMF portion 112 and LSPR portion 114. For example, multiple fluid channels 130 may assist in getting the entire volume of droplet inside LSPR portion 114.

Figure 40:
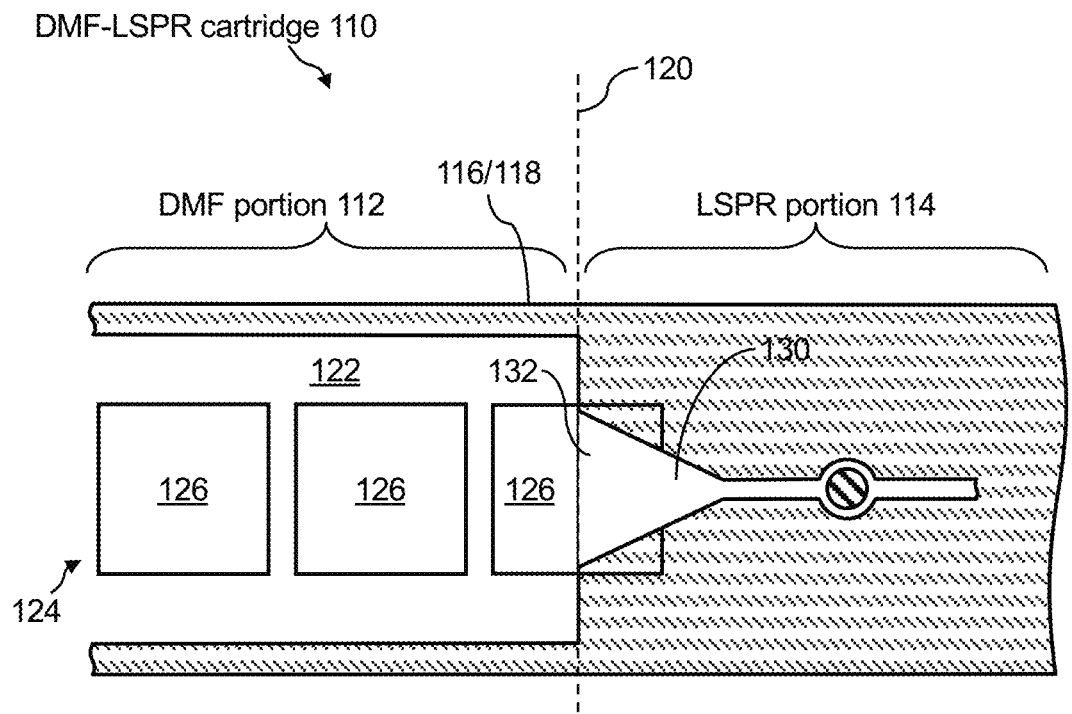
FIG. 40 is a plan view of an example of a fluid channel in which the inlet thereof is tapered or funnel-shaped.

In yet another example, FIG. 40 shows a plan view of an example of a fluid channel 130 in which the inlet thereof (e.g., inlet 132 at boundary droplet operations electrode 126) may be tapered or funnel-shaped, which may be useful to reduce or substantially eliminate dead volume at the interface between DMF portion 112 and LSPR portion 114. For example, multiple fluid channels 130 may assist in getting the entire volume of droplet inside LSPR portion 114. At the same time, there is a desire to maintain a high fluid flow rate in fluid channel 130 and a small channel lends well to that. Accordingly, the tapered or funnel-shaped inlet 132 may assist in both reducing dead volume and maintaining a high fluid flow rate.

Figure 41:
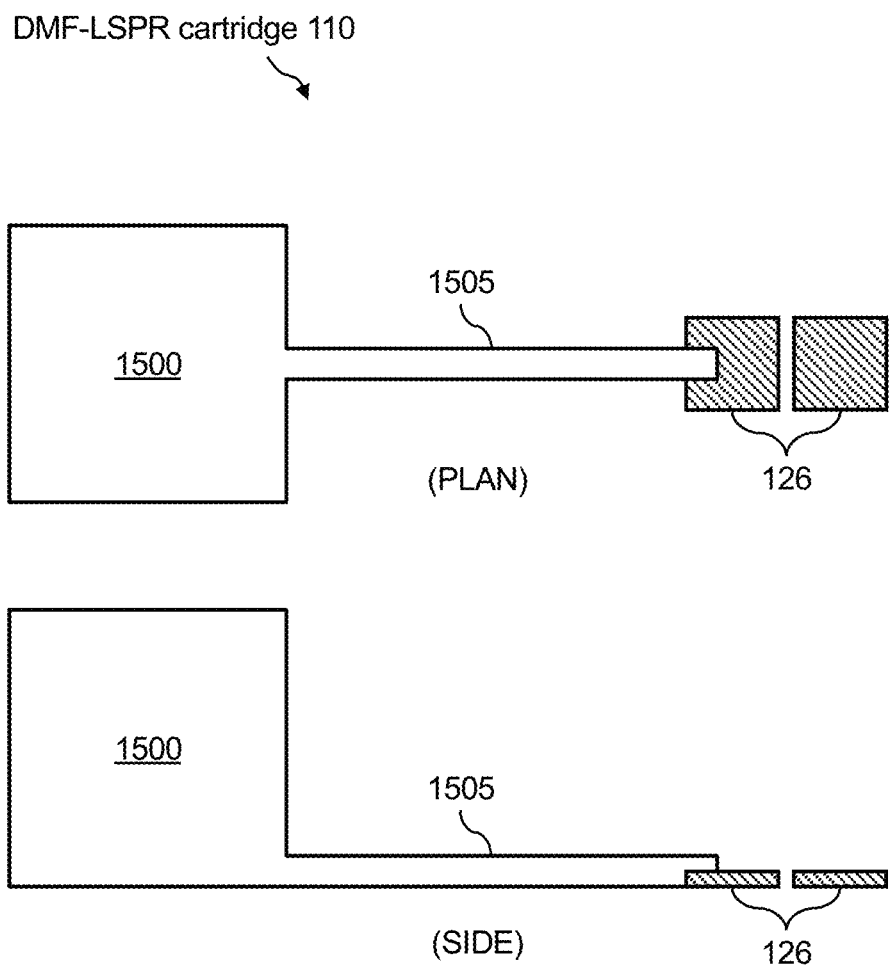
FIG. 41 is a plan view and a side view of an example of a large-volume fluid reservoir.

In yet another example, FIG. 41 shows a plan view and a side view of an example of a large-volume fluid reservoir 1500 that may be useful in, for example, DMF-LSPR cartridge 110. Large-volume fluid reservoir 1500 may be used, for example, to supply large volumes of buffer, such as up to about 2 ml of buffer. Large-volume fluid reservoir 1500 may include a channel 1505 that may supply droplet operations electrodes 126. Channel 1505 may be, for example, a straight line channel or a serpentine channel. Large-volume fluid reservoir 1500 and channel 1505 may be designed in any way to achieve a specific amount of pressure such that the fluid in large-volume fluid reservoir 1500 does not spill out into the droplet operations electrodes 126.

Figure 42:
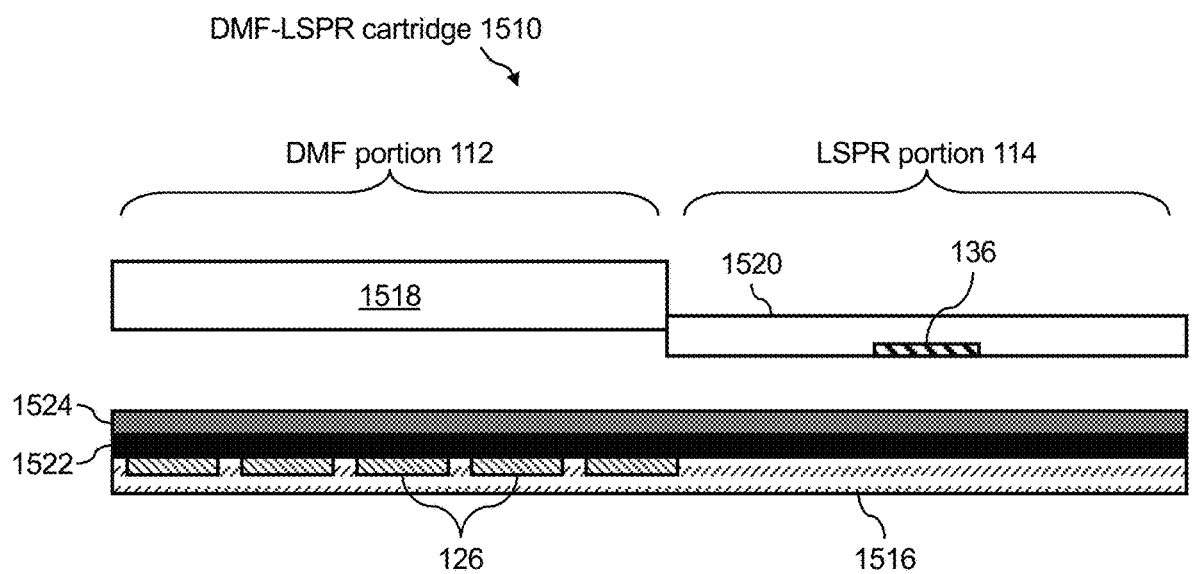
FIG. 42 and FIG. 43 are side views of other examples of the structure of DMF-LSPR cartridges.
Figure 43:
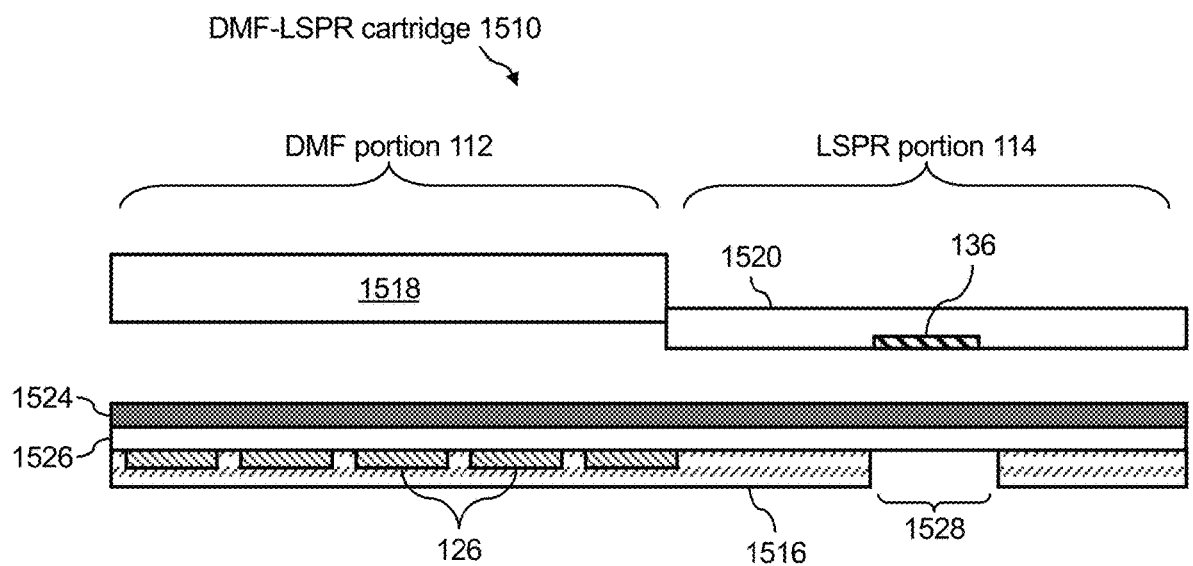

In yet other examples, FIG. 42 and FIG. 43 illustrate side views of other examples of the structure of the presently disclosed DMF-LSPR cartridge. For example and referring now to FIG. 42, a DMF-LSPR cartridge 1510 may include the DMF portion 112 and the LSPR portion 114. DMF-LSPR cartridge 1510 may include a bottom substrate 1516 that is common to both DMF portion 112 and the LSPR portion 114. Bottom substrate 1516 may be, for example, a PCB that may include any arrangement of droplet operations electrodes 126 (e.g., electrowetting electrodes) and reservoir electrodes 128. DMF-LSPR cartridge 1510 may include a top substrate 1518 at DMF portion 112 and a top substrate 1520 at LSPR portion 114. Top substrate 1518 of DMF portion 112 may be formed of TPE coated with ITO. Top substrate 1520 of LSPR portion 114 may be formed of TPE.

DMF-LSPR cartridge 1510 shown in FIG. 42 may be designed for reflection-based measurement; e.g., measuring the LSPR effect using a reflection mode optical system. For example, a non-transparent film 1522 may be provided atop bottom substrate 1516. In one example, non-transparent film 1522 may be a black Kapton film (an opaque film) (e.g., DuPont™ Kapton® B is a black, homogeneous opaque film). Further, a hydrophobic coating 1524 may be provided atop non-transparent film 1522. In one example, hydrophobic coating 1524 may be a Teflon coating (e.g., DuPont™ Teflon® coating).

By contrast, DMF-LSPR cartridge 1510 shown in FIG. 43 may be designed for transmission-based measurement; e.g., measuring the LSPR effect using a transmission mode optical system. In this example, non-transparent film 1522 shown in FIG. 42 may be replaced with a substantially transparent film 1526. In one example, transparent film 1526 may be a clear Kapton film (e.g., clear DuPont™ Kapton® polyimide film). Further, a hydrophobic coating 1524 may be provided atop non-transparent film 1522. In one example, hydrophobic coating 1524 may be a Teflon coating (e.g., DuPont™ Teflon® coating). Further, in the case in which any component of any DMF-LSPR cartridge described herein is not substantially optically transparent an optical aperture may be provided. For example, DMF-LSPR cartridge 1510 may include an optical aperture 1528 in bottom substrate 1516 at LSPR sensor 136 of LSPR portion 114. In the case in which bottom substrate 1516 is a PCB, optical aperture 1528 may be a standard plated through-hole via in the PCB.

In other examples, DMF-LSPR cartridge 1510 may be substantially transparent or can include colored, opaque, or translucent substrates and/or dielectric materials, such as, but not limited to, substrates that include clear Kapton, orange Kapton, or glass as a dielectric.

Figure 44:
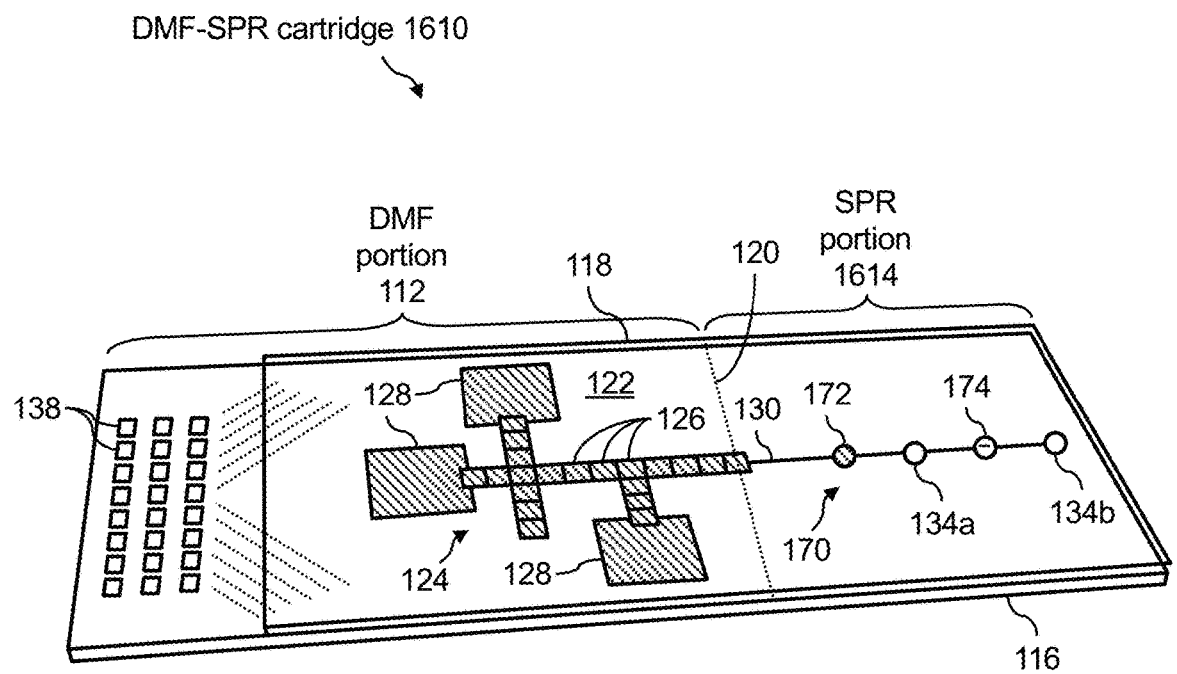
FIG. 44 is a perspective view of an example of a DMF-SPR cartridge.
Figure 44:
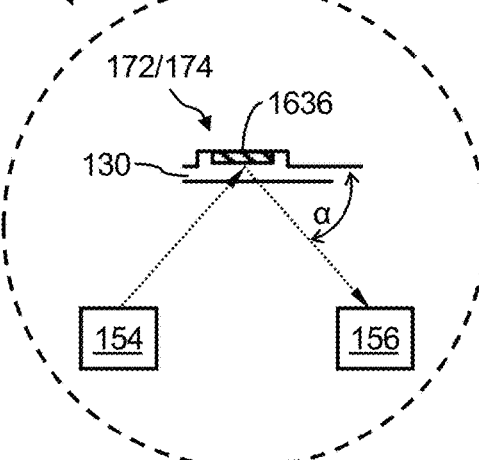

Further, the presently disclosed PR system 800 is not limited to a cartridge (e.g., DMF-LSPR cartridge 110) that supports both DMF capability and LSPR capability only. In other examples, PR system 800 may include a cartridge that supports both DMF capability and SPR capability, along with an optical detection system that operates in reflection mode rather than transmission mode. For example, FIG. 44 is a perspective view of an example of a DMF-SPR cartridge 1610.

DMF-SPR cartridge 1610 may be substantially the same as DMF-LSPR cartridge 110 as described with reference to FIG. 20 through FIG. 43 except that it may include an SPR sensor and a corresponding optical detection system operating in reflection mode instead of an LSPR sensor and a corresponding optical detection system operating in transmission mode. For example, DMF-SPR cartridge 1610 may include DMF portion 112 as described in FIG. 20 through FIG. 43 in combination with an SPR portion 1614. SPR portion 1614 may be substantially the same as LSPR portion 114 of DMF-LSPR cartridge 110 except that LSPR sensor 136 may be replaced with an SPR sensor 1636. For example, SPR portion 1614 may include in-line reference channel 170 that may further include one or more sample spots 172 and/or one or more reference spots 174, wherein each sample spot 172 and each reference spot 174 may include an SPR sensor 1636.

Each of the SPR sensors 1636 may be interrogated optically in reflection mode. For example, illumination sources 154 and optical measurement devices 156 may be arranged on one side of SPR sensors 1636 wherein the reflectance angle α can be measured (see Detail A of FIG. 44). In operation, the reflectance angle α may be measured prior to binding. Then binding occurs which causes the reflectance angle α to change. The amount of change indicates the antibody affinity. Other sensors can also be used in place of the SPR or LSPR sensor. For example, optical sensors may be used, such as biolayer interferometry, piezoelectric sensors, and electrical sensors.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some examples ±100%, in some examples ±50%, in some examples ±20%, in some examples ±10%, in some examples ±5%, in some examples ±1%, in some examples ±0.5%, and in some examples ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

While examples have been illustrated and described in detail in the drawings and foregoing description, such illustration and description is to be considered as exemplary and not restrictive in character. For example, certain examples described hereinabove may be combinable with other described examples and/or arranged in other ways (e.g., process elements may be performed in other sequences). Accordingly, it should be understood that only the preferred example and variants thereof have been shown and described and that all changes and modifications that come within the spirit of the disclosure are desired to be protected.

What is claimed is:

1. A cartridge for use with an instrument, comprising:
a digital microfluidics (DMF) portion comprising at least one electrode to perform fluid operations on a fluid in the DMF portion;
an analog fluid portion comprising at least one fluid channel, wherein the at least one fluid channel is fluidly coupled with the DMF portion for receipt of a fluid from the DMF portion to provide a continuous flow of the fluid in the at least one fluid channel; and
a sensor located in the at least one fluid channel, wherein the analog fluid portion is configured to flow the fluid provided in the at least one fluid channel into contact with the sensor for real-time measurement of the fluid by the sensor.

2. The cartridge of claim 1 wherein the analog fluid portion is configured to flow the fluid provided in the at least one fluid channel across the surface of the sensor for real-time measurement of the fluid by the sensor.

3. The cartridge of claim 1, wherein the sensor is located on a surface of the at least one fluid channel.

4. The cartridge of claim 1, wherein the at least one fluid channel comprises an enlarged region for accommodating a sensor and the sensor is located on a surface of the enlarged region.

5. The cartridge of claim 4 wherein the enlarged region is substantially ovular or circular disk-shaped.

6. The cartridge of claim 1, wherein the fluid comprises a liquid reagent, buffer solution, or liquid sample.

7. The cartridge of claim 1, wherein the sensor comprises a surface plasmon resonance (SPR) sensor for real-time measurement of an optical signal of the SPR sensor in response to the continuous flow of the fluid in the at least one fluid channel.

8. The cartridge of claim 7, wherein the fluid is present in the cartridge and comprises an analyte fluid comprising an analyte and is flowing in the continuous flow portion at the SPR sensor establishing a mass transport rate of the analyte that is higher than a binding rate of the analyte fluid at the SPR sensor.

9. The cartridge of claim 8 wherein the fluid is flowing in the continuous flow portion at a flow rate not less than about 25 nl/min and not greater than about 10,000 µl/min.

10. The cartridge of claim 7, further comprising:
a reservoir electrode in the DMF portion to receive and maintain the fluid in the DMF portion; and
a plurality of droplet operation electrodes in the DMF portion that are operative to supply the fluid from the reservoir electrode to the at least one fluid channel of the analog fluid portion.

11. The cartridge of claim 7, further comprising:
a plurality of reservoir electrodes in the DMF portion each maintaining a different fluid; and
wherein the at least one electrode is disposed relative to the plurality of reservoir electrodes to perform mixing of the different fluids prior to providing the fluid to the at least one fluid channel of the analog fluid portion.

12. The cartridge of claim 7, further comprising at least one boundary electrode disposed at a boundary between the DMF portion and the analog fluid portion wherein the boundary electrode is disposed relative to the at least one fluid channel to allow a fluid droplet at the boundary electrode to enter the at least one fluid channel.

13. The cartridge of claim 12 wherein the boundary electrode is disposed at, but does not span, the boundary between the DMF portion and the analog fluid portion.

14. The cartridge of claim 12 wherein the boundary electrode overlaps the boundary between the DMF portion and the analog fluid portion.

15. The cartridge of claim 7, further comprising an electrical contact in electrical communication with the electrode wherein the electrical contact is configured for interface with a controller for control of the at least one electrode.

16. The cartridge of claim 7, wherein the at least one electrode is configured to perform the fluid operation by electrowetting.

17. The cartridge of claim 7, further comprising:
a feedback sensor operative to detect droplet operation of the DMF portion, the feedback sensor being operable to communicate with the controller to provide feedback regarding the droplet operation such that the controller may control the at least one electrode to supply droplets as needed to prevent introduction of filler media from the DMF portion into the the at least one fluid channel of the analog fluid portion.

18. The cartridge of claim 17 wherein the feedback sensor comprises at least one of a capacitive or an optical sensor, and optionally wherein a transition electrode doubles as an element of the sensor.

19. The cartridge of claim 17, wherein the feedback sensor is operative to measure a droplet position, velocity, and volume of a droplet in the DMF portion.

20. The cartridge of claim 7, wherein the SPR sensor comprises a sensor surface comprising one of nanosized structures distributed on the sensor surface or a continuous film comprising nano-sized features.

21. The cartridge of claim 7, wherein the sensor surface of the SPR sensor is functionalized with a specific capture molecule to which a target molecule of an analyte fluid binds to change the optical signal of the SPR sensor.

22. The cartridge of claim 21 wherein the capture molecule comprises a ligand immobilized on the surface of the sensor that is sensitive to binding with the target molecule of the analyte fluid to change optical properties of the surface of the sensor resulting in the change of the optical signal of the SPR sensor.

23. The cartridge of claim 22 wherein the change of the optical properties comprises a change in the optical signal resulting from light interacting with the sensor surface.

24. The cartridge of claim 7, wherein the optical signal is detected within about 1000 nm from the sensor surface.

25. The cartridge of any claim 7, wherein the optical signal is detected within about 100 nm from the sensor surface.

26. The cartridge of claim 7, wherein the SPR portion is substantially transparent to an illumination source incident on the SPR sensor on at least one side of the SPR sensor to facilitate real-time optical measurement of the SPR sensor in a reflectance mode.

27. The cartridge of claim 7, wherein the SPR portion is substantially transparent to an illumination source incident on the SPR sensor on opposite sides of the SPR sensor to facilitate real-time optical measurement of the SPR sensor in a transmission mode.

28. The cartridge of claim 7, wherein the cartridge is a multiple-channel cartridge comprising:
a plurality of fluid channels; and
a plurality of droplet operations electrodes disposed relative to the plurality of fluid channels that are operative to supply a continuous fluid flow of fluid to the plurality of fluid channels.

29. The cartridge of claim 7, further comprising:
a fluid inlet at a boundary of the DMF portion and the analog fluid portion in fluid communication with the at least one fluid channel; and
a fluid outlet in fluid communication with the at least one fluid channel and operable to engage with a flow mechanism to establish the continuous fluid flow in the at least one fluid channel between the fluid inlet and the fluid outlet;
wherein the fluid comprises an analyte fluid; and
wherein the SPR sensor is operable to detect analyte affinity of the analyte fluid from the continuous fluid flow in the at least one fluid channel.

* * * * *